(12) United States Patent
Chinnaiyan et al.

(10) Patent No.: US 10,774,122 B2
(45) Date of Patent: Sep. 15, 2020

(54) ERG TARGETED THERAPY

(71) Applicant: The Regents of the University of Michigan, Ann Arbor, MI (US)

(72) Inventors: Arul Chinnaiyan, Plymouth, MI (US); Xiaoju Wang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/924,377

(22) Filed: Mar. 19, 2018

(65) Prior Publication Data

US 2018/0273595 A1 Sep. 27, 2018

Related U.S. Application Data

(60) Provisional application No. 62/474,239, filed on Mar. 21, 2017.

(51) Int. Cl.

| | | |
|---|---|---|
| *C07K 14/47* | (2006.01) | |
| *A61K 9/127* | (2006.01) | |
| *A61K 47/60* | (2017.01) | |
| *A61K 9/107* | (2006.01) | |
| *A61K 47/54* | (2017.01) | |
| *A61K 47/64* | (2017.01) | |
| *C07K 14/82* | (2006.01) | |
| *A61K 38/00* | (2006.01) | |

(52) U.S. Cl.
CPC .......... *C07K 14/4748* (2013.01); *A61K 9/107* (2013.01); *A61K 9/127* (2013.01); *A61K 47/542* (2017.08); *A61K 47/60* (2017.08); *A61K 47/64* (2017.08); *C07K 14/47* (2013.01); *C07K 14/4705* (2013.01); *C07K 14/82* (2013.01); *A61K 38/00* (2013.01); *C07K 2319/01* (2013.01); *C07K 2319/02* (2013.01); *C07K 2319/09* (2013.01); *C07K 2319/10* (2013.01); *C07K 2319/33* (2013.01); *C07K 2319/61* (2013.01)

(58) Field of Classification Search
None
See application file for complete search history.

(56) References Cited

U.S. PATENT DOCUMENTS

| | | |
|---|---|---|
| 6,261,569 B1 | 7/2001 | Comis et al. |
| 7,718,369 B2 | 5/2010 | Tomlins et al. |
| 8,211,645 B2 | 7/2012 | Tomlins et al. |
| 2009/0061010 A1* | 3/2009 | Zale ..................... A61K 9/5153 424/501 |
| 2009/0239221 A1 | 9/2009 | Chinnaiyan et al. |
| 2011/0207675 A1 | 8/2011 | Chinnaiyan et al. |
| 2016/0319369 A1 | 11/2016 | Tomlins et al. |

FOREIGN PATENT DOCUMENTS

EP 0384523 8/1990

OTHER PUBLICATIONS

Rege et al. ("Amphipahic Peptide-Based Fusion Peptides and Immunoconjugates for the Targeted Ablation of Prostate Cancer Cells" Cancer Research 2007:67 (13)).*
Genscript (https://www.genscript.com/peptide/RP20256-TAT_peptide.html 2019).*
Bechara et al. ("Cell-penetrating peptides: 20 years later, where do we stand" FEBS letters 587(2013) 1693-1702).*
Thambi et al. ("Hypoxia-responsive nanocarriers for cancer imaging and therapy: recent approaches and further perspectives" ChemComm 2016, 53, 8492-8500).*
International Search Report and Written Opinion, International Patent Application No. PCT/US2018/023053, dated Jun. 18, 2018.
Wang, X. "5535: Development of peptidomimetic inhibitors of the ERG transcription factor in prostate cancer" Cancer Research, Apr. 6, 2013, vol. 73, No. 8, suppl, p. 5535.
Wang et al. "Development of Peptidomimetic Inhibitors of the ERG Gene Fusion Product in Prostate Cancer" Cancer Cell, Mar. 23, 2017, vol. 31, pp. 532-548.
Ananias et al., "Nuclear imaging of prostate cancer with gastrin-releasing-peptide-receptor targeted radiopharmaceuticals." Curr Pharm Des. 2008;14(28):3033-47.
Banerjee et al., $^{64}$Cu-labeled inhibitors of prostate-specific membrane antigen for PET imaging of prostate cancer.Ananias et al., "Nuclear imaging of prostate cancer with gastrin-releasing-peptide-receptor targeted radiopharmaceuticals." Curr Pharm Des. 2008;14(28):3033-47. J Med Chem. Mar. 27, 2014;57(6):2657-69.
Barinka et al., "Interactions between human glutamate carboxypeptidase II and urea-based inhibitors: structural characterization." J Med Chem. Dec. 25, 2008;51(24):7737-43.
Barve et al., "Prostate cancer relevant antigens and enzymes for targeted drug delivery." J Control Release. Aug. 10, 2014;187:118-32.
Beeley, N. "Peptidomimetics and small-molecule drug design: towards improved bioavailability and in vivo stability." Trends Biotechnol. Jun. 1994;12(6):213-6.
Birdsey, G. et al., Transcription factor Erg regulates angiogenesis and endothelial apoptosis throughVE-cadherin. The American Society of Hematology. 2008; 111, 3498-3506.
Bottger et al., "Identification of novel mdm2 binding peptides by phage display." Oncogene. Nov. 21, 1996;13(10):2141-7.
Bottger, A. et al., "Molecular characterization of the hdm2-p53 interaction." J Mol Biol. Jun. 27, 1997;269(5):744-56.
Brenner J. C. et al., Mechanistic Rationale for Inhibition of Poly(ADP-Ribose) Polymerase in ETS Gene Fusion-Positive Prostate Cancer. Cancer Cell. 2011; 19, 664-678.

(Continued)

*Primary Examiner* — James H Alstrum-Acevedo
*Assistant Examiner* — Tara L Martinez
(74) *Attorney, Agent, or Firm* — Casimir Jones, S.C.; Tanya Arenson

(57) ABSTRACT

The present disclosure relates to compositions and methods for cancer therapy, including but not limited to, targeted inhibition of cancer markers. In particular, the present disclosure relates to recurrent gene fusions as clinical targets for cancer.

8 Claims, 39 Drawing Sheets

Specification includes a Sequence Listing.

(56) References Cited

OTHER PUBLICATIONS

Cao Q. et al., "Repression of E-cadherin by the polycomb group protein EZH2 in cancer." Oncogene. Dec. 11, 2008;27(58):7274-84.
Carrere S. et al., "Erg proteins, transcription factors of the Ets family, form homo, heterodimers and ternary complexes via two distinct domains." Oncogene. Jun. 25, 1998;16(25):3261-8.
Cerchietti et al., A peptomimetic inhibitor of BCL6 with potent antilymphoma effects in vitro and in vivo. Blood, 2009; 113, 3397-3405.
Chaturvedi, N. et al. Topochemically related hormone structures. Synthesis of partial retro-inverso analogs of LH-RH. Int J Peptides & Protein Res, 1981; 17(1), 72-88.
Chinnaiyan A. M. et al., Chromosomal Aberrations in Solid Tumors. Prog Mol Biol Transl Sci. 2010;95:55-94.
Coy, D.H. et al. Development of a potent bombesin receptor antagonist with prolonged in vivo inhibitory activity on bombesin-stimulated amylase and protein release in the rat. Peptides, 1992; 13(4), 775-781.
Cwirla et al., Peptides on phage: A vast library of peptides for identifying ligands. Proc Natl Acad Sci U S A, 1990. 87(16): p. 6378-82.
Devlin JJ et al., Random peptide libraries: a source of specific protein binding molecules. Science, 1990; 249(4967):404-6.
Dharap, S.S. et al. Tumor-specific targeting of an anticancer drug delivery system by LHRH peptide. Proc Natl Acad Sci USA, 2005; 102, 12962-12967.
Dower, W.J. Targeting growth factor and cytokine receptors with recombinant peptide libraries. Curr Opin Chem Biol, 1998; 2(3): p. 328-34.
Efthymiadis et al., The HIV-1 Tat Nuclear Localization Sequence Confers Novel Nuclear Import Properties. J Biol Chem, 1998; 273, 1623-1628.
Farkhani, S.M., et al. Cell penetrating peptides: Efficient vectors for delivery of nanoparticles, nanocarriers, therapeutic and diagnostic molecules. Peptides, 2014; 57:78-94.
Feng, F.Y., et al., "Molecular pathways: targeting ETS gene fusions in cancer." Clin Cancer Res. Sep. 1, 2014;20(17):4442-8.
Fenrick, R. et al., Both TEL and AML-1 Contribute Repression Domains to the t(12;21) Fusion Protein. Mol Cell Biol, 1999; 19, 6566-6574.
Flajollet, S. et al., Abnormal expression of the ERG transcription factor in prostate cancer cells activates osteopontin. Molecular cancer research, 2011; 9, 914-924.
Golinska, M. et al. Dilute Self-Healing Hydrogels of Silk-Collagen-Like Block Copolypeptides at Neutral pH. Biomacromolecules, 2014; 15, 915.
Huang, S.S. et al. Improving the biodistribution of PSMA-targeting tracers with a highly negatively charged linker. Prostate, 2014; 74(7), 702-713.
Iosub, V. et al. Enantioselective Synthesis of α-Quaternary Amino Acid Derivatives by Sequential Enzymatic Desymmetrization and Curtius Rearrangement of α,α-Disubstituted Malonate Diesters. J Org Chem, 2010; 75 1612-1619.
Jedlicka P, et al. Ewing Sarcoma, an enigmatic malignancy of likely progenitor cell origin, driven by transcription factor oncogenic fusions. Int J Clin Exp Pathol. Mar. 19, 2010;3(4):338-47.
Juszczyk, P. Synthesis of orthogonally protected vicinal diamines with amino acid-based skeleton. Letters in Peptide Science, 2003; 9(4-5), 187-192.
Karosas AO "Ewing's sarcoma." Am J Health Syst Pharm. Oct. 1, 2010;67(19):1599-605.
Kieber-Emmons, T. et al., Therapeutic peptides and peptidomimetics. Curr Opin Biotechnol, 1997; 8(4): 435-41.
Kim, J. et al., Requirement for Specific Proteases in Cancer Cell Intravasation as Revealed by a Novel Semiquantitative PCR-Based Assay. Cell, 1998; 94(3), 353-362.
Klambt C., The *Drosophila* gene pointed encodes two ETS-like proteins which are involved in the development of the midline glial cells. Development, 1993; 117, 163-176.

Letsch, M. et al. Preclinical Evaluation of Targeted Cytotoxic Luteinizing HormoneReleasing Hormone Analogue AN-152 in Androgen-Sensitive and Insensitive Prostate Cancers. Clin Cancer Res, 2003;9, 4505-4513.
Lin, B. et al., Prostate-localized and Androgen-regulated Expression of the Membrane-bound Serine Protease TMPRSS2. Cancer Research, 1999; 59: 4180-4184.
Malik et al., The lncRNA PCAT29 Inhibits Oncogenic Phenotypes in Prostate Cancer. Molecular cancer research, 2014; 12, 1081-1087.
Mansi, R. et al. Targeting GRPR in urological cancers—from basic research to clinical application. Nature Rev Urology, 2013; 10: 235-244.
McLaughlin, F. et al., Combined genomic and antisense analysis reveals that the transcription factor Erg is implicated in endothelial cell differentiation. Blood, 2001; 98, 3332-3339.
Moore, G.J., Designing peptide mimetics. Trends Pharmacol Sci, 1994; 15(4): p. 124-9.
Nagy, A. et al. Cytotoxic analogs of luteinizing hormone-releasing hormone containing doxorubicin or 2-pyrrolinodoxorubicin, a derivative 500-1000 times more potent. Proc Natnl Acad Sci USA, 1996; 93, 7269-7273.
Pan J., et al., TLS-ERG Leukemia Fusion Protein Deregulates Cyclin-Dependent Kinase 1 and Blocks Terminal Differentiation of Myeloid Progenitor Cells. Mol Cancer Res, 2008;6(5):862-72.
Paoloni-Giacobino, A. et al., Cloning of the TMPRSS2 Gene, Which Encodes a Novel Serine Protease with Transmembrane, LDLRA, and SRCR Domains and Maps to 21q22.3. Genomics, 1997; 44: 309-320.
Pavlicek, J. et al. Structural characterization of P1'-diversified urea-based inhibitors of glutamate carboxypeptidase II. Bioorg Med Chem Lett. 2014; 24, 2340.
Pereira DS, et al., Retroviral transduction of TLS-ERG initiates a leukemogenic program in normal human hematopoietic cells. Proc Natl Acad Sci U S A. Jul. 7, 1998;95(14):8239-44.
Presner, J.R. et al., Transcriptome sequencing across a prostate cancer cohort identifies PCAT-1, an unannotated lincRNA implicated in disease progression. Nature biotechnology, 2011; 29, 742-749.
Rubin, M.A. et al., Common Gene Rearrangements in Prostate Cancer. J Clin Oncol., Sep. 20, 2011;29(27):3659-68.
Salek-Ardakani S., et al. ERG is a Megakaryocytic Oncogene. Cancer Res Jun. 1, 2009; 69(11): 4665-73.
Scott, J.K. et al., Searching for peptide ligands with an epitope library. Science, 1990; 249(4967): p. 386-90.
Sidhu, S.S. et al., [21] Phage display for selection of novel binding peptides. Methods Enzymol, 2000; 328: p. 333-63.
Slovin, S. F. Targeting castration-resistant prostate cancer with monoclonal antibodies and constructs. Immunotherapy, 2013; 5, 1347.
Snyder et al., Treatment of Terminal Peritoneal Carcinomatosis by a Transducible p53-Activating Peptide. PLoS, 2004; 2(2):0186-0193.
Sulochana, et al. "Developing antiangiogenic peptide drugs for angiogenesis-related diseases." Curr Pharm Des. 2007;13(20):2074-86.
Tomlins, S.A. et al., Role of the TMPRSS2—ERG Gene Fusion in Prostate Cancer. Neoplasia, Feb. 2008; 10(2), 177-188.
Tykvart, J. et al. Rational design of urea-based glutamate carboxypeptidase II (GCPII) inhibitors as versatile tools for specific drug targeting and delivery. Bioorg Med Chem. 2014; 22, 4099.
Van Den Berg, A. et al. Protein transduction domain delivery of therapeutic macromolecules. Current Opinion in Biotechnology, 2011; 22:888-893.
Velasco, A.M. et al., Article Navigation Identification and Validation of Novel Androgen-Regulated Genes in Prostate Cancer. Endocrinology, 2004; 145(8): 3913-24.
Verger, A. et al., Identification of Amino Acid Residues in the ETS Transcription Factor Erg That Mediate Erg-Jun/Fos-DNA Ternary Complex Formation. J Biol Chem, 2001; 276(20), 17181-17189.
Voight, E.A. et al. Efficient preparation of chiral diamines via Red-Al reduction of N-Boc-protected amino acid-derived secondary amides. Tetra Letters, 2006; 47(11), 1717.

(56) References Cited

OTHER PUBLICATIONS

Wadia J.S. et al. Transmembrane delivery of protein and peptide drugs by TAT-mediated transduction in the treatment of cancer. Adv Drug Deliv Rev, 2005; 57(4), 579-596.
Yi H, et al. Inhibition of apoptosis by normal and aberrant Fli-1 and erg proteins involved in human solid tumors and leukemias. Oncogene, Mar. 20, 1997;14(11):1259-68.
Yu et al., An Integrated Network of Androgen Receptor, Polycomb, and TMPRSS2-ERG Gene Fusions in Prostate Cancer Progression. Cancer Cell, 2010; 17(5), 443-454.
Yu, Z. et al. An Update of Radiolabeled Bombesin Analogs for Gastrin-Releasing Peptide Receptor Targeting. GRPR Curr Pharm Design, 2013;19(18), Abstract Only.
Zechmann, C.M., et al. Radiation dosimetry and first therapy results with a 124I/131 I-labeled small molecule (MIP-1095) targeting PSMA for prostate cancer therapy. Eur J Nucl Med Mol Imaging, 2014; 41:1280-92.
Zou J., et al., The Oncogenic TLS-ERG Fusion Protein Exerts Different Effects in Hematopoietic Cells and Fibroblasts. Molecular and Cellular Biology, Jul. 2005; 25(14):6235-6246.

\* cited by examiner

FIG. 2D
FIG. 2F
FIG. 2E
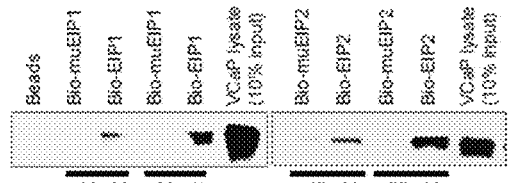
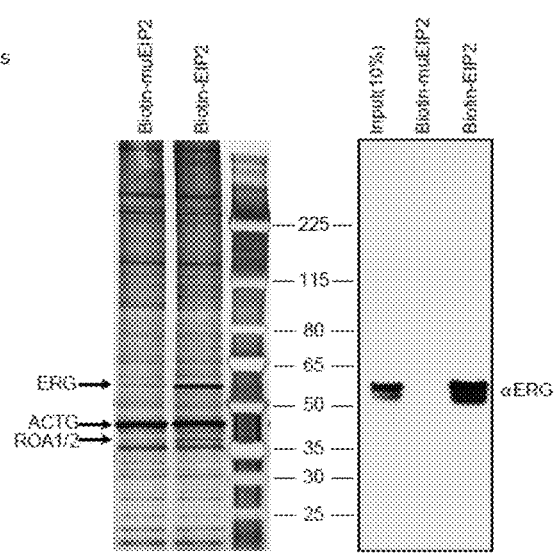
FIG. 2G
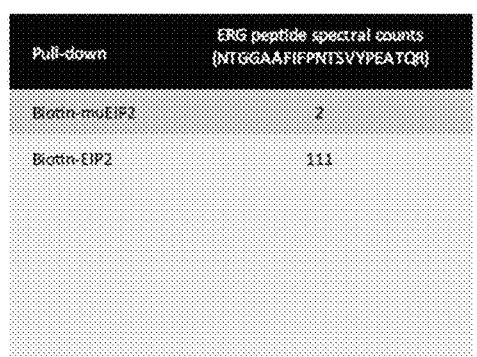

FIG. 3A
| | | |
|---|---|---|
| TAT-EIP1 | LPPYLFTGGRKKRRQRRRG | (SEQ ID NO:82) |
| TAT-EIP2 | LSFGSLPGGRKKRRQRRRG | (SEQ ID NO:83) |
| TAT-muEIP1 | LPPALFTGGRKKRRQRRRG | (SEQ ID NO:84) |
FIG. 3B
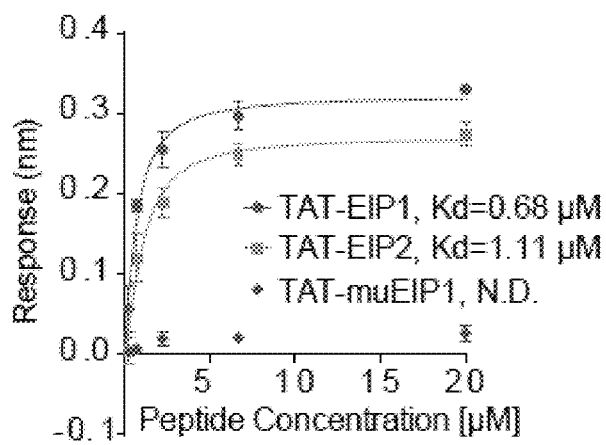
FIG. 3C
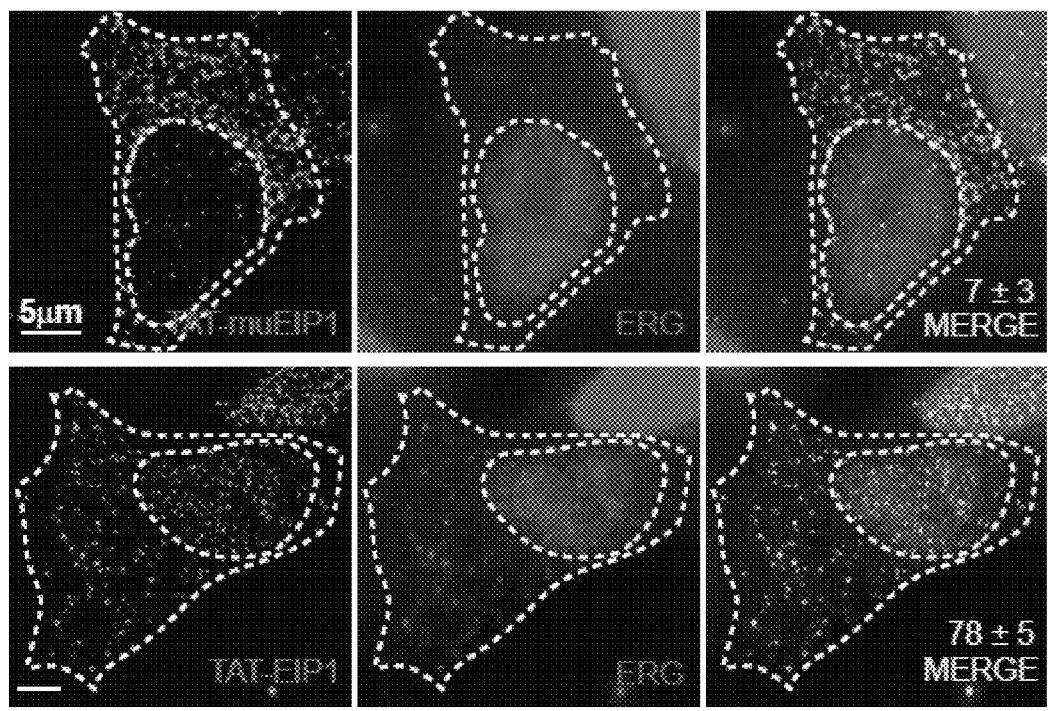

FIG. 4A
RI-EIP1    GRRRQRRKKRGGTFLYPPL (SEQ ID NO:85)
RI-EIP2    GRRRQRRKKRGGPLSGFSL (SEQ ID NO:86)
RI-muEIP1  GRRRQRRKKRGGTFLGPPL (SEQ ID NO:87)
FIG. 4B
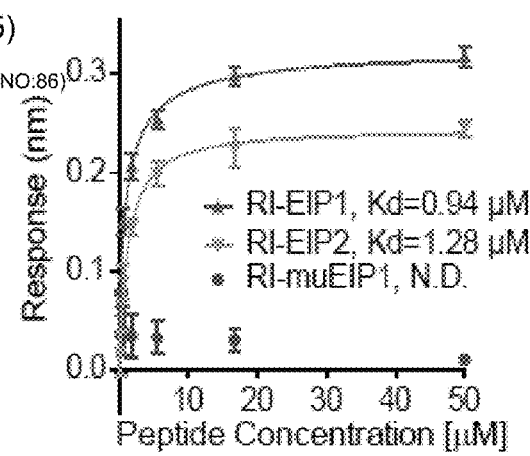
FIG. 4C
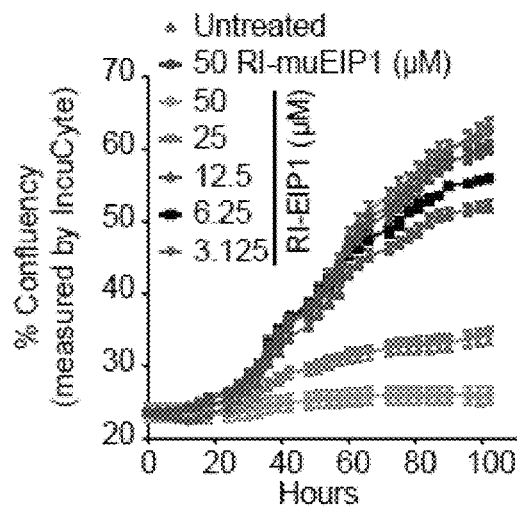
FIG. 4D
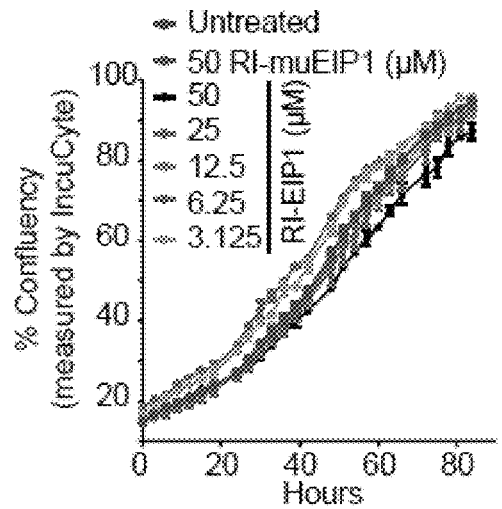

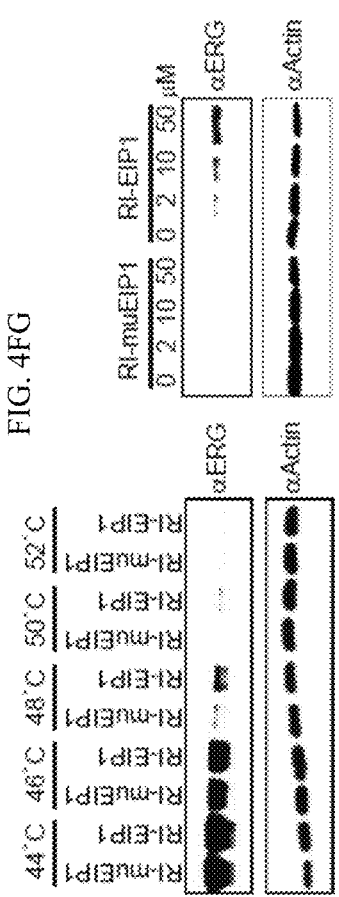
FIG. 4F
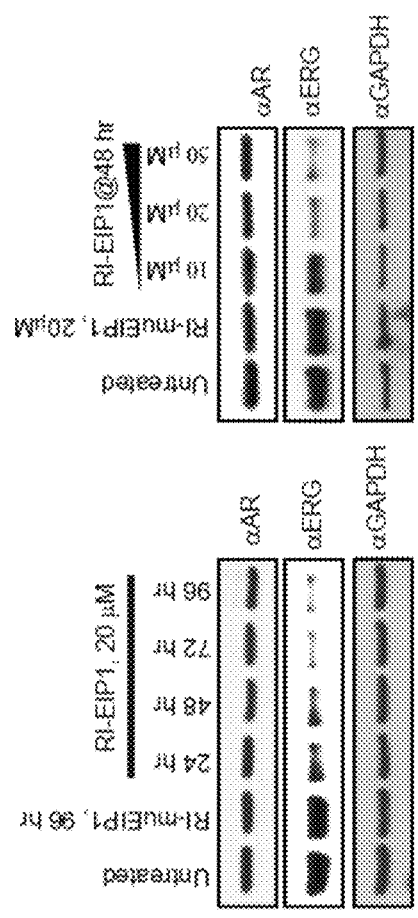
FIG. 4FG
FIG. 4FI
FIG. 4H
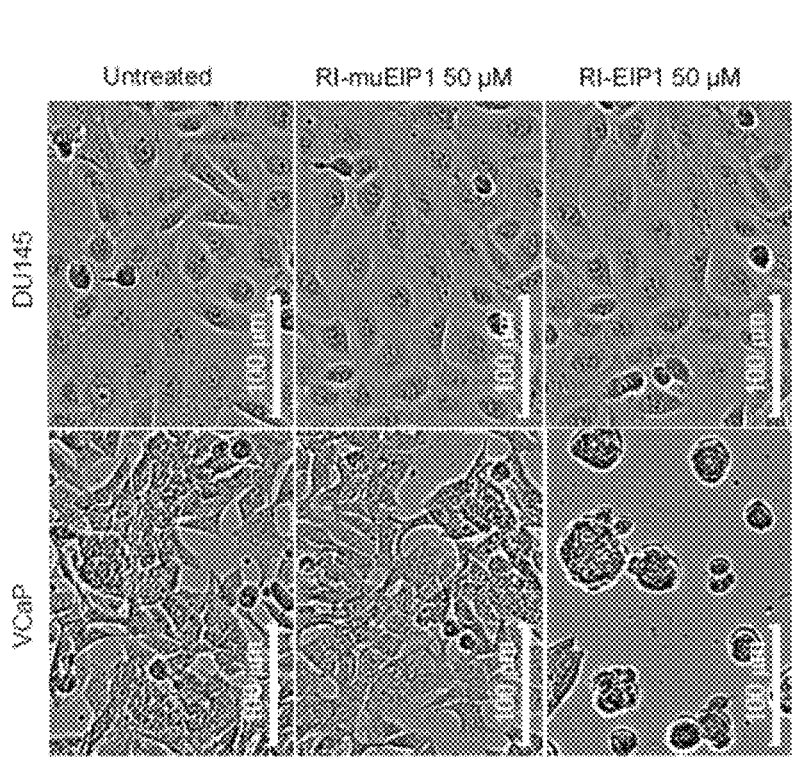
FIG. 4E

FIG. 6A     FIG. 6B
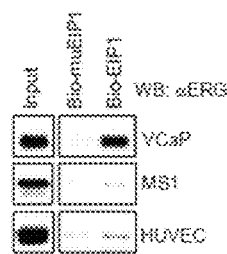
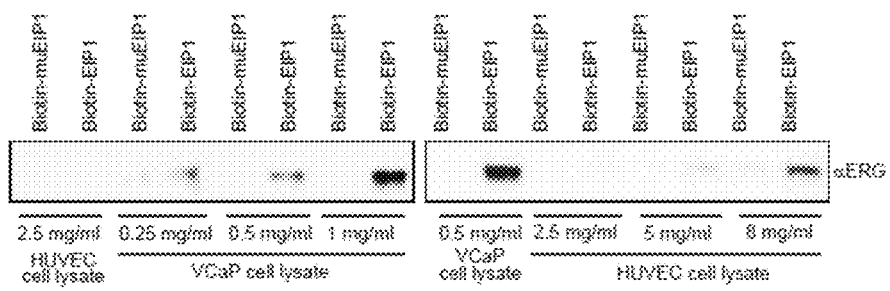
FIG. 6C
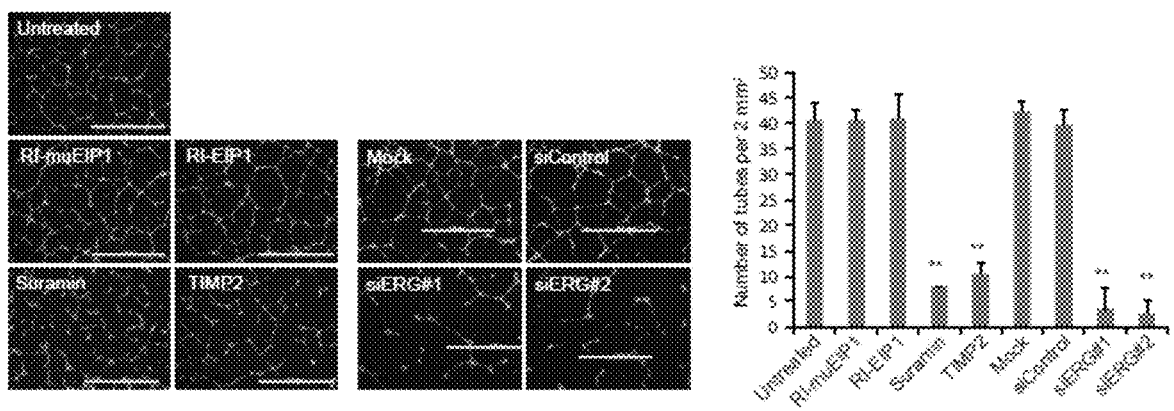

FIG. 8A
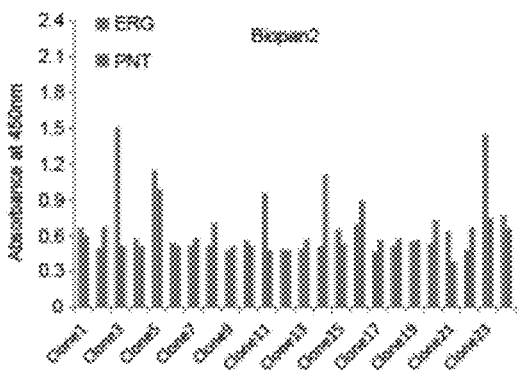
FIG. 8B
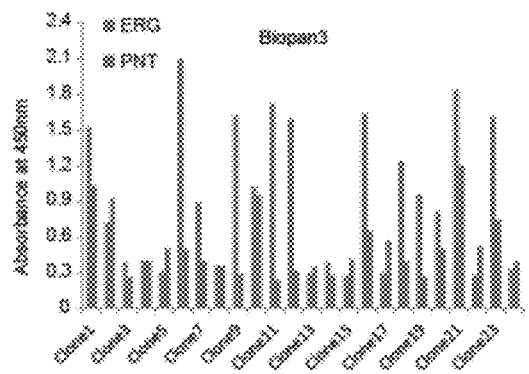
FIG. 8C
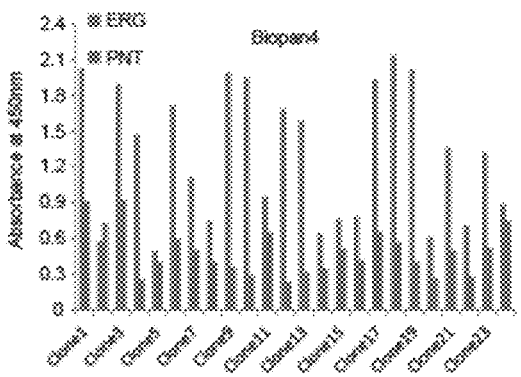
FIG. 8D
FIG. 8E
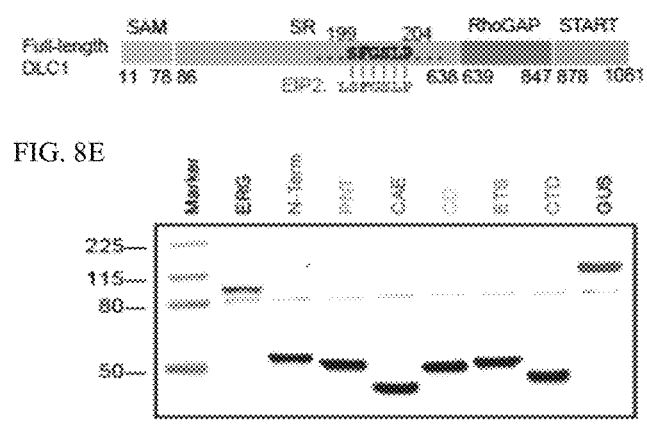
FIG. 8F
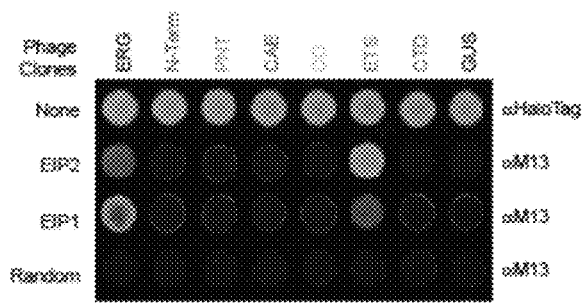
FIG. 8G
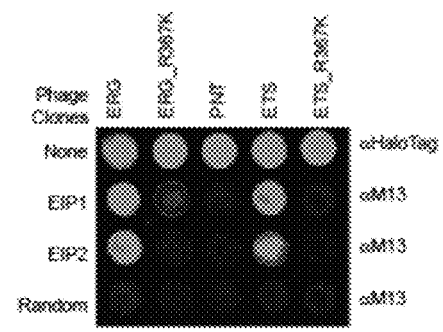

FIG. 11

```
Murine-ERG   MIQTVPDPAAHIKEALSVVSEDQSLFECAYGTPHLAKTEMTASSSSDYGQTSKMSPPVEQ  60 (SEQ ID NO:114)
human-ERG    ----------MASTIKEALSVVSEDQSLFECAYGTPHLAKTEMTASSSSDYGQTSKMSPRVEQ  53 (SEQ ID NO:115)
Chick-ERG    ----------MASTIKEALSVVSEDQSLFECAYGSPHLAKTEMTASSSSEYGQTSKMSPRVPQ  53 (SEQ ID NO:116)
                       * ******************* ********** ** ** *** **  *

Murine-ERG   QDWLSQAPARVTIKMECNPSQVNGSRNSPDECSVRKGGKMVGSPDTVGMSYGSYMEEKHV  120
human-ERG    QDWLSQPPARVTIKMECNPSQVNGSRNSPDECSVAKGGKMVGSPDTVGMNYGSYMEEKHM  113
Chick-ERG    QDWLSQPPARVTIKMECNPNQVNGSRNSPDDCSVAKGGKMVSSSDNVGMNYGSYMEEKHI  113
             ****** ************ ********** *** ******   *  ** **********

Murine-ERG   PPPNMTTNERRVIVPADPTLWSTDHVRQWLEWAVKEYGLLDVDVLLFQNIDGKELCKMTK  180
human-ERG    PPPNMTTNERRVIVPADPTLWSTDHVRQWLEWAVKEYGLPDVNILLFQNIDGKELCKMTK  173
Chick-ERG    PPPNMTTNERRVIVPADPTLWSTDHVRQWLEWAVKEYGLPDVDILLFQNIDGKELCKMTK  173
             ***************************************  *  ****************

Murine-ERG   DDFQRLTPSYNADILLSHLHYLRETPLPHLTSDDVDKALQNSPRLMHARNTGGAAFIFPN  240
human-ERG    DDFQRLTPSYNADILLSHLHYLRETPLPHLTSDDVDKALQNSPRLMHAPNTGGAAFIFPN  233
Chick-ERG    DDFQRLTPSYNADILLSHLHYLRETPLPHLTSDDVDKALQNSPRLMHAPNTGGATFIFPN  233
             **********************************************  *****  *****

Murine-ERG   TSVYPEATQRIFTRPDLPYEPPRFSAWTGHSHLTPQSKAAQPSPSAVPKTEDQRPQLDPY  300
human-ERG    TSVYPEATQRITTFPDLPYEPPRSAWTGHGHPTPQSKAAQPSPSTVPKTEDQRPQLDPY   293
Chick-ERG    TSVYPEATQRITTFPDLPYEQARKSAWTSHSRPT-QSKAEQPSSTVPKTEDQRPQLDPY   292
             ***********  * *****   * **** *   * ****  ***  **************

Murine-ERG   QILGPTSSRLANPGSGQIQLWQFLLELLSDSSRSNCITWEGTNGEFKMTDPDEVARRWGE  360
human-ERG    QILGPTSSRLANPGSGQIQLWQFLLELLSDSSRSSCITWEGTNGEFKMTDPDEVARRWGE  353
Chick-ERG    QILGPTSSRLANPGSGQIQLWQFLLELLSDSSNSNCITWEGTNGEFKMTDPDEVARRWGE  352
             ********************************  *************************

Murine-ERG   RKSKPNMNYDKLSRALRYYYDKNIMTKVHGKRYAYKFDFHGIAQALQPHPPESSLYKYPS  420
human-ERG    RKSKPNMNYDKLSRALRYYYDKNIMTKVHGKRYAYKFDFHGIAQALQPHPPESSLYKYPS  413
Chick-ERG    RKSKPNMNYDKLSPALRYYYDKNIMTKVHGKRYAYKFDFHGIAQALQPHPPESSMYKYPS  412
             ************* ***************************************  ****

Murine-ERG   DLPYMGSYHAHPQKMNFVSPHPPALPVTSSSFFASPNPYWNSPTGGIYPNTRLPASHMPS  480
human-ERG    DLPYMGSYHAHPQKMNFVAPHPPALPVTSSSFFAAPNPYWNSPTGGIYPNTRLPTSHMPS  473
Chick-ERG    DLPYMSSYHAHPQKMNFVAPHPPALPVTSSSFFAAPNPYWNSPTGGIYPNERLPAAHMPS  472
             ***** ************  *************  **************** ** ****

Murine-ERG   HLGTYY  486
human-ERG    HLGTYY  479
Chick-ERG    HLGTYY  478
             ******
```

FIG. 12A
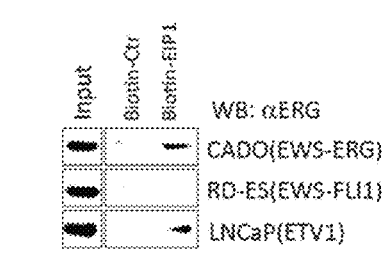
FIG. 12B
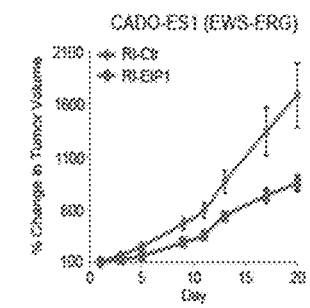
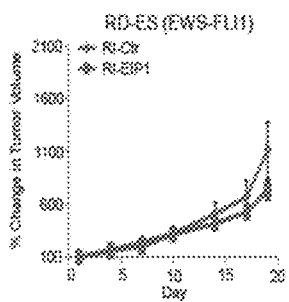
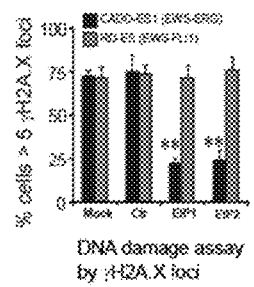
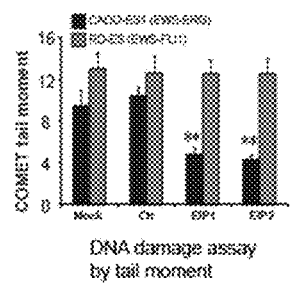
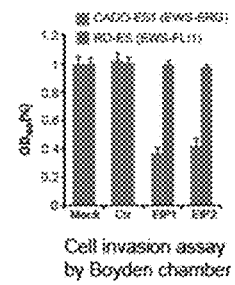
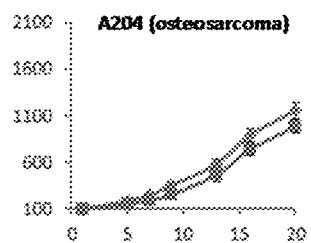
FIG. 13
| ID | N-Terminus | Sequence | C-Terminus | $K_d[\mu M]$ |
|---|---|---|---|---|
| EIP1 | H$_2$N- | LPPYLFT | -OH | 0.9716 |
| 7LT-A | Ac- | LPPYLFT | -NH$_2$ | >100 |
| 7LT-4D | Ac- | LPPDLFT | -NH$_2$ | >100 |
| 7LT-4F | Ac- | LPPFLFT | -NH$_2$ | >100 |
| 7LT-4E | Ac- | LPPELFT | -NH$_2$ | 3.605 |
| 7LT-4H | Ac- | LPPHLFT | -NH$_2$ | >100 |
| 7LT-4W | Ac- | LPPWLFT | -NH$_2$ | >100 |
| 7LT-4K | Ac- | LPPKLFT | -NH$_2$ | 4.266 |
| 7LT-5E | Ac- | LPPYEFT | -NH$_2$ | 5.094 |

FIG. 14

| ID | N-Terminus | Sequence | C-Terminus | $K_d[\mu M]$ |
|---|---|---|---|---|
| 7LT-N | $H_2N$- | LPPYLFT | -$NH_2$ | >100 |
| 7LT-A | Ac- | LPPYLFT | -$NH_2$ | >100 |
| 6PT-N | $H_2N$- | PPYLFT | -$NH_2$ | 11.45 |
| 6PT-A | Ac- | PPYLFT | -$NH_2$ | 3.642 |
| 6LF-N | $H_2N$- | LPPYLF | -$NH_2$ | 4.879 |
| 6LF-A | Ac- | LPPYLF | -$NH_2$ | >100 |
| 5PT-N | $H_2N$- | PYLFT | -$NH_2$ | 1.31 |
| 5PT-A | Ac- | PYLFT | -$NH_2$ | 5.148 |
| 5LL-N | $H_2N$- | LPPYL | -$NH_2$ | 9.603 |
| 5LL-A | Ac- | LPPYL | -$NH_2$ | 12.43 |
| 5PF-N | $H_2N$- | PPYLF | -$NH_2$ | 10.17 |
| 5PF-A | Ac- | PPYLF | -$NH_2$ | 9.437 |
| 4PL-N | $H_2N$- | PPYL | -$NH_2$ | >100 |
| 4PL-A | Ac- | PPYL | -$NH_2$ | 2.24 |

FIG. 15

| ID | N-Terminus | Sequence | C-Terminus | $K_d[\mu M]$ |
|---|---|---|---|---|
| 7LT-N | $H_2N-$ | LPPYLFT | $-NH_2$ | None Specific |
| 7LT-A | Ac- | LPPYLFT | $-NH_2$ | None Specific |
| 7LT-ON | $H_2N-$ | LPPYLFT | -OH | 2.8 |
| 7LT-OA | Ac- | LPPYLFT | -OH | 2.8 |
| 4PL-N | $H_2N-$ | PPYL | $-NH_2$ | 94.2 |
| 4PL-A | Ac- | PPYL | $-NH_2$ | 1.4 |
| 4PL-ON | $H_2N-$ | PPYL | -OH | None Specific |
| 4PL-OA | Ac- | PPYL | -OH | No Binding |
| 3PL-N | $H_2N-$ | PYL | $-NH_2$ | No Binding |
| 3PL-A | Ac- | PYL | $-NH_2$ | 7.5 |
| 3PL-ON | $H_2N-$ | PYL | -OH | No Binding |
| 3PL-OA | Ac- | PYL | -OH | 8.7 |

FIG. 16

| ID | N-Terminus | Sequence | C-Terminus | $K_d[\mu M]$ |
|---|---|---|---|---|
| 1-Hyp | Ac- | (Hyp)PYL | -NH$_2$ | NB |
| 2-Hyp | Ac- | P(Hyp)YL | -NH$_2$ | NB |
| 1,2-Hyp | Ac- | (Hyp)(Hyp)YL | -NH$_2$ | NB |
| 4PL-4E | Ac- | PPYE | -NH$_2$ | NB |
| 4PL-Pip1 | Ac- | Pip-PPYL | -NH$_2$ | 3.3 |
| 4PL-Pip2 | Ac- | Pip-βAβA-PPYL | -NH$_2$ | 3.0 |
| 7LT-Pip1 | H$_2$N- | Pip-LPPYLFT | -OH | 1.7 |
| 7LT-Pip2 | H$_2$N- | Pip-βAβA-LPPYLFT | -OH | NB |

FIG. 17

| ID | N-Terminus | Sequence | Structure | C-Terminus | $K_d[\mu M]$ |
|---|---|---|---|---|---|
| 4PL-3F | Pip- | PPFL | | -NH$_2$ | 3.9 |
| 4PL-3Y(Me) | Pip- | PPY(Me)L | | -NH$_2$ | 15.5 |
| 4PL-4A | Pip- | PPYA | | -NH$_2$ | 7.9 |
| 4PL-4D | Pip- | PPYD | | -NH$_2$ | 14.8 |
| 4PL-4Tal | Pip- | PPYTal | | -NH$_2$ | 11.1 |
| 4PL-4Nle | Pip- | PPYNle | | -NH$_2$ | NB |
| 4PL-4Cpg | Pip- | PPYCpg | | -NH$_2$ | 21.4 |
| 4PL-4Cha | Pip- | PPYCha | | -NH$_2$ | 29.3 |
| 4PL-4F | Pip- | PPYF | | -NH$_2$ | NB |
| Y-OA | Ac- | Y | - | -OH | NB |

FIG. 18A
FIG. 18B
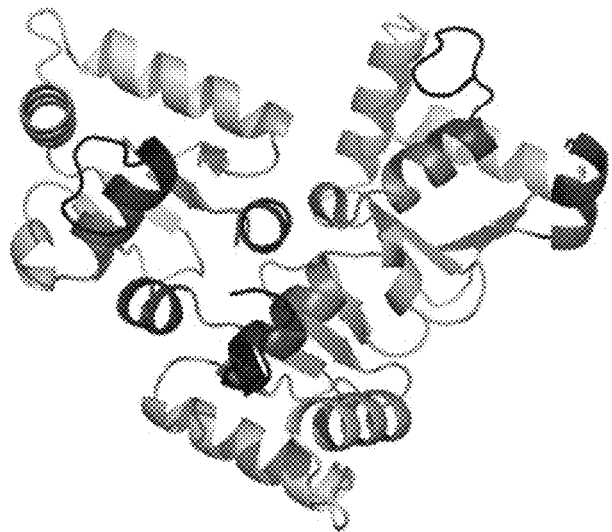
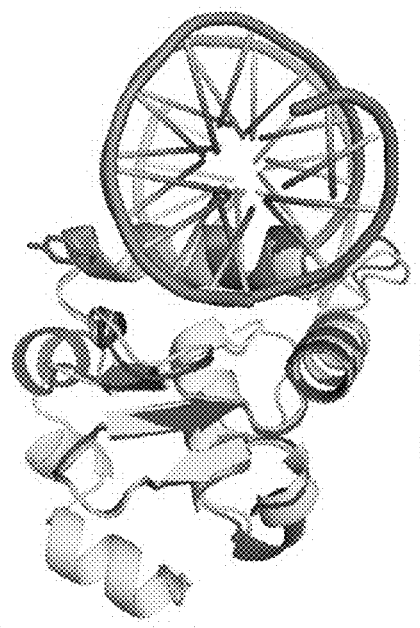
FIG. 18C
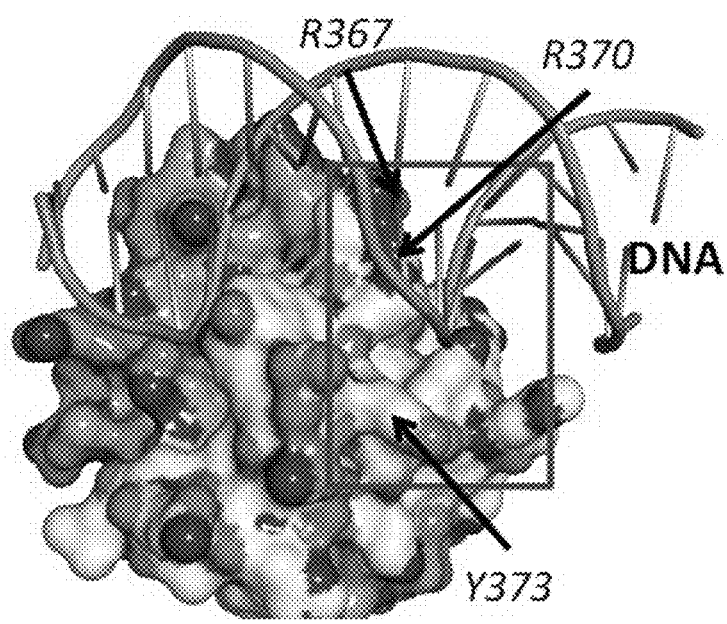

FIG. 21K
ERG  RALRYYYDK
ETV1 RSLRYYYEK
FIG. 21L
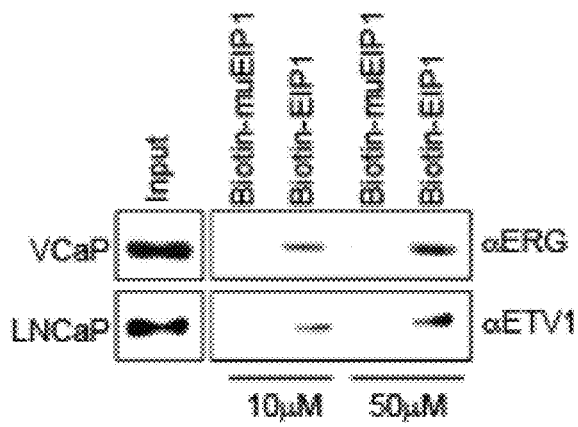
FIG. 21M
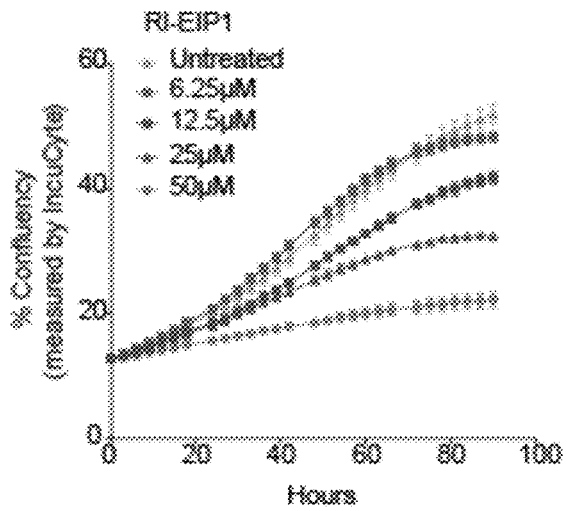
FIG. 21N
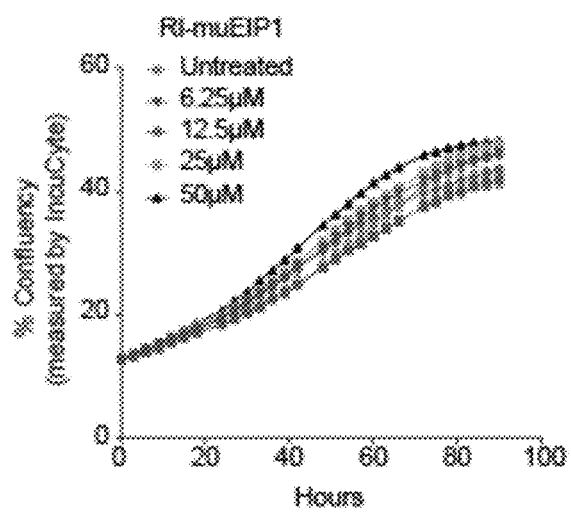
FIG. 21O
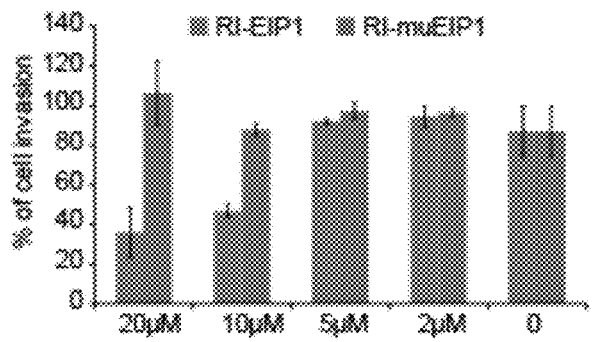
FIG. 21P
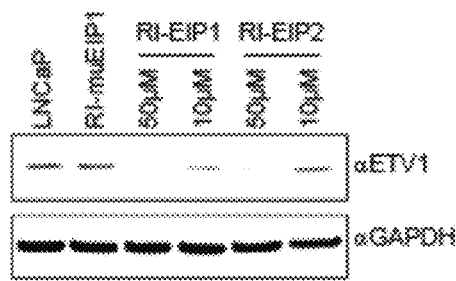

FIG. 21Q
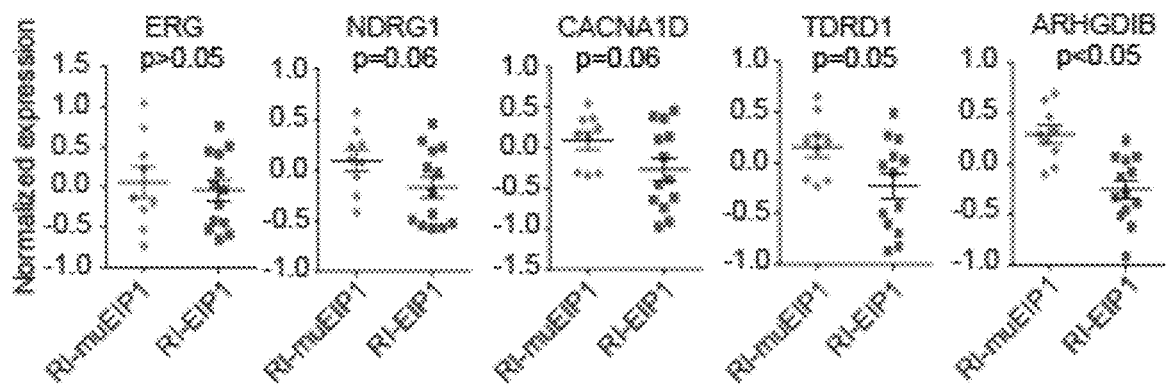
FIG. 22A          FIG. 22B
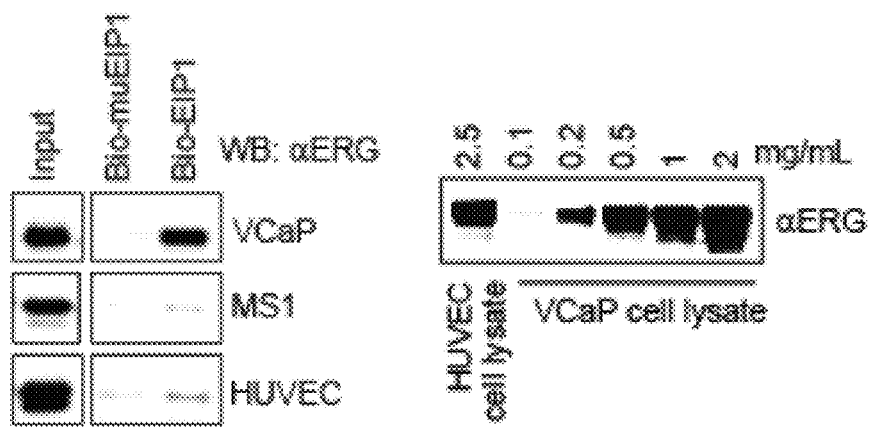
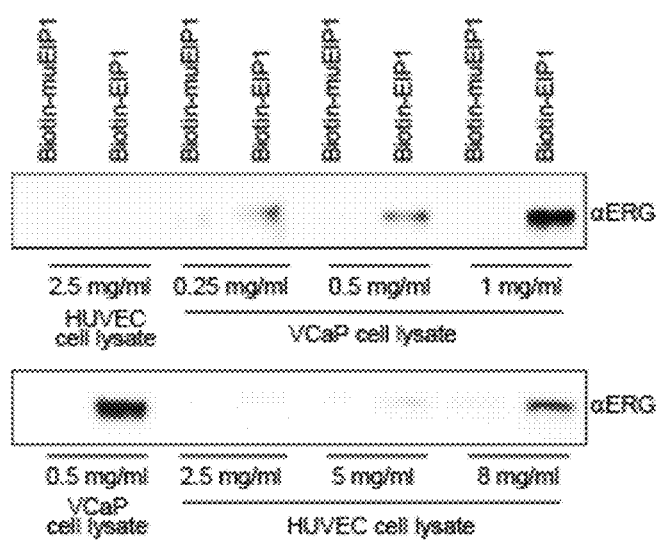
FIG. 22C

ERG TARGETED THERAPY

The present application claims priority to U.S. Provisional application Ser. No. 62/474,239 filed Mar. 21, 2017, which is herein incorporated by reference in its entirety.

STATEMENT REGARDING FEDERALLY SPONSORED RESEARCH OR DEVELOPMENT

This invention was made with government support under CA132874, CA069568 and CA113913 awarded by the National Institutes of Health. The government has certain rights in the invention.

FIELD OF THE DISCLOSURE

The present disclosure relates to compositions and methods for cancer therapy, including but not limited to, targeted inhibition of cancer markers. In particular, the present disclosure relates to recurrent gene fusions as clinical targets for cancer.

BACKGROUND OF THE DISCLOSURE

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, Nat Rev Cancer 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, Mutat Res 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, Nature 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, Nature 243: 290 (1973); de Klein et al., Nature 300: 765 (1982)). Importantly, this finding led to the rational development of imatinib mesylate (Gleevec), which successfully targets the BCR-ABL kinase (Deininger et al., Blood 105: 2640 (2005)). Thus, therapies that target recurrent gene rearrangements in common epithelial tumors are needed.

SUMMARY OF THE DISCLOSURE

The present disclosure relates to compositions and methods for cancer therapy, including but not limited to, targeted inhibition of cancer markers. In particular, the present disclosure relates to recurrent gene fusions as clinical targets for cancer.

For example, in some embodiments, the present disclosure provides a composition comprising a peptide that binds to the ETS domain of an oncogenic ETS family member polypeptide (e.g., preferentially over a non-oncogenic ETS family member polypeptide).

In some embodiments, the present invention provides a composition comprising, in any order, at least one of a peptide or peptidomimetic that binds to the ETS domain of an oncogenic (e.g., pathogenic) ETS family member gene, a peptide or peptidomimetic nuclear localization signal (NLS), and at least one additional peptide or peptidemimetic selected from a cell-penetrating peptide (CPP) domain, or a prostate-selective targeting moiety (PSTM). In some embodiments, at least a portion of the peptide is a retro-inverso or inverso peptide comprising d-amino acids. In some embodiments, the ETS family member gene is ERG, ETV1, ETV6, or ETS1. In some embodiments, the peptide binds to a region of said ETS domain comprising the peptide sequence RALRYYYDK (SEQ ID NO: 1). In some embodiments, the peptide binds to a region of said ETS domain comprising R367 of ERG. In some embodiments, the peptide binds to amino acids R367 to K375 of ERG. In some embodiments, the peptide that binds EIP portion of the compound comprises a l-amino acid sequence selected from, for example, LSFGSLP (SEQ ID NO:2), LPPYLFT (SEQ ID NO:4), or PPYL (SEQ ID NO: 17), or a d-amino acid retroinverso sequence selected from, for example, PLSGFSL (SEQ ID NO: 10), PFTGFTF (SEQ ID NO: 11), TFLYPPL (SEQ ID NO: 12), or LYPP (SEQ ID NO:3).

The present disclosure is not limited to particular NLS, CPP, or PSTM peptides. Exemplary peptides are described herein. In some embodiments, the NLS is, for example, the natural peptide sequence l-PKKKRKV (SEQ ID NO:5), l-PAAKRVKLD (SEQ ID NO:6), l-GKKQYKLKH (SEQ ID NO:8), l-KRSAEGSNPPKPLKKLR (SEQ ID NO:9), l-RKKRRQRRR (SEQ ID NO:7) or l-RQARRNRRRRWR (SEQ ID NO: 13). Or it may be the inverso sequences sequence d-PKKKRKV (SEQ ID NO:5), d-PAAKRVKLD (SEQ ID NO:6), d-GKKQYKLKH (SEQ ID NO:8), d-KRSAEGSNPPKPLKKLR (SEQ ID NO:9), d-RKKRRQRRR (SEQ ID NO:7) or d-RQARRNRRRRWR (SEQ ID NO: 13). Or the corresponding retro-inverso sequences d-VKRKKKP (SEQ ID NO:14), d-DLKVRKAAP (SEQ ID NO:15), d-HKLKYQKKG (SEQ ID NO:16), d-KRSAEGSNPPKPLKKLR (SEQ ID NO:9), d-LRKKLPKPPNSGEASRK (SEQ ID NO:18), RRRQRRKKR (SEQ ID NO: 19), or RWRRRRNRRAQR (SEQ ID NO:20).

In some embodiments, the CPP is selected from, for example. transportan (GWTLNSAGYLLGKINLKA-LAALAKKIL (SEQ ID NO:21)), PEP-1 (KETWWETWW-TEWSQPKKKRKV (SEQ ID NO:22)), MPG (GLAFLG-FLGAAGSTMGAWSQPKKKRKV (SEQ ID NO:23)), p-VEC (LLIILRRRIRKQAHAHSK (SEQ ID NO:24)), MAP (KLALKLALKALKAALKLA (SEQ ID NO:25)), CADY (GLWRALWRLLRSLWRLLWRA (SEQ ID NO:26)), polyR ($R_6$-$R_{12}$), Penetratin (RQIKIWFQNRRM-KWKK (SEQ ID NO:27)), $R_6W_3$ (RRWWRRWRR (SEQ ID NO:28)), P22N (NAKTRRHERRRKLAIER (SEQ ID NO:29)), DPV3 (RKKRRRESRKKRRRES (SEQ ID NO:30)), DPV6 (GRPRESGKKRKRKRLKP (SEQ ID NO:31)), K-FGF (AAVLLPVLLAAP (SEQ ID NO:32)) or C105Y (CSIPPEVKFNKPFVYLI (SEQ ID NO:33)).

In some embodiments, the PSTM is, for example, a peptide targeting Prostate-Specific Membrane Antigen, ErbB2 receptor, the urokinase receptor, Mucin 1, α$_v$β3 integrin, Epidermal growth Factor-Like 7, Prostate Stem Cell Antigen (PSCA); Epithelial Cell Adhesion Molecule (EpCAM); Luteinizing Hormone-Releasing Hormone Receptor (LHRHR (SEQ ID NO:34)); or Gastrin-Releasing Peptide Receptor (GRPR). In some embodiments, the peptide and the NLS, CPP, and/or PSTM are joined by a linker.

In some embodiments, the peptide, including at least one targeting component is, for example, d-(GRKKRRQRRRG-GPLSGFSL (SEQ ID NO:35)); d-(GRWRRRRNRRAQRG-GPLSGFSL (SEQ ID NO:36)); d-(GVKRKKKPGGPLS-GFSL (SEQ ID NO:37)); d-(GRKKRRQRRRGGPFTGFTF (SEQ ID NO:38)); d-(GRWRRRRNRRAQRGGPFTGFTF (SEQ ID NO:39)); d-(GVKRKKKPGGPFTGFTF (SEQ ID NO:40)); d-(GRKKRRQRRRGGTFLYPPL (SEQ ID NO:41)); d-(GRWRRRRNRRAQRGGTFLYPPL (SEQ ID NO:42)); d-(GVKRKKKPGGTFLYPPL (SEQ ID NO:43)); d-(GRKKRRQRRRGGLYPP (SEQ ID NO:44)); d-(GRWR-RRRNRRAQRGGLYPP (SEQ ID NO:45)); d-(GVKRKK-KPGGLYPP (SEQ ID NO:46)); d-(GRKKRRQRRRGG-PLSGFSL (SEQ ID NO:35)); d-(GRWRRRRNRRAQRGGPLSGFSL (SEQ ID NO:36)); d-(GVKRKKKPGGPLSGFSL (SEQ ID NO:37)); d-(GRK-KRRQRRRGGPFTGFTF (SEQ ID NO:38)); d-(GRWR-RRRNRRAQRGGPFTGFTF (SEQ ID NO:39)); d-(GVKRKKKPGGPFTGFTF (SEQ ID NO:40)); d-(GRK-KRRQRRRGGTFLYPPL (SEQ ID NO:41)); d-(GRWR-RRRNRRAQRGGTFLYPPL (SEQ ID NO:42)); d-(GVKRKKKPGGTFLYPPL (SEQ ID NO:43)); d-(GRK-KRRQRRRGGLYPP (SEQ ID NO:44)); d-(GRWRRRRN-RRAQRGGLYPP (SEQ ID NO:45)); d-(GVKRKKKPG-GLYPP (SEQ ID NO:46)); d-(GRKKRRQRRRGGPLSGFSL (SEQ ID NO:35)); d-(GRWRRRRNRRAQRGGPLSGFSL (SEQ ID NO:36)); d-(GVKRKKKPGGPLSGFSL (SEQ ID NO:37)); d-(GRK-KRRQRRRGGPFTGFTF (SEQ ID NO:38)); d-(GRWR-RRRNRRAQRGGPFTGFTF (SEQ ID NO:39)); d-(GVKRKKKPGGPFTGFTF (SEQ ID NO:40)); d-(GRK-KRRQRRRGGTFLYPPL (SEQ ID NO:41)); d-(GRWR-RRRNRRAQRGGTFLYPPL (SEQ ID NO:42)); d-(GVKRKKKPGGTFLYPPL (SEQ ID NO:43)); d-(GRK-KRRQRRRGGLYPP (SEQ ID NO:44)); d-(GRWRRRRN-RRAQRGGLYPP (SEQ ID NO:45)); d-(GVKRKKKPG-GLYPP (SEQ ID NO:46)); d-(H$_2$N-RKKRRQRRRGGPLSGFSL (SEQ ID NO:47)); d-(H$_2$N-RWRRRRNRRAQRGGPLSGFSL (SEQ ID NO:48)); d-(H$_2$N-VKRKKKPGGPLSGFSL (SEQ ID NO:49)); d-(RKKRRQRRRGGPFTGFTF (SEQ ID NO:50)); d-(H$_2$N-RWRRRRNRRAQRGGPFTGFTF (SEQ ID NO:51)); d-(H$_2$N-VKRKKKPGGPFTGFTF (SEQ ID NO:52)); d-(H$_2$N-RKKRRQRRRGGTFLYPPL (SEQ ID NO:53)); d-(H$_2$N-RWRRRRNRRAQRGGTFLYPPL (SEQ ID NO:54)); d-(H$_2$N-VKRKKKPGGTFLYPPL (SEQ ID NO:55)); d-(H$_2$N-RKKRRQRRRGGLYPP (SEQ ID NO:56)); d-(H$_2$N-RWRRRRNRRAQRGGLYPP (SEQ ID NO:57)); d-(H$_2$N-VKRKKKPGGLYPP (SEQ ID NO:58)); l-(GHSSKLQL (SEQ ID NO:59))-d-(GRKKRRQRRRGG-PLSGFSL (SEQ ID NO:35)); l-(GHSSKLQL (SEQ ID NO:59))-d-(GRWRRRRNRRAQRGGPLSGFSL (SEQ ID NO:36)); l-(GHSSKLQL (SEQ ID NO:59))-d-(GVKRKK-KPGGPLSGFSL (SEQ ID NO:37)); l-(GHSSKLQL (SEQ ID NO:59))-d-(GRKKRRQRRRGGPFTGFTF (SEQ ID NO:38)); l-(GHSSKLQL (SEQ ID NO:59))-d-(GRWR-RRRNRRAQRGGPFTGFTF (SEQ ID NO:39)); l-(GHSSKLQL (SEQ ID NO:59))-d-(GVKRKKKPGGPFT-GFTF (SEQ ID NO:40)); l-(GHSSKLQL (SEQ ID NO:59))-d-(GRKKRRQRRRGGTFLYPPL (SEQ ID NO:41)); l-(GHSSKLQL (SEQ ID NO:59))-d-(GRWRRRRN-RRAQRGGTFLYPPL (SEQ ID NO:42)); l-(GHSSKLQL (SEQ ID NO:59))-d-(GVKRKKKPGGTFLYPPL (SEQ ID NO:43)); l-(GHSSKLQL (SEQ ID NO:59))-d-(GRK-KRRQRRRGGLYPP (SEQ ID NO:44)); l-(GHSSKLQL (SEQ ID NO:59))-d-(GRWRRRRNRRAQRGGLYPP (SEQ ID NO:45)); l-(GHSSKLQL (SEQ ID NO:59))-d-(GVKRK-KKPGGLYPP (SEQ ID NO:46)); l-(GHSSKLQL (SEQ ID NO:59))-d-(GRKKRRQRRRGGPLSGFSL (SEQ ID NO:35)); l-(GHSSKLQL (SEQ ID NO:59))-d-(GRWR-RRRNRRAQRGGPLSGFSL (SEQ ID NO:36)); l-(GHSSKLQL (SEQ ID NO:59))-d-(GVKRKKKPGGPLS-GFSL (SEQ ID NO:37)); l-(GHSSKLQL (SEQ ID NO:59))-d-(GRKKRRQRRRGGPFTGFTF (SEQ ID NO:38)); l-(GHSSKLQL (SEQ ID NO:59))-d-(GRWRRRRN-RRAQRGGPFTGFTF (SEQ ID NO:)); l-(GHSSKLQL (SEQ ID NO:59))-d-(GVKRKKKPGGPFTGFTF (SEQ ID NO:40)); l-(GHSSKLQL (SEQ ID NO:59))-d-(GRK-KRRQRRRGGTFLYPPL (SEQ ID NO:41)); l-(GHSSKLQL (SEQ ID NO:59))-d-(GRWRRRRN-RRAQRGGTFLYPPL (SEQ ID NO:42)); l-(GHSSKLQL (SEQ ID NO:59))-d-(GVKRKKKPGGTFLYPPL (SEQ ID NO:43)); l-(GHSSKLQL (SEQ ID NO:59))-d-(GRK-KRRQRRRGGLYPP (SEQ ID NO:44)); l-(GHSSKLQL (SEQ ID NO:59))-d-(GRWRRRRNRRAQRGGLYPP (SEQ ID NO:45)); l-(GHSSKLQL (SEQ ID NO:59))-d-(GVKRK-KKPGGLYPP (SEQ ID NO:46)), d-GRRRQRRKKRGGT-FLYPPL (SEQ ID NO:60); or d-GRRRQRRKKRGGPLS-GFSL (SEQ ID NO:61).

In some embodiments, the composition further comprises a nanostructure. Examples include, but are not limited to, a liposome, a micelle, PEG, or a dendrimer. In some embodiments, the composition is encapsulated in the liposome or micelle or bound to the dendrimer or PEG. In some embodiments, the nanostructure comprises a PSTM on its surface. In some embodiments, the composition is attached to the nanostructure via a linker. In some embodiments, the linker is a selectively cleavable moiety (e.g., HSSKLQL (SEQ ID NO:62) or a hypoxia-sensitive p-nitrobenzyloxy linker).

In still further embodiments, the present disclosure provides a method or use of inhibiting a biological activity of an ETS family member polypeptide in a cell, comprising contacting the cell with any one of the aforementioned peptides. In some embodiments, the cell is a cancer cell (e.g., the cancer cell is a prostate cancer cell, an Ewing sarcoma cell, or a leukemia cell). In some embodiments, the cell is in vivo (e.g., in an animal such as e.g., a human). In some embodiments, the cell is ex vivo. In some embodiments, the ETS family member gene is fused to an androgen regulated gene. In some embodiments, the ETS family member gene is ERG and said androgen regulated gene is TMPRSS2. In some embodiments, the ETS family member gene is ERG or ETV1 and it is fused to EWS. In some embodiments, the ETS family member gene is ERG and it is fused to TLS (translocation liposarcoma). In some embodiments, the biological activity is invasion of the cell, blockage of ERG or ETV1-mediated transcriptional activity, attenuation of cell proliferation, attenuation of DNA damage caused by ERG or ETV1 up-regulation, or blockage of tumor growth.

In some embodiments, the present disclosure provides a method of screening compounds, comprising: contacting a test compound with a gene fusion polypeptide (e.g., comprising an ETS family member gene such as ERG), and assaying the ability of the test compound to alter at least one biological activity of the gene fusion. In some embodiments, the candidate compound is a peptide, peptide mimetic, peptide derivative, or small molecule (e.g., a small molecule that mimics a peptide and/or binds to the same region of ERG, ETV1, ETV6, or ETS1 as the peptides disclosed herein).

In some embodiments, the present disclosure provides the use of any of the aforementioned peptides in the inhibition of a biological activity of a gene fusion (e.g., ETS family member gene fusion such as ERG, ETV1, ETV6, or ETS1).

Additional embodiments are described herein.

DESCRIPTION OF THE FIGURES

FIG. 2A-G shows binding properties of synthetic peptides. (A) The synthetic peptide sequences and corresponding binding affinity (Kd) as determined by OctetRED biolayer interferometry. Point mutations with alanine substitution and scrambled peptide were used as negative controls where Kd could not be determined (N.D.). (B) Representative sensorgrams for ERG binding peptides. (C) Steady-state analysis of real-time binding data for ERG and synthetic peptides. (D) EIP1 and EIP2 disrupt ERG interaction with AR and DNA-PKcs. (E) Interaction of the ERG binding peptide with endogenous ERG protein expressed in VCaP cells. (F) Pull-down experiment was performed as in (E) followed by silver staining (left panel) and parallel immunoblot analysis (right panel). (G) Candidate ERG bands identified in (F) were subjected to mass spectrometric analysis. Spectral counts for the ERG peptide, NTGGAAF-IFPNTSVYPEATQR, are shown for both biotinylated-EIP2 and muEIP2 pull-downs.

FIG. 3A-H shows that cell-permeable EIPs block ERG-mediated cell invasion. (A) Sequences of TAT (shown in green) conjugated peptides. (B) Kinetic binding data for TAT-EIPs and ERG. (C) Representative pseudocolored images of VCaP cells treated with FITC-labeled (left) control peptide muEIP1 (top panels) or EIP1 (bottom panels) and stained for ERG (middle). (D) IP-immunoblot analysis of VCaP cells treated with either TAT-EIPs or -muEIP1, or untreated. (E-H) Boyden chamber transwell invasion assays were performed in chambers pre-coated with Matrigel.

FIG. 4A-M shows that retroinverso EIPs specifically bind to and destabilize ERG. (A) Sequences of the retroinverso peptidomimetics; except glycine, all amino acids are D-isomer. (B) The kinetic binding curve for RI-EIPs as measured by OctetRED as in FIG. 2C. (C-D) Confluence rates was measured by IncuCyte; (C) VCaP or (D) DU145 cells were treated as indicated. (E) Comparison of cell morphology of VCaP and DU145, untreated or treated with 50 μM of indicated peptide at day 4. (F) Evaluation of RI-EIPs target engagement in VCaP cells after the treatment of RI-EIP1 for 3 hours was analyzed over temperature shift from 42° C. to the indicated temperatures. (G) Isothermal dose-response fingerprint at 50° C. in VCaP cells show levels of soluble ERG protein at varying concentrations of RI-EIPs. (H-I) Immunoblot analysis of ERG, AR and GAPDH from VCaP cell treated with RI-EIP1 or RI-muEIP1 at indicated time points and concentrations. (J-K) Immunoblot analysis of ERG and GAPDH from VCaP cells treated with/without RI-EIP1. (K) ERG protein abundance in (J) was quantified by ImageJ and plotted as indicated. (L) Immunoblot analysis of ERG, AR and GAPDH from VCaP cells treated with 20 M RI-EIP1 or RI-muEIP1 for 48 hours with and without proteasome inhibitor carfilzomib. (M) Identification of depleted proteins in VCaP cells after RI-EIP1 treatment.

FIG. 6A-E shows that retroinverso EIPs suppress tumor growth in vivo. (A) Chicken chorioallantoic membrane (CAM) invasion assays were performed using VCaP cells that stably overexpress Cherry Red (red fluorescence emission). (B-C) CAM intravasation and lung metastasis assays were performed on VCaP CAM xenografts. (D) VCaP-xenografted mice were treated with RI-EIP1 or RI-muEIP1 as indicated doses for 18 consecutive days. (E) Kaplan-Meier survival data plotted as percent of animals surviving in each group using a predefined cutoff tumor volume of 1,500 mm³. (F) PC3-xenografts mice were treated with 25 mg/kg RI-EIP1 or RI-muEIP1 and average tumor volume was calculated as in (D). (G) An ETV1-positive human primary prostate cancer serial xenograft was treated as in (D). (H) Immunoblot analysis of ERG, DNA-PKcs and GAPDH in VCaP xenograft tumors treated with 25 mg/kg RI-EIP1 or RI-muEIP1 24 hours after the final treatment in (D). (I) Schematic depicting the mechanisms of EIPs therapeutically targeting TMPRSS2:ERG fusion products in prostate cancer.

FIG. 8A-G shows characterization of ERG binding peptides. (A-C) Validation of randomly selected ERG binding phage clones from the 2nd, 3rd and 4th enrichment using ELISA. (D) Schematic representation of the domain structure of the DLC1 protein. Numbers indicate amino acid residue and functional domains are indicated as: SAM, N-terminal a motif (11-78), SR, serine-rich region (86-638), RhoGAP, Rho-GAP domain (639-847), START, C-terminal steroidogenic acute regulatory protein related lipid-transfer domain (878-1081). (E) Western blot analysis of halo-fusion ERG proteins, ETS sub-domains and GUS control expressed by SP6 High-Yield Wheat Germ lysate. (F-G) Representative protein array image showing phage peptides binding to ETS domain of ERG protein.

FIG. 12A-B shows that peptides of embodiments of the present disclosure inhibit Ewing sarcoma cells. (A) Pull down of ERG in Ewing sarcoma cells containing a EWS-ERG fusion and reduced tumor growth in xenografts models of Ewing sarcoma. (B) Tumors containing the EWS-FLI1 fusion or osteosarcomas (A204) are not affected by treatments with peptides of the disclosure. Treatment with EIP1 and EIP2 peptides reduce DNA damage caused by oncogenic ERG (EWS-ERG fusion) but has no effect on cells containing the EWS-FLI1 fusion. Similarly, invasion potential was reduced by EIP1 and EIP2 treatment in Ewing sarcoma cells containing the EWS-ERG fusion.

FIG. 13 shows the binding affinity of peptide sequences identified from the phage library.

FIG. 14 shows the binding affinity of truncations and N-terminal modifications of the LPPYLFT peptide sequence.

FIG. 15 shows the binding affinity of truncations and C-terminal and N-terminal modifications of the LPPYLFT peptide sequence.

FIG. 16 shows the improvement of water solubility by modifying the LPPYLFT peptide sequence. Several peptides with high affinity to ERG were identified.

FIG. 17 shows mutations of the PPYL peptide sequence affecting the ERG binding profile.

FIG. 18A-F shows X-ray crystal structure and computational binding models between ERG ETS domain and peptides. (A) X-ray crystal structure of ERG ETS DNA binding domain shows three molecules in the asymmetric unit. (B) Structural comparison of ERG ETS domain and Ets-1:DNA complex. (C) A binding model of the ERG ETS domain and DNA based on the alignment of the X-ray crystal structure of the ERG ETS DNA binding domain and the Ets-1:DNA complex (PDBID: 1K7A). Y373, R370, R367 are shown in the stick model and labeled. (E, F) Binding models between the ERG ETS domain and LSFGSLP and LPPYLFT peptides, respectively.

FIG. 22A-M shows that RI-EIPS have no effects on ERG-mediated angiogenesis. (A) Comparison of ERG protein pull downs from VCaP, HUVEC or MS1 cells. (B) Relative ERG levels in HUVEC and VCaP cell lysates as evaluated by immunoblot analysis. (C) Pulldown assay as in (A) with varying amounts of cell lysates as indicated. (D) The soluble ERG protein was measured by cellular thermal shift assay (CETSA) in HUVEC cells treated with 25 µM RIEIP1 as performed in FIG. 4F. (E) Representative microphotographs of a 3D culture of human umbilical vein endothelial cells (HUVEC) (scale bar, 2.0 mm) and mouse endothelial cells (MS1 with high mERG expression) (scale bar, 200 m) in the presence of inhibitors as indicated. (F) Number of tubes/area of cells treated as indicated and analyzed by ImageJ software. (G) The phenotypic effect of RI-EIPs on vascular remodeling was tested in vitro using the Matrigel tube formation assay as in (E) in the presence of varying amount of RI-peptides. (H) Tube formation of siERG HUVEC was analyzed as in (E). (I) Q-PCR analysis of ERG mRNA levels in siERG HUVEC. (J) Effect of RI-peptides or retinoic acid (RA, a known inhibitor of angiogenesis) on VEGF-induced angiogenesis assessed by chorioallantoic membrane assay. (K) The angiogenic index as determined by counting vessel branch points using ImageJ software in a double-blinded manner. (L) A representative immunohistochemistry (IHC) image of mouse CD31, an endothelial cell marker in FFPE sections of VCaP xenograft tumors treated with RI-muEIP1 or RI-EIP1 for 24 consecutive days. (M) The quantitative data of IHC staining.

DEFINITIONS

Figure 1A:
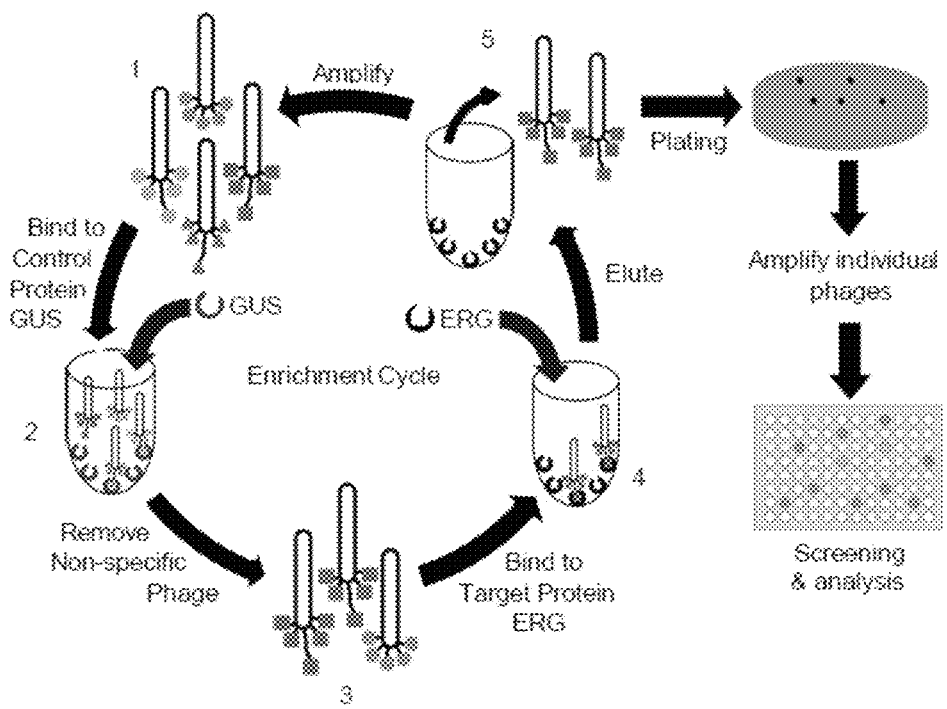
FIG. 1A-C shows identification and characterization of ERG-binding phage peptides. (A) Schematic representation of the phage display workflow to identify ERG-binding peptides. (B) Phage peptide sequences and validation of ERG binding. (C) Mapping of the phage peptide binding residues to the ERG ETS domain.

To facilitate an understanding of the present disclosure, a number of terms and phrases are defined below:

As used herein, the term "retro-inverso" refers to a peptide comprising d-amino acids in a reversed sequence (e.g., relative to a reference peptide). For example, the retro-inverso sequence of the peptide 1-MAGQRL (SEQ ID NO:63)" is "d-LRQGAM (SEQ ID NO:100)."

As used herein, the term "inhibits at least one biological activity of a gene fusion" refers to any agent that decreases any activity of a gene fusion (e.g., including, but not limited to, the activities described herein), via directly contacting gene fusion protein, contacting gene fusion mRNA or genomic DNA, causing conformational changes of gene fusion polypeptides, decreasing gene fusion protein levels, or interfering with gene fusion interactions with signaling partners, and affecting the expression of gene fusion target genes. Inhibitors also include molecules that indirectly regulate gene fusion biological activity by intercepting upstream signaling molecules. In some embodiments, the gene fusion comprises an ETS family member gene.

As used herein, the term "inhibits at least one biological activity of an ETS family member gene" refers to any agent that decreases any activity of an ETS family member gene (e.g., ERG, ETV1, ETV6, or ETS1) (e.g., including, but not limited to, invasion of cells expressing an ETS family member gene, blockage of ERG, ETV1, ETV6, or ETS1-mediated transcriptional activity, attenuation of cell proliferation, attenuation of DNA damage caused by ERG up-regulation, or blockage of tumor growth as well as other activities described herein), via directly contacting the ETS family member protein, contacting the ETS family member mRNA or genomic DNA, causing conformational changes of ETS family member polypeptides, decreasing ETS family member protein levels, or interfering with ETS family member interactions with signaling partners, and affecting the expression of ETS family member target genes. Inhibitors also include molecules that indirectly regulate ETS family member biological activity by intercepting upstream signaling molecules.

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the terms "detect", "detecting" or "detection" may describe either the general act of discovering or discerning or the specific observation of a detectably labeled composition.

As used herein, the term "androgen regulated gene" refers to a gene or portion of a gene whose expression is induced or repressed by an androgen (e.g., testosterone). The promoter region of an androgen regulated gene may contain an "androgen response element" that interacts with androgens or androgen signaling molecules (e.g., downstream signaling molecules).

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein the term "peptidomimetic" refers to a low-molecular-weight nonpeptide molecule or small protein-like chain designed to mimic a native peptide. The altered chemical structure of the native peptide, e.g., replacing L-amino acids with D-amino acids, is intended to advantageously adjust the properties of the native peptide including, but not limited to, metabolic stability and biological activity.

DETAILED DESCRIPTION OF THE DISCLOSURE

The present disclosure relates to compositions and methods for cancer therapy, including but not limited to, targeted inhibition of cancer markers. In particular, the present disclosure relates to recurrent gene fusions as clinical targets for cancer (e.g., prostate cancer, Ewing sarcoma, and leukemias).

In some embodiments, the present disclosure provides therapeutics (e.g., peptide based therapeutics, peptidomimetics, or small molecule therapeutics) that target gene fusions. Gene fusions are described, for example, in U.S. Pat. Nos. 7,718,369 and 8,211,645; U.S. Patent Publication US-2009-0239221; Rubin et al., J Clin Oncol. 2011 Sep. 20; 29(27):3659-68; and Chinnaiyan et al., Prog Mol Biol Transl Sci. 2010; 95:55-94; each of which is herein incorporated by reference in its entirety. In some embodiments, therapeutics target oncogenic (e.g., pathogenic) ETS family member genes (e.g., in gene fusions such as TMPRSS2:ERG gene fusions, EWS:ERG fusions, EWS:ETV1 fusions, or TLS:ERG fusions). The present disclosure is not limited to a particular mechanism. Indeed, an understanding of the mechanism is not necessary to practice the present disclosure. Nonetheless, it is contemplated that targeting portions of gene fusions not found in the native genes (e.g., fusion junctions) or portions of a gene fusion polypeptide that comprise different conformations or post-translational modifications or are involved in different protein-protein interactions that are found only in cancer cells will decrease side effects relative to targeting regions of genes found in all cells.

As described herein, embodiments of the present disclosure provide compositions and methods for inhibiting the activity of recurrent gene fusions associated with cancer (e.g., prostate cancer, Ewing sarcoma, or leukemia). In some embodiments, gene fusions are targeted as anti-cancer therapeutics. In some embodiments, the gene fusions are the result of a fusion between an androgen regulated gene or a housekeeping gene and an ETS family member gene.

Genes regulated by androgenic hormones are of critical importance for the normal physiological function of the human prostate gland. They also contribute to the development and progression of prostate carcinoma. Recognized ARGs include, but are not limited to: DDX5; TMPRSS2; PSA; PSMA; KLK2; SNRK; Seladin-1; and, FKBP51 (Paoloni-Giacobino et al., Genomics 44: 309 (1997); Velasco et al., Endocrinology 145(8): 3913 (2004)). Transmembrane protease, serine 2 (TMPRSS2; NM_005656), has been demonstrated to be highly expressed in prostate epithelium relative to other normal human tissues (Lin et al., Cancer Research 59: 4180 (1999)). The TMPRSS2 gene is located on chromosome 21. This gene is located at 41,750,797-41,801,948 bp from the pter (51,151 total bp; minus strand orientation). The human TMPRSS2 protein sequence may be found at GenBank accession no. AAC51784 (Swiss Protein accession no. 015393)) and the corresponding cDNA at GenBank accession no. U75329 (see also, Paoloni-Giacobino, et al., Genomics 44: 309 (1997)).

In some embodiments, gene fusions comprise transcriptional regulatory regions of an ARG. The transcriptional regulatory region of an ARG may contain coding or non-coding regions of the ARG, including the promoter region. The promoter region of the ARG may further contain an androgen response element (ARE) of the ARG. The promoter region for TMPRSS2, in particular, is provided by GenBank accession number AJ276404.

The E-twenty six (ETS) family of transcription factors regulate the intra-cellular signaling pathways controlling gene expression. As downstream effectors, they activate or repress specific target genes. As upstream effectors, they are responsible for the spacial and temporal expression of numerous growth factor receptors. Almost 30 members of this family have been identified and implicated in a wide range of physiological and pathological processes. These include, but are not limited to: ERG; ETV1 (ER81); FLI1; ETS1; ETS2; ELK1; ETV6 (TEL1); ETV7 (TEL2); GABPα; ELF1; ETV4 (E1AF; PEA3); ETV5 (ERM); ERF; PEA3/E1AF; PU. 1; ESE1/ESX; SAP1 (ELK4); ETV3 (METS); EWS/FLI1; ESE1; ESE2 (ELF5); ESE3; PDEF; NET (ELK3; SAP2); NERF (ELF2); and FEV.

ETS Related Gene (ERG; NM_004449), in particular, has been demonstrated to be highly expressed in prostate epithelium relative to other normal human tissues. The ERG gene is located on chromosome 21. The gene is located at 38,675,671-38,955,488 base pairs from the pter. The ERG gene is 279,817 total bp; minus strand orientation. The corresponding ERG cDNA and protein sequences are given at GenBank accession no. M17254 and GenBank accession no. NP04440 (Swiss Protein acc. no. P11308), respectively.

The ETS translocation variant 1 (ETV1) gene is located on chromosome 7 (GenBank accession nos. NC_000007.11;

NC_086703.11; and NT_007819.15). The gene is located at 13,708330-13,803,555 base pairs from the pter. The ETV1 gene is 95,225 bp total, minus strand orientation. The corresponding ETV1 cDNA and protein sequences are given at GenBank accession no. NM_004956 and GenBank accession no. NP_004947 (Swiss protein acc. no. P50549), respectively.

The human ETV4 gene is located on chromosome 14 (GenBank accession nos. NC_000017.9; NT_010783.14; and NT_086880.1). The gene is at 38,960,740-38,979,228 base pairs from the pter. The ETV4 gene is 18,488 bp total, minus strand orientation. The corresponding ETV4 cDNA and protein sequences are given at GenBank accession no. NM_001986 and GenBank accession no. NP_01977 (Swiss protein acc. no. P43268), respectively.

I. Compositions

In some embodiments, the present disclosure relates to compositions and methods for cancer therapy (e.g., cancers driven by gene fusions involving proteins of the ETS family).

Embodiments of current disclosure provide compositions of the general type [A-B-C-D]E F, wherein at least one of the modules is a peptide that bins to the ETS domain of an ETS family member polypeptide, and optionally at least one additional of A, B, C, D, E, and F is present and are the same or different, and wherein: One of A, B, C and D and optionally E modules is a peptide that binds to the ETS domain of a pathogenic (e.g., oncogenic) ETS family member polypeptide (e.g., preferentially over a non-oncogenic ETS family member polypeptide), referred to herein ETS-Interacting Peptides or EIPs.

Another of the A, B, C and D modules is a peptide sequence that enables the EIP to enter the nucleus of any cell via interaction with the nuclear import mechanism of the cell. Such a peptide sequence is called a Nuclear Localization Signal or NLS. In some embodiments, one or more of the modules is combined in a single peptide (e.g., TAT and REV peptides have both CPP and NLS functionality).

Yet another of the A, B, C and D modules is a peptide sequence that enables the peptide to enter a cell by transporting itself from the extracellular medium through the plasma membrane of the cell. Such a peptide sequence is referred to as a protein transduction domain (PTD) or cell-penetrating peptide (CPP) domain.

Another of the A, B, C and D modules is a prostate-selective targeting moiety or PSTM. In some embodiments, the PSTM comprises a ligand for a cell surface protein that is selectively expressed on either prostatic tumor cells and/or normal prostate cells. In some embodiments, the PSTM is overexpressed in prostate tumor cells when compared to normal prostate cells.

The modules are joined covalently or non-covalently in any order and one or more of the modules are present or absent. In some embodiments, units are connected to one another by peptide bonds. In some embodiments, the PSTM module is bonded to one or more of the other molecules via peptide bonds, or using a molecular linkage that is readily cleaved once the entity is in the proximity of the tumor or absorbed into the tumor cell.

In some embodiments, E is a nanostructure, such as a liposome, lipoprotein, oligomeric PEG, or a dendrimer, which is used to transport the active composition proximal to a tumor. In some embodiments, E has a PSTM moiety attached to it, as for example in being an immunoliposome with an anti-PSMA-antibody (see later) attached to its outer surface. In some embodiments, the nanostructure acts as a PSTM.

In some embodiments the four modules are in a single unbranched chain as illustrated, or one or more of the components may be branched off from another. In some embodiments, the linker entity F is inserted between the PSTM module and the other modules.

In some embodiments, compositions comprise the linker or linker entity F either covalent or non-covalent, to the nanostructure. If covalent, it includes a chemical bond, which, in some embodiments, is readily, and selectively cleaved, to release the active composition in the tumor extracellular space or intracellularly.

Each component of the composition is described in detail below.

A. EIP

In some embodiments, the ETS family member polypeptide targeted by the EIP is ERG. In some embodiments, said EIP binds to a region of said ETS domain comprising the peptide sequence RALRYYYDK (SEQ ID NO: 1) In some embodiments, the EIP binds to a region of said ETS domain comprising R367 of ERG. In some embodiments, the EIP binds to amino acids R367 to K375 of ERG. In some embodiments, the EIP binds more strongly to the form of the ETS protein found in the tumor than to the form found in normal cells.

In some embodiments, the EIP is the 1 or d amino acid sequence or the retro-inverso peptides, comprising d-amino acids in reverse order relative to a reference peptide (e.g. the reverse of the peptides described herein). In some embodiments, the peptides are the following or the retro-inverso peptides of the following: LSFGSLP (SEQ ID NO:2), LPPYLFT (SEQ ID NO:4), or PPYL (SEQ ID NO: 17), or a d-amino acid retroinverso sequence selected from, for example, PLSGFSL (SEQ ID NO: 10), PFTGFTF (SEQ ID NO: 11), TFLYPPL (SEQ ID NO: 12), or LYPP (SEQ ID NO:3).

In some embodiments, peptides or peptidomimetics comprise, consist essentially of, or consist of the amino acid sequences described herein. In some embodiments, peptides comprise 1, 2, 3, 4, 5, 6, 7, 8, 9, 10 or more additional amino acids at one or both ends. In some embodiments, additional amino acids are utilized to alter properties (e.g., solubility, stability, cell invasiveness, biological half life, immunogenicity, oral bioavailability, biological distribution, pharmacodynamics or pharmacokinetics etc.).

In some embodiments, one or more (e.g., 1, 2, 3, 4, or 5) amino acids are substituted for other amino acids, such that the peptides retains its biological activity. In some embodiments, substitutions are conservative substitutions (e.g., amino acids with similar properties (e.g., charge, hydrophobicity, size, etc.). In some embodiments, such amino acids are of the opposite chirality to that of the surrounding amino acids, or contain simple modifications such as α- or N-methylation (e.g., to make the peptides more resistant to peptidase degradation).

The use of peptides as lead compounds, and subsequently conversion into low-molecular-weight nonpeptide molecules (peptidomimetics), has led to development of small-molecule antagonists of intracellular targets (Bottger et al., J Mol Biol, 1997. 269(5): p. 744-56; Bottger et al., Oncogene, 1996. 13(10): p. 2141-7). Therefore, peptidomimetics have emerged as a powerful means for overcoming the limitations inherent in the physical characteristics of peptides, improving their therapeutic potential (Kieber-Emmons et al., Curr Opin Biotechnol, 1997. 8(4): p. 435-41; Beeley, Trends Biotechnol, 1994. 12(6): p. 213-6; Moore et al., Trends Pharmacol Sci, 1994. 15(4): p. 124-9). In some embodiments, compared to native peptides, peptidomimetics possess desirable pharmacodynamic properties superior to natural peptides, including good oral activity, long duration of action, better transport through cellular membranes, decreased rate of excretion, and decreased hydrolysis by peptidases.

Development of a small molecule peptidomimetic generally involves identification of the smallest functional peptide unit capable of inhibiting the targeted interaction. A growing body of literature demonstrates that high-affinity ligands can be selected from peptide libraries displayed on bacteriophages (Sulochana and Ge, Curr Pharm Des, 2007. 13(20): p. 2074-86; Cwirla et al., Proc Natl Acad Sci USA, 1990. 87(16): p. 6378-82; Scott and Smith, Science, 1990. 249 (4967): p. 386-90; Devlin et al., Science, 1990. 249(4967): p. 404-6), and many applications have been directed toward antagonizing the function of a protein ligand (Dower, Curr Opin Chem Biol, 1998. 2(3): p. 328-34; Sidhu et al., Methods Enzymol, 2000. 328: p. 333-63). Because the libraries can be very large ($10^{11}$ or more individual members), no initial assumptions are required concerning how to bias the library, nor the selective enrichment of rare binding phage through biological amplification and rescreening. Those sequences that bind DNA can be identified easily by sequencing their encoding DNA.

In some embodiments, peptide ligands such identified further serve as starting points for a combinatorial chemistry approach or a medicinal chemistry-based peptidomimetic approach for the development of new directed therapeutic agents. In addition, the determination of the structural basis for the high-binding affinity of these peptides for their substrate contributes to the rational design of a therapeutic agent.

B. NLS

In some embodiments, compositions comprise a nuclear localization signal peptide (NLS). Nuclear localization signals allow proteins and peptides containing them to be imported through the nuclear membrane at nuclear pores complexes. About 30 different proteins make up these complexes, and a family of proteins called importins/karypherins are the most important of these. Proteins that are imported into the nucleus must bind to one or more of these proteins, many of which have a common set of 10-20 "armadillo" repeat sequences, which generally bind best to lysine and arginine resides. The best characterized pathway involves short peptide sequences which bind to the importin-α protein, and these usually contain highly basic sequences such as KRK/RR (SEQ ID NO: 101), P/RXXKRXK/R (SEQ ID NO: 102), or P/RXXKRK/R (SEQ ID NO: 103). There are two such binding sites on importin-α, and two basic sequences, separated by at least 10 amino acids can make up a bipartite NLS, such as the KRSAEGSNPPKPLKKLR NLS (SEQ ID NO:64) of the retinoblastoma protein. The second most characterized pathway involves proteins which bind specifically to the importin-β1 protein. Two proteins that use this method are the HIV-TAT and HIV-REV proteins, which use the sequences RKKRRQRRR (SEQ ID NO:7) and RQARRNRRRRWR (SEQ ID NO:13) respectively to bind directly to importin-β1 and induce nuclear import of the proteins.

In some embodiments, the NLS comprises, consists essentially of, or consists of the amino acid sequence of KR(K/R), (P/R)XXKRX(K/R) (SEQ ID NO: 105), or (P/R)XXKR(K/R) (SEQ ID NO: 103). In some embodiments, the NLS comprises, consists essentially of, or consists of the amino acid sequence PKKKRKV (SEQ ID NO:5), PAAKRVKLD (SEQ ID NO:6), GKKQYKLKH (SEQ ID NO:8), KRSAEGSNPPKPLKKLR (SEQ ID NO:9), RKKRRQRRR (SEQ ID NO:7) or RQARRNRRRRWR (SEQ ID NO: 13). In some embodiments, the NLS comprises, consists essentially of, or consists of the d-amino acid (inverso) sequence of KR(K/R), (P/R)XXKRX(K/R) (SEQ ID NO: 105), or (P/R)XXKR(K/R). In some embodiments, the NLS comprises, consists essentially of, or consists of the d-amino acid (inverso) sequence of PKKKRKV (SEQ ID NO:5), PAAKRVKLD (SEQ ID NO:6), GKKQYKLKH (SEQ ID NO:8), KRSAEGSNPPKPLKKLR (SEQ ID NO:9), RKKRRQRRR (SEQ ID NO:7) or RQARRNRRRRWR (SEQ ID NO: 13). In some embodiments, the NLS comprises, consists essentially of, or consists of the inverted d-amino acid (inverso) sequence of (K/R)RK, (K/R)XRKXX(P/R) (SEQ ID NO: 104), or (K/R)RKXX(P/R) (SEQ ID NO: 108). In some embodiments, the NLS comprises, consists essentially of, or consists of the reversed l-amino acid (retro) sequence of VKRKKKP (SEQ ID NO: 14), DLKVRKAAP (SEQ ID NO:15), HKLKYQKKG (SEQ ID NO:16), KRSAEGSNPPKPLKKLR (SEQ ID NO:9), RLKKLPKPPNSGEASRK (SEQ ID NO:65), RRRQRRKKR (SEQ ID NO: 19), or RWRRRRNRRAQR (SEQ ID NO:20). In some embodiments, the NLS comprises, consists essentially of, or consists of the reversed d-amino acid (retro-inverso) sequence of (K/R)RK, (K/R)XRKXX(P/R) (SEQ ID NO: 104), or (K/R)RKXX(P/R) (SEQ ID NO: 108). In some embodiments, the NLS comprises, consists essentially of, or consists of the reversed d-amino acid (retro-inverso) sequence of VKRKKKP (SEQ ID NO: 14), DLKVRKAAP (SEQ ID NO: 15), HKLKYQKKG (SEQ ID NO:16), KRSAEGSNPPKPLKKLR (SEQ ID NO:9), RLKKLPKPPNSGEASRK (SEQ ID NO:65), RRRQRRKKR (SEQ ID NO: 19), or RWRRRRNRRAQR (SEQ ID NO:20).

In some embodiments the NLS contains the l-amino acids mentioned above, with one or more of said amino acids N-methylated on the peptide nitrogen, or C-methylated on the α-carbon atom, or one or more d-amino acids.

C. CPP

Cell penetrating peptides (CPP) are peptide sequences which induce absorption of a linked protein or peptide through the plasma membrane of a cell. Exemplary cell permeable peptides include, but are not limited to, transportan (GWTLNSAGYLLGKINLKALAALAKKIL (SEQ ID NO:21)), PEP-1 (KETWWETWWTEWSQPKKKRKV (SEQ ID NO:22)), MPG (GLAFLGFLGAAGSTM-GAWSQPKKKRKV (SEQ ID NO:23)), p-VEC (LLIILRR-RIRKQAHAHSK (SEQ ID NO:24)), MAP (KLALKLAL-KALKAALKLA (SEQ ID NO:25)), CADY (GLWRALWRLLRSLWRLLWRA (SEQ ID NO:26)), polyR (R6-R12), HIV-TAT 49-57(8) (RKKRRQRRR(SEQ ID NO:7)(G)), HIV-REV 35-46 RQARRNRRRRWR (SEQ ID NO: 13), Penetratin (RQIKIWFQNRRMKWKK (SEQ ID NO:27)), R6W3 (RRWWRRWRR (SEQ ID NO:28)), P22N (NAKTRRHERRRKLAIER (SEQ ID NO:29)), DPV3 (RKKRRRESRKKRRRES (SEQ ID NO:30)), DPV6 (GRPRESGKKRKRKRLKP (SEQ ID NO:31)), K-FGF (AAVLLPVLLAAP (SEQ ID NO:32)) or C105Y (CSIPPE-VKFNKPFVYLI (SEQ ID NO:33)). Additional CPP are reviewed in Arjen van den Berg and Steven F Dowdy (Current Opinion in Biotechnology 2011, 22:888-893 and Farkhani et al. (Peptides 57 (2014) 78-94); each of which is herein incorporated by reference in its entirety).

Generally, CPPs induce entry into the cell because of their general shape, and tendency to either self assemble into membrane-spanning pore, or to have several positively charged residues, which interact with the negatively charged phospholipid outer membrane inducing curvature of the membrane, which in turn activates various forms of internalization. As the interactions do not generally require high affinity interactions with cell surface proteins, they tend to be sensitive to both shape and charge distribution, but not to chirality. Thus, as with the NLS, both retro and inverso peptides, as well as retro-inverso peptides are suitable for use as CPP.

It should be noted that the NLS sequences and the CPP sequences of the HIV-TAT and HIV-REV proteins are identical, and only 9 and 12 amino acids long respectively. Therefore, these two peptides are examples of sequences that have both NLS and CPP functions.

D. PSTM

Prostatic cells have several abundantly expressed cell surface antigens which are almost exclusively expressed in the prostate. Furthermore, several of these proteins increase their expression in prostatic tumors, often with the upregulation and the progression of the disease being positively correlated, and such proteins can be targeted by the PSTMs of the disclosure. Highly prostate-selective antigens include, but are not limited to, Folate Hydrolase 1 (FOLH1, previously known as Prostate-Specific Membrane Antigen); PSMA, and also known as Glutamoyl Carboxypeptidase II GCPII, Prostate Stem Cell Antigen, PSCA; Epithelial Cell Adhesion Molecule, EpCAM; Luteinizing Hormone-Releasing Hormone Receptor, LHRHR; and Gastrin-Releasing Peptide Receptor, GRPR. Other, prostate-specific targeting antigens include, but are not limited to, the ErbB2 receptor, the urokinase receptor, uPAR and Mucin 1, Mucl. Some proteins, mainly expressed on tumor vascular epithelium such as the $\alpha_v\beta3$ integrin and Epidermal growth Factor-Like 7, EGFL7 can also be used as PSTM targets. For a review See e.g., Barve et al. (Journal of Controlled Release 187 (2014) 118-132); herein incorporated by reference in its entirety.

PSTMs can be monoclonal antibodies, or stable antibody fragments directed towards the cell surface antigens discussed above. Alternatively, they can be small molecule moieties with a high affinity for one of the prostatic antigens. In some embodiments, FOLH1 is used, as subnanomolar inhibitors based on simple glutamoyl ureas are described, and the enzyme also acts as a folate transporter, and is readily endocytosed. Another targeting moiety is GRPR, where radiopharmaceuticals based on the Bombesin 7-14 fragment, QWAVGHLM (SEQ ID NO:66)-NH$_2$, have been shown to produce (sub)nanomolar GRPR ligands, and considerable work has been done on stabilizing this peptide against proteolytic degradation. The LHRH receptor is also a very attractive target, as it has already been widely exploited for the anti-androgenic effects of both its agonists and antagonists, LHRH is a decapeptide pyro-EHWSYGL-RPG (SEQ ID NO:67)-NH$_2$, and replacement of $^6$G by d-K, one has a moiety to which one can conjugate (cytotoxic) payloads onto the ε-amine of the lysine, whilst retaining low nM affinity for LHRHR, and providing an enormous increase in cytotoxicity to LHRHR-expressing tumor lines.

In some embodiments, the PSTM is a ligand (e.g., peptide ligand) for PSMA or an anti-PSMA specific antibody (e.g., KYLAYPDSVHIW (SEQ ID NO:68), WQPDTAHHWATL (SEQ ID NO:69) or other decribd in Barve et al., supra). Normally, PSMA is expressed on membranes of prostate epithelial cells, and its expression level is increased in prostate cancer cells. Many studies have reported that PSMA is overexpressed in nearly all prostate cancers, and notably in almost all tumor stages. In addition, its expression level increases with cancer progression. In prostate cancer (PCa), the expression level enhances with aggressiveness and recurrence of tumor. The expression level of higher-grade and androgen-independent tumors is highest in the metastatic state.

Although PSMA is expressed in some normal tissues, such as small intestine, proximal renal tubules and salivary glands, its expression level is 100 to 1000 fold higher in prostate cancer cells compared to normal tissues. In addition, the site of expression of PSMA in normal tissues is not exposed to direct blood circulation. As a result, the PSMA's interaction with PSMA-specific antibodies or other ligands in normal tissues can be ignored.

PSMA is also expressed on the neovasculature of most solid malignant tumors, but not in normal vasculature. PSMA expression has been demonstrated in the tumor neovasculature of Glioblastoma Multiforme (GBM) by immunohistochemical staining. Strong reactivity to the antibody component of PSMA ADC (Antibody Drug Conjugate, Progenics Pharmaceuticals) was observed in the endothelial cells of new tumor blood vessels in GBM.

Several clinical studies targeting PSMA against a variety of cancers (e.g., prostate cancer, advanced prostate cancer, glioblastoma, hepatocellular carcinoma, and renal cell carcinoma) are underway (See e.g., the web site of the National Institutes of health).

In some embodiments, PSTMs are used as one of the components of the compositions described herein and are covalently bonded to the remainder of the entity, or connected to a nanostructural, in order to target it. For example, in some embodiments where the nanostructure is a liposome, filled with the EIP-NLS-CPP therapeutic moiety, the PSTM is a bombesin 7-14 analogue, anchored into the liposome by a covalently attached lipid tail. In some embodiments comprising compounds bound to dendrimers, PSTMs are directly bonded to one or more of the available amines on the dendrimer surface. In some embodiments, where the nanostructure is a micelle built from a PEG-PAA block copolymer or similar material, a portion (e.g., approximately 10%) of PSTM PEG-PAA copolymer is included.

In some embodiments, for example, in compounds for treating Ewing's sarcoma, and various leukemias, targeting to tissues other than prostate is utilized. STEAPI has been shown to be overexpressed on both Ewing's sarcoma and various leukemias, all of which may be driven by ERG-family transcription factors (Biochem Biophys Res Comm 429, 148 (2012)). Thus STEAP1-targeted agents find use in targeting prostate cancer, Ewing's Sarcoma, and various leukemias.

E. Nanostructure

In some embodiments, the therapeutic targeting component comprising a EIP and one or more of the above described components is further modified with a nanostructure. Examples include, but are not limited to, liposomes and micelles, as well as large polyethylene glycol (PEG) oligomers, which may carry one or more molecules of the therapeutic covalently bonded to the PEG core. Drug molecules may also be attached to dendrimers of various sizes. The nanostructures accumulate selectively in the tumor, without specific molecular interactions to retain them due to the leaky nature of tumor vasculature, which tends to have very poor tight endothelial junctions, allowing such moieties to penetrate selectively into tumors. This is referred to as Enhanced Penetration and Retention, or EPR. In such embodiments, the nanostructure itself acts as the PSTM in patients with prostate cancer. However, in some embodiments, the moieties are actively targeted to prostatic and/or tumor tissues by the use of PSTMs (e.g., those described herein) on the surface of the nanostructure. This includes, but is not limited to antibodies, or antibody fragments, specific for a prostate/tumor selective antigen such as PSMA, PSCA, LHRHR, GRPR, peptides that bind strongly to receptors such as LHRHR and GRPR, and small molecules that bind tightly to one of the desired antigens, such as the glutamoyl ureas known to be potent PSMA ligands. In some embodiments, ligands are directly bonded to the carrier moiety, for example with dendrimers, or bonded to an entity that allows it to be exposed on the surface of a lipid-containing molecule such as a liposome micelle or loaded lipoprotein. For example, in some embodiments, the PSTM is linked to a phospholipid or to cholesterol, and then incorporated in the outer layer of the lipidic nanostructure. In some embodiments, there is a direct linkage between PSTM and lipid, or they are linked via a linker such as a small peptide, or PEG.

F. Linker Entity (LE)

In some embodiments, linkers are used to join the PSTM to the rest of the peptide. The prostate specific targeting moiety, PSTM, may be coupled to CPP-NLS-EIP portion of compound (1) via a variety of linkages, depending on its nature. In embodiments where the targeting moieties are peptide ligands for peptide receptors, they are attached by further peptide bonds on one end of the CPP-NLS-EIP moiety, or in the middle of it, provided none of the 3 extant domains is interfered with functionally. In some embodiments, where the PSTM is of a different peptide orientation to the peptide(s) it is attached to (e.g., d or l-amino acid), a malonic acid or diamine is introduced to compensate for the differing orientations of the peptide chains, using the diamines and diacids described herein. In some embodiments, if the PSTM ligand is not peptidic, but contains either a primary amine or a carboxylic acid, or can be linked via a linker L which terminates in a primary amine or carboxylic acid, it is attached to the appropriate end of the peptide composition by formation of one more peptidic bond. Alternatively, such a PSTM is attached to the peptide chain via formation of an amide bond to an internally placed lysine, aspartic acid or glutamic acid, provided that branching at that position does not interfere with the functionality of that module in the peptide portion.

In some embodiments, nonpeptide PSTM modules are be covalently linked via a linker to the core peptide in a variety of other ways. The following examples are not exclusive. Example include, but are not limited to, reductive amination to attach the PSTM to a lysine, alkylation of cysteine to form a thioether, and O-alkylation of serine, threonine and tyrosine to form ethers, and N-alkylation of arginine and histitidine.

In some embodiments, the linker is a small alkyl/acyl chain, optionally substituted, which either alkylates or acylates a heteroatom in a side chain of one of the core peptide residues. Alternatively, if the linker terminates in a carboxylic acid, or a primary or secondary amine, it is connected to the appropriate end of the core peptide by a peptide bond. In some circumstances, it may be advantageous to cleave the PSTM or other component once in the pericellular or intracellular environment, in which case the linker can be a cleavalble linker entity, as described below.

In some embodiments, (e.g., if the compound is covalently bonded to the nanostructure or delivered by a macromolecular entity), a linker or linker entity is utilized. For example, in some embodiments, linkers are selectively cleavable either in close proximity to tumor cells, or after the entire entity has been absorbed into a (tumor) cell. In some embodiments, linker entities are peptides (or other forms of chemical bond) that are stable in normal circulatory conditions, but are cleaved selectively in the tumor environment or after cellular internalization. For example, in some embodiments, the linker is a peptide sequence such as HSSKLQL (SEQ ID NO:62), which is known to be selectively cleaved by PSA or comprises an acid sensitive linker such as an acylhydrazone, which allows it to be released in the acidic tumor microenvironment, or in acidic endosomes after internalization. In some embodiments, the linker is a hypoxia-sensitive 4-nitro-3-alkylbenzyloxy linker or a p-nitrobenzaldehyde acetal or a 1-acyloxy-3-(2-nitro-3,N-alkylimidaz-5-yl)propane, all of which is readily hydrolytically cleaved after reduction of the nitro group to a free amine in the in a hypoxic cellular environment In some embodiments, linker entities are cleaved in the peri-tumoral space, to release the compound in close proximity to the tumor, or the whole structure might be internalized, in which case the compounds are cleaved in the cell, prior to nuclear transportation. The LE may be cleaved in proximity to tumor cells by exploiting unusual conditions in the tumor's extracellular environment. In the case of targeting prostate tumors and their metastases, one can exploit the local high concentrations of the protease PSA, which generally either circulates as an inactive zymogen, or is rapidly deactivated by an irreversible reaction with one of the many protease inhibitors in circulation, with the result that active PSA is only present in the close vicinity of tumors. The sequence HSSKLQL (SEQ ID NO:62) is known to be readily cleaved by PSA. Tumors are more acidic than normal tissues, in part due to their high lactic acid output from relying heavily on glycolysis rather than oxidative phosphorylation for most of their ATP. In some embodiments, acid sensitive moieties such as acetals, isatin imines and acyl hydrazones cause greater drug release in the extracellular space in the tumor, or in tumor endosomes after internalization. Other forms of LE that cleaved intracellularly include hypoxia-sensitive linkers and disulfides. Hypoxia-activated prodrugs are activated selectively in tumors, where the tumor core tends to be highly hypoxic, allowing rapid reduction of functional groups which would normally not be appreciably metabolized in the tissues. Usually reduction of a nitro, N-oxide or quinone moiety to an amine, azine or quinol, leads to activation of a pendant electrophile, and the compounds then act as tumor selective alkylating agents. However, such reductions are also used to labilize a chemical linker, for example 4-nitrobenzyl ethers or acetals, which as 4-amino species become very hydrolytically labile. In some embodiments, diaryl disulfides, or hindered alkyl disulfides are used for intracellular cleavage, where glutathione levels are much higher, and several disulfide isomerases are present.

In some embodiments, linkers are non-covalent. For example, in some embodiments, a lipidic side chain, such as a palmitic acid group or a cholesterol molecule, is placed at one terminus of the compound in order to allow it to adhere to a liposomal carrier or lipoprotein carrier. In some embodiments, a nucleic acid sequences is used as a linker.

In some embodiments, linkages between the PSTM and the core peptide are cleavable linker entities (e.g., where it is advantageous not to have the PSTM moiety still attached when the compound enters the nucleus).

III. Therapeutic Applications

In some embodiments, the present disclosure provides therapies for cancer (e.g., prostate cancer, Ewing sarcoma, and leukemias). In some embodiments, therapies directly or indirectly target gene fusions or oncogenic ETS family member polypeptides (e.g., ERG, ETV1, ETS1).

The present disclosure is not limited to the treatment of a particular cancer. Embodiments of the present disclosure provide compositions and methods for treating cancers that express oncogenic ETS family members (e.g., ERG). In some embodiments, the cancer is prostate cancer or Ewing sarcoma or leukemias, although other cancers are specifically contemplated.

Ets-related gene (ERG) is a member of the ETS transcription factor gene family. Truncated forms of ERG are associated with multiple cancers such as Ewing's sarcoma, prostate cancer, and leukemia as part of oncogenic fusion translocations. Increased expression of ERG is highly indicative of poor prognosis in acute myeloid leukemia and ERG is expressed in acute megakaryoblastic leukemia (AMKL).

ERG has been associated with multiple cancers (Salek-Ardakani S, et al. ERG Is a Megakaryocytic Oncogene. Cancer Res Jun. 1, 2009 69; 4665; Yi H, et al. Inhibition of apoptosis by normal and aberrant Fli-1 and erg proteins involved in human solid tumors and leukemias. Oncogene. 1997 Mar. 20; 14(11): 1259-68).

For example, Ewing Sarcoma is frequently driven by EWS-ETS fusions (Karosas A O, et al. Ewing's sarcoma. Am J Health Syst Pharm. 2010 Oct. 1; 67(19):1599-605; Jedlicka P, et al. Ewing Sarcoma, an enigmatic malignancy of likely progenitor cell origin, driven by transcription factor oncogenic fusions. Int J Clin Exp Pathol. 2010 Mar. 19; 3(4):338-47).

Further, in acute myelogenous leukemia, the NH2-terminal region of TLS (translocation liposarcoma) is fused to the COOH-terminal domain of ERG through a recurrent t(16; 21) translocation. The resultant TLS-ERG fusion protein is associated with poor clinical outcome. TLS-ERG fusion is the primary genetic event leading to cellular transformation in acute myelogenous leukemia patients harboring t(16,21) translocation (See e.g., Pan, et al., Mol Cancer Res 2008; 6(5):862-72).

In addition, the oncogenic TLS-ERG fusion protein is found in human myeloid leukemia and Ewing's sarcoma (Junhui Zou, et al., MOLECULAR AND CELLULAR BIOLOGY, July 2005, p. 6235-6246; Pereira D S, et al., Proc Natl Acad Sci USA. 1998 Jul. 7; 95(14):8239-44).

E. Pharmaceutical Compositions

The present disclosure further provides pharmaceutical compositions (e.g., comprising pharmaceutical agents that modulate the expression or activity of gene fusions of the present disclosure). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. A continuous delivery of the drug for a longer period of time is achieved by formulating the drug in, for example, a polymer or other device that releases drug constantly at the tumor(s) site(s).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, including intravenous, intramuscular and subcutaneous, or intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, micelle and liposome-containing formulations. These compositions may be generated from a variety of components that include, but are not limited to, preformed liquids, self-emulsifying solids and self-emulsifying semisolids. In some embodiments, compounds are formulated as extended release compounds (e.g., in a polymer base for injection).

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, sterile parenteral solutions, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present disclosure the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the disclosure provide pharmaceutical compositions containing (a) one or more therapeutic agents and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the disclosure. Other chemotherapeutic agents are also within the scope of this disclosure. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

F. Combination Therapy

In some embodiments, the present disclosure provides therapeutic methods comprising one or more compositions described herein in combination with an additional agent (e.g., a chemotherapeutic agent). The present disclosure is not limited to a particular chemotherapy agent.

Various classes of antineoplastic (e.g., anticancer) agents are contemplated for use in certain embodiments of the present disclosure. Anticancer agents suitable for use with embodiments of the present disclosure include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of embodiments of the present disclosure include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE) or ubiquitination or neddylation inhibitors; 19) inhibitors of acetylation and/or methylation (e.g., HDAC inhibitors)) and inhibitors of bromodomain containing proteins (e.g. BET-BRD inhibitors); 20) modulators of NF kappa B; 21) inhibitors of cell cycle regulation (e.g., CDK inhibitors); 22) modulators of p53 protein function; 22) bromodomain inhibitors, and 24) radiation.

Any oncolytic agent that is routinely used in a cancer therapy context finds use in the compositions and methods of embodiments of the present disclosure. For example, the U.S. Food and Drug Administration maintains a formulary of oncolytic agents approved for use in the United States. International counterpart agencies to the U.S.F.D.A. maintain similar formularies. The below Table provides a list of exemplary antineoplastic agents approved for use in the U.S.

Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |

-continued

| | | |
|---|---|---|
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)[6], Azgly[10]]LHRH; pyro-Glu-His-Trp-Ser-Tyr-D-Ser(But)-Leu-Arg-Pro-Azgly-NH2 acetate [$C_{59}H_{84}N_{18}O_{14} \cdot (C_2H_4O_2)_x$] | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |

| | | |
|---|---|---|
| Ifosfamide<br>(3-(2-chloroethyl)-2-[(2-chloroethyl)amino]tetrahydro-<br>2H-1,3,2-oxazaphosphorine 2-oxide) | IFEX | Bristol-Myers Squibb |
| Imatinib Mesilate<br>(4-[(4-Methyl-1-piperazinyl)methyl]-N-[4-methyl-3-[[4-<br>(3-pyridinyl)-2-pyrimidinyl]amino]-phenyl]benzamide<br>methanesulfonate) | Gleevec | Novartis AG, Basel,<br>Switzerland |
| Interferon alfa-2a<br>(recombinant peptide) | Roferon-A | Hoffmann-La Roche, Inc.,<br>Nutley, NJ |
| Interferon alfa-2b<br>(recombinant peptide) | Intron A (Lyophilized<br>Betaseron) | Schering AG, Berlin,<br>Germany |
| Irinotecan HCl<br>((4S)-4,11-diethyl-4-hydroxy-9-[(4-<br>piperi-dinopiperidino)carbonyloxy]-1H-pyrano[3',4':<br>6,7] indolizino[1,2-b] quinoline-3,14(4H,12H)<br>dione hydrochloride trihydrate) | Camptosar | Pharmacia & Upjohn<br>Company |
| Letrozole<br>(4,4'-(1H-1,2,4-Triazol-1-ylmethylene) dibenzonitrile) | Femara | Novartis |
| Leucovorin<br>(L-Glutamic acid, N[4[[(2amino-5-formyl1,4,5,6,7,8<br>hexahydro4oxo6-pteridinyl)methyl]amino]benzoyl],<br>calcium salt (1:1)) | Wellcovorin, Leucovorin | Immunex, Corp., Seattle, WA |
| Levamisole HCl<br>((−)-(S)-2,3,5,6-tetrahydro-6-phenylimidazo [2,1-b]<br>thiazole monohydrochloride $C_{11}H_{12}N_2S \cdot HCl$) | Ergamisol | Janssen Research Foundation,<br>Titusville, NJ |
| Lomustine<br>(1-(2-chloro-ethyl)-3-cyclohexyl-1-nitrosourea) | CeeNU | Bristol-Myers Squibb |
| Mechlorethamine, nitrogen mustard<br>(2-chloro-N-(2-chloroethyl)-N-methylethanamine<br>hydrochloride) | Mustargen | Merck |
| Megestrol acetate<br>17α(acetyloxy)-6-methylpregna-4,6-diene-3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6 H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-<br>pteridinyl)methyl]methylamino]benzoyl]-L-glutamic<br>acid) | Methotrexate | Lederle Laboratories |
| Methoxsalen<br>(9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane<br>(1,1-dichloro-2-(o-chlorophenyl)-2-(p-chlorophenyl)<br>ethane) | Lysodren | Bristol-Myers Squibb |
| Mitoxantrone<br>(1,4-dihydroxy-5,8-bis[[2-[(2-<br>hydroxyethyl)amino]ethyl]amino]-9,10-anthracenedione<br>dihydrochloride) | Novantrone | Immunex Corporation |
| Nandrolone phenpropionate | Durabolin-50 | Organon, Inc., West Orange,<br>NJ |
| Nofetumomab | Verluma | Boehringer Ingelheim Pharma<br>KG, Germany |
| Oprelvekin<br>(IL-11) | Neumega | Genetics Institute, Inc.,<br>Alexandria, VA |
| Oxaliplatin<br>(cis-[(1R,2R)-1,2-cyclohexanediamine-N,N']<br>[oxalato(2-)-O,O'] platinum) | Eloxatin | Sanofi Synthelabo, Inc., NY, NY |
| Paclitaxel<br>(5β,20-Epoxy-1,2a,4,7β,10β,13a-hexahydroxytax-11-<br>en-9-one 4,10-diacetate 2-benzoate 13-ester with (2R,3S)-<br>N-benzoyl-3-phenylisoserine) | TAXOL | Bristol-Myers Squibb |
| Pamidronate<br>(phosphonic acid (3-amino-1-hydroxypropylidene) bis-,<br>disodium salt, pentahydrate, (APD)) | Aredia | Novartis |
| Pegademase<br>((monomethoxypolyethylene glycol succinimidyl) 11-17-<br>adenosine deaminase) | Adagen (Pegademase<br>Bovine) | Enzon Pharmaceuticals, Inc.,<br>Bridgewater, NJ |
| Pegaspargase<br>(monomethoxypolyethylene glycol succinimidyl<br>L-asparaginase) | Oncaspar | Enzon |
| Pegfilgrastim<br>(covalent conjugate of recombinant methionyl human G-<br>CSF (Filgrastim) and monomethoxypolyethylene glycol) | Neulasta | Amgen, Inc |

-continued

| | | |
|---|---|---|
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

IV. Drug Screening Applications

In some embodiments, the present disclosure provides drug screening assays (e.g., to screen for anticancer drugs). The screening methods of the present disclosure utilize gene fusions described herein.

In some embodiments, the present disclosure provides methods (e.g., high-throughput methods) for screening peptides (e.g., those disclosed herein), peptide derivates, peptide mimetics, and small molecules for the ability to alter gene fusion (e.g., ERG gene fusion) biological activity. In some embodiments, small molecule candidate compounds are identified based on the crystal structures of ERG-peptide interactions and interact with residues of ERG that are shown to be involved in binding to peptides.

Embodiments of the present disclosure provides screening methods for identifying modulators, i.e., candidate or test compounds or agents (e.g., proteins, peptides, peptidomimetics, peptoids, small molecules or other drugs) which bind to gene fusions, have an inhibitory (or stimulatory) effect on, for example, gene fusion expression or gene fusion activity, or have a stimulatory or inhibitory effect on, for example, the expression or activity of a gene fusion substrate. Compounds thus identified can be used to modulate the activity of target gene products (e.g., gene fusions) either directly or indirectly in a therapeutic protocol, to elaborate the biological function of the target gene product, or to identify compounds that disrupt normal target gene interactions. Compounds that inhibit the activity or expression of gene fusions are useful in the treatment of proliferative disorders, e.g., cancer, particularly prostate cancer, Ewing sarcoma, and leukemias.

In one embodiment, the disclosure provides assays for screening candidate or test compounds that are substrates of a gene fusion protein or polypeptide or a biologically active portion thereof. In another embodiment, the disclosure provides assays for screening candidate or test compounds that bind to or modulate the activity of a gene fusion protein or polypeptide or a biologically active portion thereof.

EXPERIMENTAL

The following examples are provided in order to demonstrate and further illustrate certain preferred embodiments and aspects of the present disclosure and are not to be construed as limiting the scope thereof.

Example 1

Materials and Methods
Cell Lines

PC3 (ATCC) and DU145 (ATCC) prostate cancer cell lines were grown in RPMI 1640 (Invitrogen) and VCaP (ATCC) cells in DMEM with Glutamax (Invitrogen), all supplemented with 10% FBS (Invitrogen) and cultured in 5% $CO_2$ incubator. The immortalized prostate cell line RWPE1-1 (ATCC) was grown in Keratinocyte media with the supplements (Invitrogen). All cultures were also maintained in 50 units/ml of penicillin/streptomycin (Invitrogen). The genetic identity of cell lines was determined as previously described (Sherman et al., 2007).

Basement Membrane Matrix Invasion Assays

For invasion assays, the cell lines were treated with the peptidomimetics or negative controls for 24 hours prior to harvesting and then seeded onto the basement membrane matrix (Chemicon, Temecula, Calif.) in the chamber insert with 8.0 m pores in a 24-well culture plate in serum free media. Complete media was added to the lower chamber as a chemoattractant. After 48 hours incubation at 37° C. in 5% $CO_2$, the non-invading cells and EC matrix were gently removed with a cotton swab. Invasive cells, located on the lower side of the membranes, were stained with crystal violet, air dried and photographed. To quantify the relative number of invaded cells, colorimetric assays were performed by treating the inserts with 150 μl of 10% acetic acid (v/v) and measuring absorbance of each sample in a spectrophotometer at 560 nm (GE Healthcare).

Gene Expression Array Analysis

Expression profiling was performed using the Agilent Whole Human Genome Oligo Microarray (SantaClara, Calif.) according to the manufacturer's protocol. All samples were run in biological duplicate against control. The microarray data were preprocessed and normalized using the R package limma as described (Smyth, Stat Appl Genet Mol Biol 3, Article3 2004). Gene Set Enrichment Analysis (GSEA) for gene signatures was performed using the JAVA program as described (Subramanian et al., Proc Natl Acad Sci USA 102, 15545-15550 2005).

VCaP cells were treated with 50 μM peptides for 12 hours, and total RNA extracted using RNeasy Mini Kit (Qiagen) for gene expression array analysis. Expression profiling was performed using the Agilent Whole Human Genome Oligo Microarray (SantaClara, Calif.) according to the manufacturer's protocol. All samples were run in biological quadruplets along with controls. The microarray data were preprocessed and normalized using the R package limma as described (Smyth, 2004, supra). Over- and under-expressed gene sets were generated by filtering to include only 2-fold average over- or under-expression (FDR<0.01) in all hybridizations. Fisher's exact test was applied to compare the significance of overlaps among the up- or down-regulated genes in siERG and peptide-treated VCaP cells. Gene Set Enrichment Analysis (GSEA) for those gene signatures was performed using the JAVA program as described (Subramanian et al., 2005; supra).

ChIP-Seq and Computational Analysis

The ChIP assays for ERG were performed using HighCell ChIP kit (Diagenode) according to manufacturer's protocol. Short reads were aligned to the HG19 reference using Bowtie2 (Subramanian et al., 2005; supra) with all default settings. Duplicate fragments (based on the coordinates of both reads) and fragments where only one read was successfully mapped were removed using SamTools (Li et al., Bioinformatics 25, 2078-2079 2009).

ChIP assays for ERG were performed using HighCell ChIP kit (Diagenode) according to manufacturer's protocol. For ERG ChIP-seq studies, VCaP cells were treated with 50 μM RI-EIP1 or RI-muEIP1 for 12 hours and then cross-linked with 1% formaldehyde for 10 minutes. Crosslinking was terminated by the addition of 1/10 volume 1.25 M glycine for 5 min at room temperature followed by cell lysis and sonication (Bioruptor, Diagenode), resulting in an average chromatin fragment size of 200 bp. Chromatin equivalent to 5×106 cells were used for ChIP assays using various antibodies. ChIP DNA was isolated (IPure Kit, Diagenode) from samples by incubation with the antibody at 4° C. overnight followed by wash and reversal of cross-linking.

The ChIP-seq sample preparation for sequencing was performed according to the manufacturer's instructions (Illumina). ChIPenriched DNA samples (1-10 ng) were converted to blunt-ended fragments using T4 DNA polymerase, E. coli DNA polymerase I large fragment (Klenow polymerase) and T4 polynuleotide kinase (New England BioLabs, NEB). A single A-base was added to fragment ends by Klenow fragment (3' to 5' exon minus; NEB) followed by ligation of Illumina adaptors (Quick ligase, NEB). The adaptor-modified DNA fragments were amplified by PCR using the Illumina Barcode primers and Phusion DNA polymerase (NEB). PCR products were size-selected using 3% NuSieve agarose gels (Lonza) followed by gel extraction using QIAEX II reagents (QIAGEN). Libraries were quantified with the Bioanalyzer 2100 (Agilent) and sequenced on the Illumina HiSeq 2000 Sequencer (100 nucleotide read length).

Chicken CAM and Angiogenesis Studies

The CAM assay was performed as described previously (Brenner et al., Cancer Cell 19, 664-678 2011). Angiogenesis assays were performed essentially as described previously (Hood et al., 2003). Filter discs saturated with 1.5 mg peptides along with 5 mg/ml VEGF were placed on top of the 10 days old chicken embryo CAM. Retinoic acid (2 mg/ml), a known inhibitor of angiogenesis, was used as positive control. After 72 hours, filter discs and associated CAM tissues were harvested and quantified. Angiogenesis was assessed as the number of visible blood vessel branch points within the defined area of the filter discs.

Xenograft Mouse Models

Athymic Nude-Foxnlnu male mice were procured from Harlan Laboratories, Inc (Indianapolis, Ind.). All procedures involving mice were approved by the University Committee on Use and Care of Animals (UCUCA) at the University of Michigan and conformed to their relevant regulatory standards. Survival was calculated using a cutoff tumor volume of 1,500 mm$^3$ as a surrogate for mortality according to the approved animal protocol. Statistical significance for Kaplan-Meier analysis was determined by the log-rank (Mantel-Cox) test.

Athymic Nude-Foxnlnu male mice were procured from Harlan Laboratories, Inc. (Indianapolis, Ind.). VCaP ($2\times10^6$ cells) or PC3 ($5\times10^5$ cells) were resuspended in 100 µl of saline with 50% Matrigel (BD Biosciences, Becton Drive, NJ) and implanted subcutaneously into the flank regions on both sides of the mice. Mice were anesthetized using a cocktail of xylazine (80-120 mg/kg, IP) and ketamine (10 mg/kg, IP) for chemical restraint before tumor cells implantation. For short term assays, all tumors were staged for three weeks before starting peptidomimetic treatment. After week 3 (VCaP cells) or 12 days (PC3 cells), mice (10 per treatment group) were treated with peptidomimetics (25 mg/kg or 10 mg/kg as indicated, IP) daily five times a week.

Tumor growth was recorded every three days using digital calipers and tumor volumes were calculated using the formula $(\pi/6)(L\times W2)$, where L=length of tumor and W=width. Body weight was monitored weekly over the course of the study. At the end of the xenograft studies, mice were anaesthetized and blood was collected by cardiac puncture and tumors were preserved for further biochemical and immunofluorescence analysis. Supernatant containing serum was separated by incubating blood on ice for 45 min, followed by centrifugation at 8000 rpm for 10 min at 4° C. Survival was calculated using a cutoff tumor volume of 1,500 mm3 as a surrogate for mortality according to the approved animal protocol. Survival analysis was carried out using the GraphPad Prism 4.0 software (GraphPad Software, San Diego, Calif.). Statistical significance for Kaplan-Meier analysis was determined by the log-rank (Mantel-Cox) test. All procedures involving mice were approved by the University Committee on Use and Care of Animals (UCUCA) at the University of Michigan and conform to their relevant regulatory standards.

Statistical Analysis

Statistical analysis was performed using Graphpad Prism 6 software. For individual comparisons, nonparametric Mann-Whitney test was used and $p<0.05$ was considered significant. On all plots and graphs the standard error of the mean is shown.

Protein Expression by Baculovirus and Purification

Baculovirus that express either ERG or GUS protein was constructed using the Bac-to-Bac Baculovirus Expression System (Invitrogen). Briefly, cDNAs encoding full-length ERG and GUS were cloned into pDEST10 vector (Invitrogen) and transferred to FastBac vector (Invitrogen), which was used to make recombinant virus. Virus was then amplified following the manufacturer's protocol and used to infect SF9 cells. After 3 days post-infection, SF9 cells were harvested and lysed (50 mM Tris [pH 7.9], 150 mM NaCl, 1 mM MgCl$_2$, 0.5 mM EDTA, 1 mM DTT, 0.1% NP40) in the presence of protease inhibitors (Roche). Cell lysates were homogenized by three rounds of sonication (30 s each) on ice and supernatant was recovered by centrifuging at 11,000 rpm for 10 min. Recombinant His-tagged ERG and GUS proteins were purified using $Ni^{2+}$-NTA agarose (Invitrogen) following the manufacturer's protocol and the eluates were dialyzed against lysis buffer overnight at 4° C., and stored at −80° C. in 10% glycerol.

Enrichment of Phage Display Random Peptide Library

The Ph.D.-7 Phage Display Peptide Library (New England Biolabs) was used in biopanning experiments. This library contained 109 unique 7-mer peptides linked to the N-terminus of a phage coat protein by a 4 amino acid spacer (GGGS). Using this library, ERG-binding phage clones were selected by panning over immunotubes (Maxisorb, Nunc) coated with recombinant protein at 10 µg/ml. First, nonspecific clones were removed by pre-absorbing phage clones from the phage library using a GUS proteincoated immunotube for 1 hour at 4° C. ERG-binding phage clones were then enriched by panning the pre-cleared phage library over an ERG protein-coated immunotube for 2 hours at 4° C., eluted with glycine buffer (pH 2.2) and neutralized with Tris buffer (pH 9.0). DNA from eluates and neutralized phage clones was then amplified and precipitated for subsequent rounds of selection. A total of 4 rounds of selection were performed.

Reverse Phage ELISA

After screening the phage display library, phage clones were serially diluted, spread on to Luria-Bertani (LB) agar plates and grown overnight at 37° C. A total of 59 single colonies were randomly chosen and propagated into 96-well plates. As controls, 4 random clones from the original, unenriched phage library and one empty phage clone were also selected. ELISA assays were performed to confirm the interaction between each phage clone and ERG. Briefly, ELISA plates (Max-Sorb™, NUNC) were incubated overnight at 4° C. with either purified His-tagged ERG or GUS protein (10 µg/ml in carbonate buffer pH 9.6). Protein-coated ELISA plates were blocked (PBS with 5% BSA) for 1 hour at RT prior to incubation with expressed phage supernatant (diluted 1:10 in PBS with 1% BSA) for 2 hours at RT. The plates were then washed three times (PBS-0.1% Tween-20) and bound phage was detected with horseradish peroxidase-conjugated anti-M13 antibody (GE Healthcare) using the TMB substrate system (Sigma). Reactions were quenched using 250 mM HCl and absorbance was recorded on a SpectraMAX plate reader (OD 450 nm). DNA from phage clones was sequenced using the 96-gIII sequencing primer according to the manufacture's protocol.

Peptide Synthesis

Synthetic peptides (including biotin or FITC conjugated peptides) were custom-synthesized and HPLC-purified by AnaSpec (San Jose, Calif.). Peptides were stored lyophilized at −20° C. until reconstituted with sterile water immediately before use for both in vitro and in vivo experiments. HPLC-MS was used to confirm 95% or higher purity for each peptide.

In Vitro Transcription/Translation System

In vitro Halo fusion protein expression was achieved by cloning desired expression cassettes downstream of Halo loci (approximately 35 kDa). Briefly, ERG and ERG subdomains were cloned into pFN19A vector (Promega) following the manufacturer's instructions. Point mutations were then created in the Halo-ETS pFN19A expression vector using the Quikchange XL site directed mutagenesis kit (Stratagene). After cloning, Halo fusion proteins were expressed using the TNT® SP6 High-Yield Wheat Germ kit (Promega) following the manufacturer's protocol. For each reaction, protein expression was confirmed by incubating the cell-free reactions with biotin-linked Halo ligand and performing Western blot analysis using an HRP-streptavidin.

HaloLink Protein Array

Identification of the peptide binding site on ERG was achieved by creating a custom protein array of full length ERG and ERG subdomains that were used to capture ERG-binding phage clones. First, full length or individual domains of Halo-ERG fusions were synthesized and expression was confirmed by Western blot as described above. Expressed proteins were covalently immobilized on HaloLink Slides (Promega) in a humidity chamber for 1 hour at RT. Protein coated slides were then washed using PBS-I (1×PBS, 0.05% IGEPAL CA-630) to reduce non-specific binding interactions and incubated with ERG20 interacting phage clones (diluted in PBS-B: 1×PBS, 10 mg/ml BSA) in a humidity chamber for 1 hour at RT. After washing, slides were incubated with Cy3 labeled rabbit anti-M13 (GE Healthcare). In all cases, protein quantities were confirmed using an anti-HaloTag antibody. For peptide inhibition assays, the protein array was pre-incubated with the synthetic peptides for 1 hour prior to incubating with phage clones for an additional 1 hr at RT. The signal was detected using an Axon scanner and images were quantified using GenePix Pro 6 software (Molecular Devices).

ERG:Peptide Binding Assays

The interaction coefficients between ERG and synthetic peptides or peptidomimetics were determined by biolayer interferometry technology using the Octet Red system (ForteBio). Purified ERG and GUS proteins were biotinylated by EZLink NHS-PEG4 Biotinylation Kit (Thermo Scientific) following the manufacturer's protocol and any unincorporated biotin was removed from the reactions with Zeba 2 ml desalt columns (Thermo). Biotinylated proteins (500 µg/ml) were then incubated with super streptavidin biosensors in binding buffer (20 mM HEPES pH 7.4, 150 mM NaCl), blocked with 10 µg/ml biocytin and washed three times in binding buffer. Peptides were serially diluted in binding buffer, mixed with the protein-coupled biosensors and peptidomimetic:protein association/dissociation was monitored for 10 min at 25° C. Nonspecific binding from the signal obtained from peptidomimetic:GUS interactions was subtracted from that of peptidomimetic:ERG interactions and baseline signal drift was controlled by monitoring immobilized ERG without peptide. Octet Red analysis software was used to analyze the data.

Electrophoretic Mobility Shift Assay (EMSA)

To determine the inhibitory activity of the peptide against the ERG:DNA interaction, electrophoretic mobility shift assays (EMSAs) were performed. Double stranded ERG ETS binding sequence (5' GATCTTCGAAACGGAAGT-TCGAG 3' (SEQ ID NO:109)) was end labeled using Biotin 3' End DNA Labeling Kit (Pierce). For each binding reaction, VCaP cell extract was incubated with 1 µg poly d (I-C), 2 µl of EMSA binding buffer (1.5% glycerol, 75 mM KCl, 0.375 mM DTT, 12.5 mM NaCl, 0.375 mM phenylmethylsulfonyl fluoride [PMSF]) and 5 µM biotin-labeled EBS in the presence or absence of the peptides as indicated for 30 min at room temperature. The reaction mixtures were loaded onto 6% TBE gels (Invitrogen) and electrophoresed at 120 V for 2 hr at 4° C. in 0.5% Tris-Borate-EDTA (TBE). Probes were transferred to nylon membrane (Biodyne B, Pall) in a semidry blotting device at 300 mA for 30 min. The membrane was baked for 30 min at 85° C. in a dry oven. Biotinylated oligonucleotides were detected by probing with streptavidin-conjugated horseradish peroxidase and visualized by enhanced chemiluminescence (Pierce).

Cell Lines

PC3 (ATCC) and DU145 (ATCC) prostate cancer cell lines were grown in RPMI 1640 (Invitrogen) and VCaP (ATCC) cells in DMEM with Glutamax (Invitrogen), both supplemented with 10% FBS (Invitrogen) and cultured in 5% $CO_2$ incubator. The immortalized prostate cell line RWPE-1 (ATCC) was grown in Keratinocyte media with L-glutamine (Invitrogen) supplemented with 2.5 µg EGF (Invitrogen) and 25 mg Bovine Pituitary Extract (Invitrogen). All cultures were maintained with 50 units/ml of penicillin/streptomycin (Invitrogen). The genetic identity of cell lines was determined as previously described (Sherman et al., BMC Bioinformatics 8, 426. 2007). Virus and stable isogenic cell lines were derived as previously described (Brenner et al., 2011; supra).

Pull-Down Assays

Approximately 1 mg of soluble VCaP cell lysate prepared in RIPA buffer (Invitrogen) was incubated with varying amounts of biotinylated peptides for 2 hours at 4° C. HaloLink agarose beads (20 µl) were added to the peptide-lysate mixture and incubated for an additional 4 hours. Beads were then pelleted by centrifugation, washed three times in PBS-T and loaded into an SDSPAGE gel followed by Western blot analysis. Total VCaP cell lysate was loaded for positive control.

In Vitro Peptide Competitive Pull-Down Assay

Halo-ERG fusion protein was expressed using in vitro transcription/translation system as described above. After confirming protein expression, the Halo-ERG fusion protein was incubated with either 100 ng of GST-AR protein (Millipore) or 224 U (2 µl) of purified DNA-PKcs (Promega). Protein mixtures were incubated with or without the peptides in PBS-T (0.1% Tween) at 4° C. overnight. Simultaneously, HaloLink beads (Promega) were blocked in 5% BSA at 4° C. overnight. The next day 10 µl of HaloLink beads were mixed with the protein-peptide mixture, incubated at RT for 1 hour, washed with 4× in PBS-T and eluted into SDS sample buffer. Proteins were resolved on SDS gel electrophoresis followed by Western blot analysis with either anti-GST mAb (Sigma) or anti-DNA-PKcs (Santa Cruz, H-163) as described below. HaloLink beads without incubation with fusion proteins were used as negative controls.

Western Blot Analysis

VCaP cells were seeded in 6-well plates at $0.5 \times 10^6$ cells/ml and after allowing cells to attach, cells were harvested and homogenized in NP40 lysis buffer (Sigma)

containing a complete protease inhibitor cocktail (Roche). Ten micrograms of each protein extract was boiled in SDS sample buffer, size fractionated by SDS-PAGE, and transferred onto a PVDF membrane (GE Healthcare). After blocking in 5% nonfat dry milk, membranes were incubated with the following primary antibodies: anti-DNA-PKcs rabbit polyclonal (1:500, Santa Cruz, H-163), anti-ERG1/2/3 rabbit polyclonal (1:1000, Santa Cruz, C-17) or anti-AR monoclonal (1:1000, Millipore). Following three washes in TBS-T, the blots were incubated with horseradish peroxidase conjugated secondary antibody and the signals visualized by enhanced chemiluminescence system according to manufacturer's instructions (GE Healthcare).

Mass Spectrometry

The samples were treated with SDS loading buffer supplied with 10 mM DTT for 5 min at 85° C. The proteins were alkylated by adding iodoacetamide to the final concentration of 15 mM. The samples were subjected to SDS-PAGE and the whole lanes were cut out and digested with trypsin in-gel for 2 hours. The resulting peptides were extracted, dried and resuspended in 0.1% formic acid with 5% acetonitrile prior to loading onto a trap EASY-column (Thermo Scientific) coupled to an in-house made nano HPLC column (20 cm×75 um) packed with LUNA C18 media. Analysis was performed on Velos Pro mass spectrometer (Thermo Scientific) operated in data-dependent mode using 90-min gradients in EASY-LC system (Proxeon) with 95% water, 5% acetonitrile (ACN), 0.1% formic acid (FA) (solvent A), and 95% ACN, 5% water, 0.1% FA (solvent B) at a flow rate of 220 nl/min. The acquisition cycle consisted of a survey MS scan in the normal mode followed by twelve data-dependent MS/MS scans acquired in the rapid mode. Dynamic exclusion was used with the following parameters: exclusion size 500, repeat count 1, repeat duration 10s, exclusion time 45s. Target value was set at 104 for tandem MS scan. The precursor isolation window was set at 2m/z. The complete analysis comprised two independent biological replicates.

Mass Spectrometry Data Analysis

The resulting spectrum files were transformed into MGF format by MSConvert software and interrogated by MASCOT 2.4 search engine using human UniProt database version 15 concatenated with reverse sequences for estimation of false discovery rate (FDR) and with a list of common contaminants. The search parameters were as follows: full tryptic search, 2 allowed missed cleavages, peptide charges +2 and +3 only, MS tolerance 1 Da, MS/MS tolerance 0.5 Da. Permanent post-translational modifications was: cysteine carbamidomethylation. Variable post-translational modifications were: protein N-terminal acetylation, Met oxidation and N-terminal Glutamine to pyro-Glutamate conversion. The remaining analysis was performed as described (Poliakov et al., Molecular & cellular proteomics: MCP 10, M110 007039 2011). To summarize, the minimal ion score threshold was chosen such that a peptide false discovery rate (FDR) below 1% was achieved. The peptide FDR was calculated as 2×(decoy_hits)/(target+decoy hits). Spectral counts for all detected proteins were assembled using an in-house written Python script. The adjustment of spectral counts was done by the same script as described (Poliakov et al., 2011; supra).

Immunofluorescence Staining

VCaP cells were seeded in a 4-well chamber slide for 24 hours prior to the addition FITC-labeled peptide to a final concentration of 10 µM. After 2 hours incubation, cells were washed two times in PBS, and fixed for 15 min in 100% methanol. After washing an additional three times in PBS, cells were mounted using Vectashield with DAPI (Vector laboratories). Images were captured using 100× oil objective lens on an Olympus Confocal microscope at the University of Michigan microscopy imaging lab.

Co-Localization Staining

VCaP cells were seeded in a 8-well chamber slide for 24 hours prior to the addition FITC-labeled peptide to a final concentration of 1 M. After 6 hours incubation, cells were fixed in 4% paraformaldehyde, permeablized with PBS containing 0.1% triton×100, blocked in PBS containing 2% normal goat serum and stained with (1:200 dilution) of primary antibody and (1:400 dilution) of secondary antibody diluted in blocking solution. The following primary and secondary antibodies were used: mouse-anti-ERG (Biocare) and goat-anti-mouse-Cy5 (Jackson Immuno-Research) respectively. Cells were then mounted in solution containing PBS, 2 mM trolox, 50 M protocatechiuc acid (PCA) and 50 nM protocatechuate dehydrogenase (PCD) and imaging was performed as described (Pitchiaya et al., 2012). Emission from individual fluorophores was detected sequentially. Image processing was performed in Imaris and colocalization analysis was done in Imaris (Bitplane). Colocalization was calculated as the percentage of FITC spots that colocalized with ERG spots in the nucleus.

Chromatin Immunoprecipitation

VCaP cells were grown in complete medium and treated with peptidomimetics 12 hours prior to harvesting cells. ChIP assays were carried out as previously described (Brenner et al., 2011; supra; Yu et al., 2010; supra) using antibodies against ERG (Santa Cruz, # sc-354), DNA-PKcs (BD Biosciences, #610805), rabbit IgG (Santa Cruz, # sc-2027) or mouse IgG (Santa Cruz, # sc-2025). Briefly, chromatin collected from formaldehyde crosslinked and lysed cells was sonicated to an average length of 600 bp. Supernatants containing chromatin fragments were precleared using protein A/G beads (Upstate) and incubated with 3-5 µg of ERG antibody or IgG overnight prior to the addition of 50p of protein A/G beads for 1 hour. Antibody-bead precipitates were then washed six times and antibody/protein/DNA complexes were eluted with 150 µl IP elution buffer (50 mM aHCO$_3$, 1% SDS). To reverse the crosslinks, the complexes were incubated in elution buffer containing 10 µg RNase A and 0.3 M NaCl at 67° C. for 4-5 hours. DNA/protein complexes were then precipitated with ethanol, air-dried, and dissolved in 100 µl of TE. Protein was then digested by incubation with proteinase K at 45° C. for 1 hour and DNA was purified using a QIAGEN PCR column according to the manufacturer's protocol. QPCR was performed using appropriate primers as previously described (Brenner et al., 2011; supra).

Quantitative Real-Time PCR Assays

Total RNA was isolated from VCaP cells and tumors using Qiazol following the manufacturer's protocol (Qiagen). Quantitative PCR (QPCR) was performed using SYBR Green dye on an Applied Biosystems 7300 Real Time PCR system (Applied Biosystems) as described (Tomlins et al., 2005). Briefly, 2 µg of total RNA was reverse transcribed into cDNA using SuperScript III (Invitrogen) in the presence of random primers (Invitrogen). All reactions were performed in triplicate with SYBR Green Master Mix (Applied Biosystems) and 25 ng of forward and reverse primer according to the manufacturer's recommended thermocycling conditions, and then subjected to melt curve analysis. Threshold levels for each experiment were set during the exponential phase of the QPCR reaction using Sequence Detection Software version 1.2.2 (Applied Biosystems). The relative quantity of the target gene was calculated for each sample using the ΔΔCt method by the comparing mean Ct of the gene to the average Ct of the housekeeping gene, β-Actin (Livak and Schmittgen, 2001). All oligonucleotide primers were synthesized by Integrated DNA Technologies (Coralville, Iowa). The primer sequences for the transcript analyzed were previously described (Brenner et al., 2011; supra).

Immunoprecipitation

Cell pellets or tumors treated with or without the peptidomimetics were lysed in cell lysis buffer (20 mM MOPS, pH 7.0, 2 mM EGTA, 5 mM EDTA, 30 mM sodium fluoride, 60 mM β-glycerophosphate, 20 mM sodium pyrophosphate, 1 mM sodium orthovanadate, 1% Triton X-100, 1 mM DTT, protease inhibitor cocktail (Roche)). Cell lysates (0.5-1.0 mg) were pre-cleaned with protein A/G agarose beads (Santa Cruz) by incubation for 1 hour with shaking at 4° C. followed by centrifugation at 2000 rpm for 3 minute. Lysates were then incubated with 2 µg ERG antibody (Santa Cruz, C-17) at 4° C. for 4 hours with shaking prior to addition of 20 µl protein A/G agarose beads and incubated at 4° C. overnight. After washing 4 times with lysis buffer, beads were precipitated and resuspended in 25 µl of 2× loading buffer and boiled at 80° C. for 10 minutes. Samples were then analyzed by SDS-PAGE and Western blot analysis as described above.

Computational Analysis of ChIP-Seq Data

Short reads were aligned to the HG19 reference using Bowtie2 (Subramanian et al., 2005) with all default settings. Duplicate fragments (based on the coordinates of both reads) and fragments with only one mapped read were removed using samtools (Li et al., Bioinformatics 25, 2078-2079 2009). ERG peaks were called using PeakRanger (Feng et al., Bioinformatics 12, 139 2011) with default settings and a 1% FDR cut-off using chromatin input as control. To calculate read densities, ERG peaks (from both samples), merged using the reduce function from GenomicRanges (Lawrence et al., PLoS Comput Biol 9, e1003118 2013), were first converted to the GFF format, then fragments overlapping these peak regions were counted using featureCounts (Liao et al., Bioinformatics 2013) and the density was calculated by dividing the number of reads by the size of the reduced peak in kilobase pairs (kbp) and normalized by sequencing depth (per 1 million reads). Peaks were binned according to their significance in the control sample and the differences in read densities, separately for each bin, were assessed using a two-tailed t-test. Median signal profiles were calculated by: 1) calculating genome-wide ChIP signals using bedtools coverage (Quinlan and Hall, Bioinformatics 26, 841-842 (2010)) converting the BedGraph files into BigWig files using bedGraphToBigWig (Kent et al., Bioinformatics 26, 2204-2207 (2010)) extracting profiles within +/−1 kb around a summit with a resolution (window) of 100 bp using bx-python calculating for each peak a mean density within each window and; 5) calculating a median signal at each window across the 25% most-significant peaks.

Chicken CAM Assays

The CAM assays were performed as described previously (Brenner et al., 2011; supra). Briefly, fertilized eggs were incubated in a rotary humidified incubator at 38° C. for 10 days. First the CAM was released by applying mild pressure to the hole over the air sac and cutting a square 1 cm² window encompassing a second hole near the allantoic vein. Then cultured VCaP cells that stably express Cherry Red and pre-treated with peptidomimetics as indicated were detached by trypsinization and re-suspended in complete medium and 2×10⁶ cells were implanted adjacent to the mesenchyme in each egg. The windows were subsequently sealed and the eggs were returned to a stationary incubator. For invasion and intravasation experiments, implanted eggs were treated with 25 mg/kg body weight of the peptidomimetics 6 hrs after inoculation and both the upper and lower CAM were isolated after 72 hr. Invasive cells were processed and stained for chicken collagen IV as previously described (Brenner et al., 2011; supra). For metastasis and tumor growth assays, eggs were treated with 25 mg/kg body weight of indicated peptide administered every other day. At day 8 embryos were sacrificed and extra-embryonic tumors were excised and weighed. The embryonic lungs were harvested and analyzed for the presence of tumor cells by quantitative human alu-specific PCR. Genomic DNA from lower CAM and lungs were prepared using Puregene DNA purification system (Qiagen). Quantification of human cells in the extracted DNA was carried out as described (van der Horst et al., Biotechniques 37, 940-942, 944, 946 2004). Fluorogenic TaqMan qPCR probes were used as described above, and DNA copy numbers were quantified.

Chicken CAM Angiogenesis Assay

Angiogenesis assays were performed as described previously (Hood et al., J Cell Biol 162, 933-943 2003). Filter discs saturated with 1.5 mg peptides along with 5 mg/ml VEGF were placed on top of the 10-day old chicken embryo CAM. Retinoic acid (2 mg/ml), a known inhibitor of angiogenesis, was used as positive control. After 72 hours, filter discs and associated CAM tissues were harvested and quantified. Angiogenesis was assessed as the number of visible blood vessel branch points within the defined area of the filter discs.

Serum Kinetics of Peptide Concentration

Following IP injection of peptidomimetics, serum biotinylated peptide levels in mice was measured using the Quant-Tag Biotin kit (Vector) following the manufacturer instructions. Samples with known concentration of biotin were used to generate a standard curve to calculate the concentration of biotin in the serum samples.

Accession Numbers

Both the microarray data and the ChIP-seq data are deposited at Gene Expression Omnibus under accession number GSE58975.

Results

Identification and Characterization of ERG Binding Phage Peptides

Figure 1B:
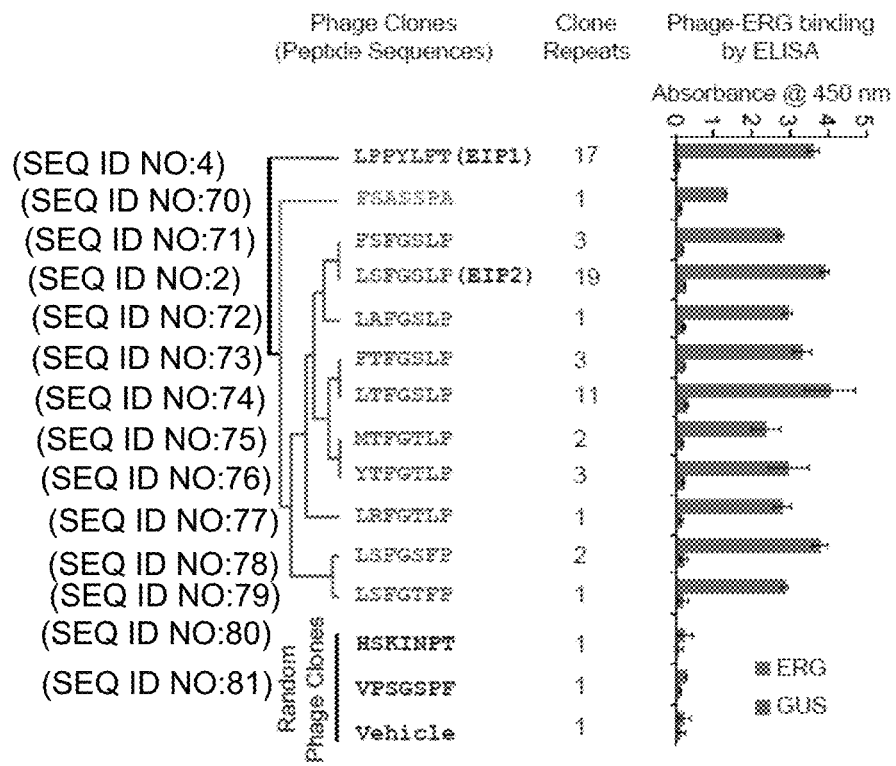

An iterative screening of a phage display random peptide library (complexity of 1.28×10⁹) was used to identify peptides that interact specifically with the wild-type ERG protein, but not a negative control protein, beta-glucuronidase (GUS) (FIG. 1A). After 4 rounds of selection, marked enrichment was observed (FIG. 8A-C), and a total of 64 individual phage clones were randomly selected for further screening. DNA sequence analysis revealed that altogether the 64 phage clones encoded 12 unique peptides (FIG. 1B). To confirm the specificity of the phage clones, ELISA plates were coated with purified ERG or control GUS proteins and the binding of phage was visualized with anti-M13 antibody. All 12 unique ERG-selected peptides bound to ERG, while the random peptides did not (FIG. 1B). Sequence alignment categorized the 12 ERG binding peptides into three groups (highlighted by different colors) and the most frequent peptide sequences in each group were designated "EIPs" (ERG Inhibitory Peptide).

The EIP1 (LPPYLFT) series was represented by 17 phage clones, and the amino acid sequence did not significantly match a known protein when aligned to the Swissprot database (BLAST). Interestingly, the EIP2 (LSFGSLP) series was represented by 46 phage clones (highlighted in red) (FIG. 1B) was found to be homologous to the SR domain of DLC1 protein, a tumor suppressor gene often deleted in liver, prostate, lung, colorectal, and breast cancers (Liao and Lo, The international journal of biochemistry & cell biology 40, 843-847 2008) (FIG. 8D).

Figure 1C:
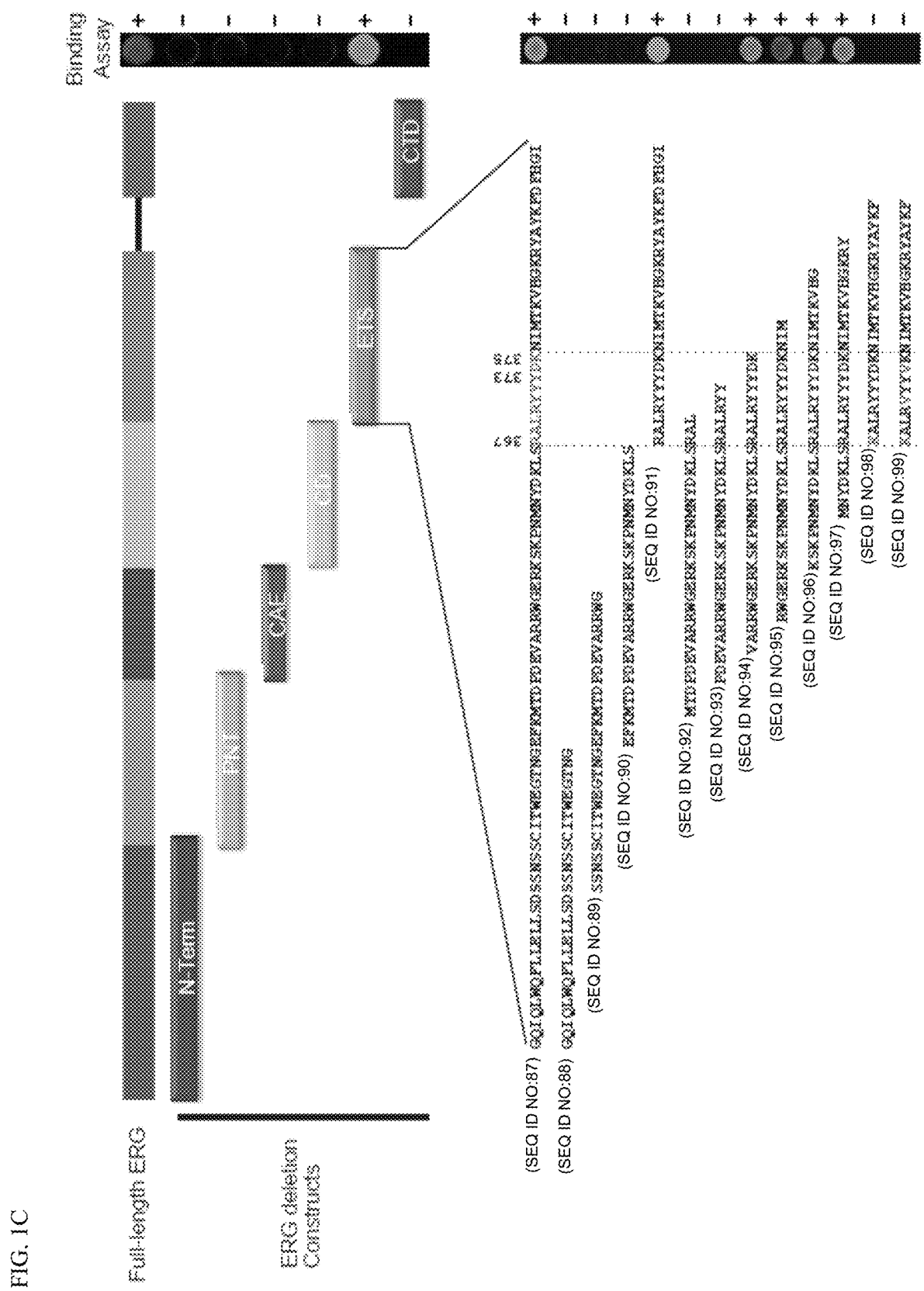

The interacting residues of ERG protein that contains 479 amino acids with two conserved domains, pointed (PNT) and the DNA binding (ETS) domains (Klambt, Development 117, 163-176 1993) were mapped (FIG. 1C). The pointed domain mediates hetero- or homo-dimerization (Carrere et al., Oncogene 16, 3261-3268 1998) and transcriptional repression (Fenrick et al., Mol Cell Biol 19, 6566-6574 1999). Other domains include the central alternative exons (CAE), central domain (CD) and C-terminal transactivator domain (CTD); however, their functions are less defined (Carrere et al., 1998; supra; Verger et al., J Biol Chem 276, 17181-17189 2001). To characterize the peptide binding domain, a total of 6 ERG segments, namely the N-terminus (N-term), PNT, CAE, CD, ETS and CTD, together with full-length ERG were cloned and expressed by in vitro transcription/translation as HaloTag fusion proteins; GUS was used as control (FIG. S1E) and the interactions were detected by HaloLink Arrays (FIG. 8F). Both phage clones EIP1 and EIP2 bound strongly to full length ERG as well as the ETS domain, but not to other domains or the control protein (FIG. 8F), demonstrating that the ETS domain is an important region for interaction with phage peptides.

In order to identify the minimal interactive residues in the ETS domain, a panel of 12 tiling fragments spanning the ETS domain (including two fragments with point mutations) were expressed and immobilized on HaloLink Arrays. This allowed us to specifically localize the interaction residues of the phage peptides to a 9 amino acid stretch (RAL-RYYYDK) (FIG. 1C), corresponding to residues 367 to 375 within the ETS domain of ERG. A single amino acid substitution of R367K completely abolished the peptide binding, indicating that $R^{367}$ is a critical residue required for interaction (FIG. 8G). Taken together, it is contemplated that mutations in amino acids 367 to 375 have a profound effect on ERG function.

Synthetic EIPs Specifically Bind to ERG and Disrupt ERG Protein-Protein Interactions In Vitro.

Figures 2A, 2B, 2C:
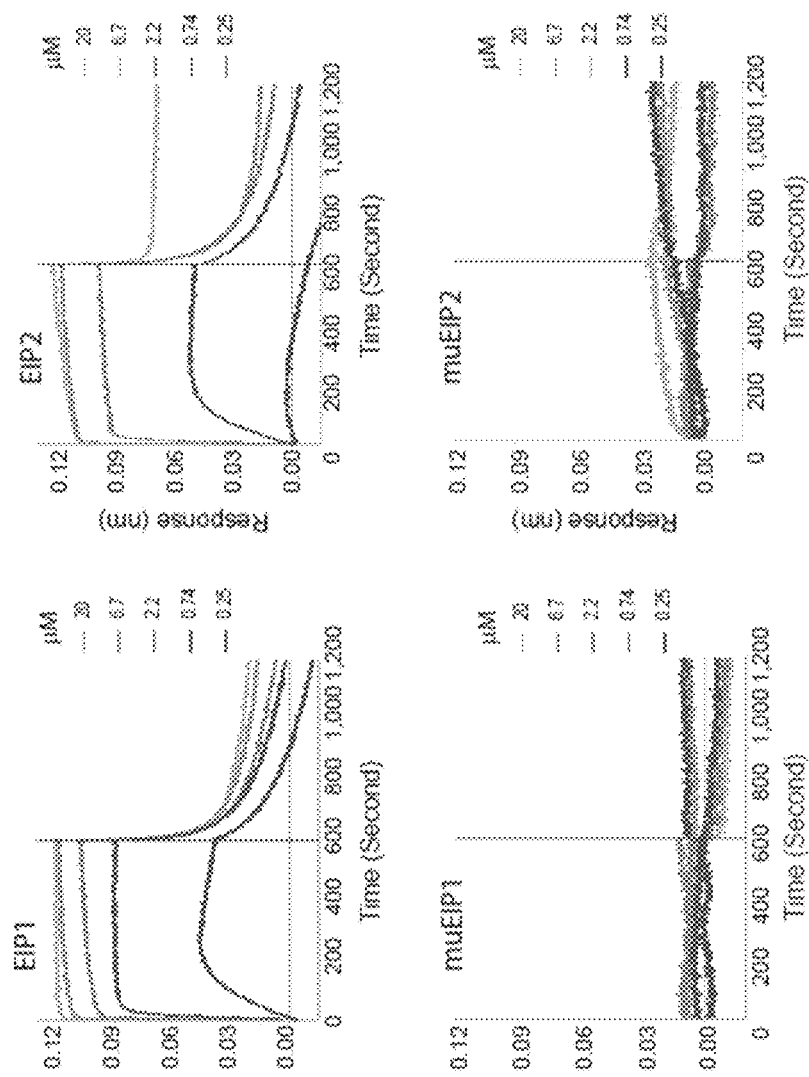

Peptides encoding EIP1, EIP2 and their mutants/scrambled derivatives (FIG. 2A) were synthesized to study their binding specificities to ERG by biolayer interferometry (ForteBio), a label-free biosensor technology that enables the real-time measurement of protein-protein interactions, quantitation, affinity, and kinetics. The binding kinetics of the synthetic peptides and dissociation constants (Kd) were calculated (FIG. 2A); Kds for EIP1 and EIP2 were 0.6 µM and 1.8 µM respectively, while the alanine substitutions (muEIP1 and muEIP2) and the scrambled peptide (Scr) could not be determined (N.D.) as they failed to bind to ERG protein (FIGS. 2B and 2C). The binding affinities for other peptides identified in FIG. 1B were also determined, while most of the peptide sequences bound to ERG, both EIP1 and EIP2 displayed significantly higher affinities (Table 1).

It was previously demonstrated that the ERG ETS domain interacted with AR and DNA-PKcs proteins in a DNA-independent manner (Brenner et al., Cancer Cell 19, 664-678 2011; Yu et al., Cancer cell 17, 443-454 2010), thus the ability of EIPs to disrupt the ERG:AR and ERG:DNA-PKcs interactions was tested in a cell-free system. Halo-tagged ERG protein was translated in vitro and incubated with recombinant AR or purified DNA-PKcs in the presence of increasing concentrations of EIP1, EIP2 or muEIP1. HaloLink magnetic beads were then used to pull down ERG followed by immunoblot analysis of AR or DNA-PKcs. Direct ERG:AR and ERG:DNA-PKcs interactions were both disrupted by the ERG binding peptides in a dose-dependent fashion, but not by the control peptide (FIG. 2D). To demonstrate EIP binding to endogenous ERG, biotinylated EIPs or mutant peptides were incubated them with cell lysates from the TMPRSS2:ERG-positive prostate cancer cell line VCaP. Pull-downs with streptavidin-linked agarose beads followed by immunoblot analysis showed that biotin-EIP pull-downs were enriched for the TMPRSS2:ERG gene fusion product in a concentration-dependent manner while the mutant pull-downs were not (FIG. 2E). The pull-downs were subsequently resolved by SDS-PAGE followed by silver staining that revealed a strong band at a molecule weight of 53 kDa in the biotin-EIP2 lane compared to the biotin-muEIP2 lane (FIG. 2F). Mass spectrometry analysis identified the 53 kDa band as ERG with 111 spectral counts for the ERG peptide NTGGAAFIFPNTSVY-PEATQR (SEQ ID NO: 110) in the biotin-EIP2 pull-downs and only 2 spectral counts in the mutant EIP2 (muEIP2) pull-downs (FIG. 2G).

Previously, it was demonstrated that the single point mutation Y373A in the ERG ETS domain abrogated the ERG:AR and ERG:DNA-PKcs interactions (Brenner et al., 2011; supra). Here, the importance of the Y373A mutation in the ERG:EIP interaction was investigated.

Figure 9A:
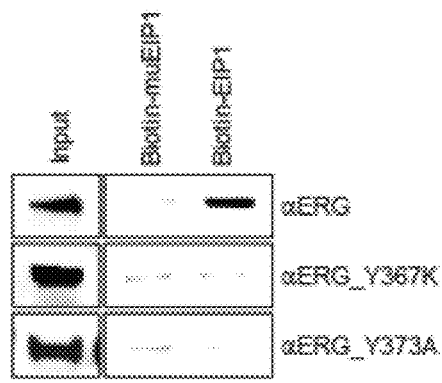
FIG. 9A-F shows binding properties of synthetic peptides. (A) Pull-down experiment was performed by incubating purified recombinant proteins and biotin-peptides. (B-C) Representative sensorgrams for both wtERG and ERG_Y373A binding to EIP1. Real-time binding was measured by immobilization of biotinylated proteins to the streptavidin biosensors and subsequent interactions with varying concentrations of synthetic peptides as indicated. (D) Steady-state analysis of real-time binding data for wtERG/ERG_Y373A and synthetic peptides. (E) Electrophoretic mobility shift assay (EMSA) for ERG and ETS binding sequence (EBS). (F) Competitive EMSA demonstrates that EIP1 disrupts the interaction of ERG with DNA.
Figure 9B:
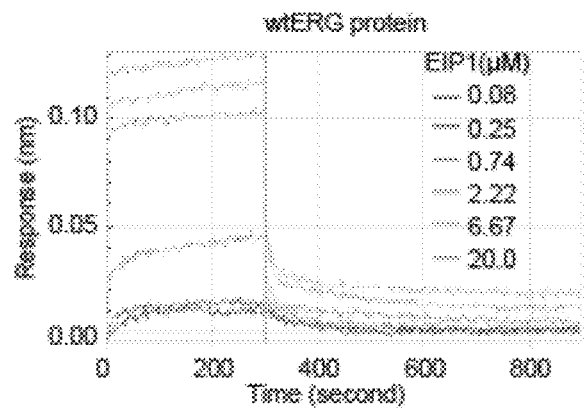
Figure 9C:
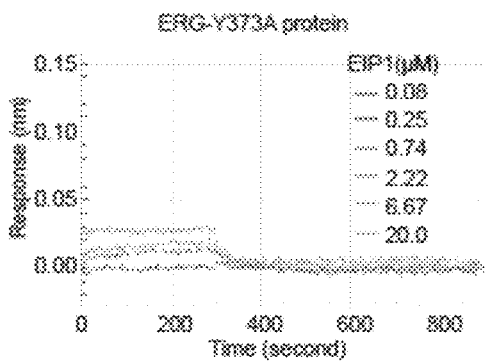
Figure 9D:
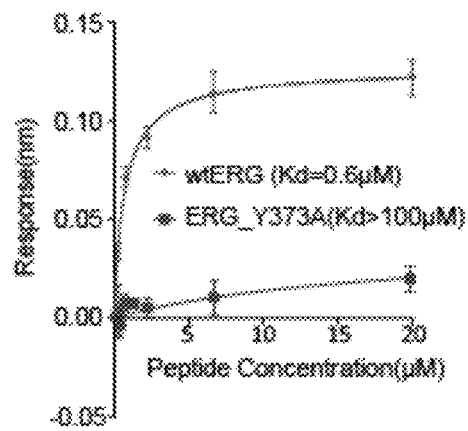

Immunoprecipitation analyses showed that only wild-type ERG (wtERG) was pulled down by biotin-conjugated EIP1, but not the mutant version of ERG_Y373A (FIG. 9A). In addition, the kinetic binding curves (sensorgrams) of EIP1 on both wtERG and Y373A mutation wee compared by OctetRED, and the binding affinities (measured by Kd) are significantly different for wtERG and ERG_Y373A (0.6 µM vs >100 µM) (FIG. 9B-D), further confirming the importance of $Y^{373}$ in ERG:EIPs interaction.

Figure 9E:
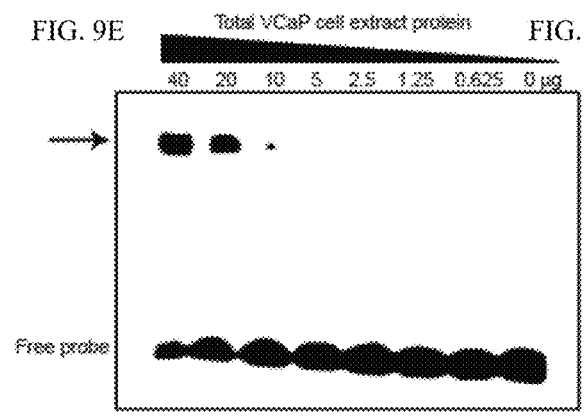
Figure 9F:
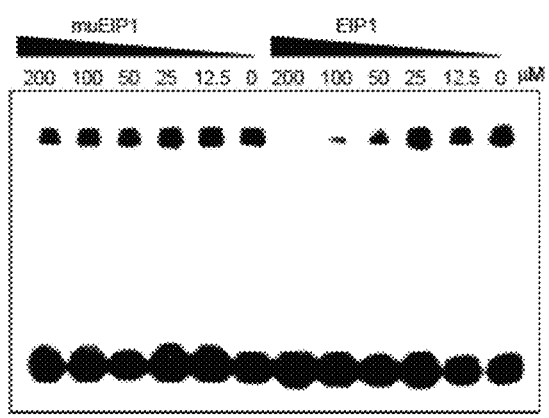

To assess whether EIPs disrupt ERG binding to DNA, an electrophoretic mobility shift assay (EMSA) was performed in VCaP cell extracts using a validated consensus ETS binding sequence (EBS) (Flajollet et al., Molecular cancer research: MCR 9, 914-924 2011). While the ERG protein impeded EBS mobility (FIG. 9E), addition of EIP1, but not the control peptide, effectively disrupted the ERG:EBS DNA interaction in a dose-dependent manner (FIG. 9F). Taken together, these data clearly demonstrate, that in a cellular context, the effects of EIPs on disruption of ERG function occur by blocking ERG:DNA and/or critical ERG: protein interactions.

Cell Permeable EIPs Co-Localize with ERG Protein and Block ERG-Mediated Cell Invasion.

Figure 10A:
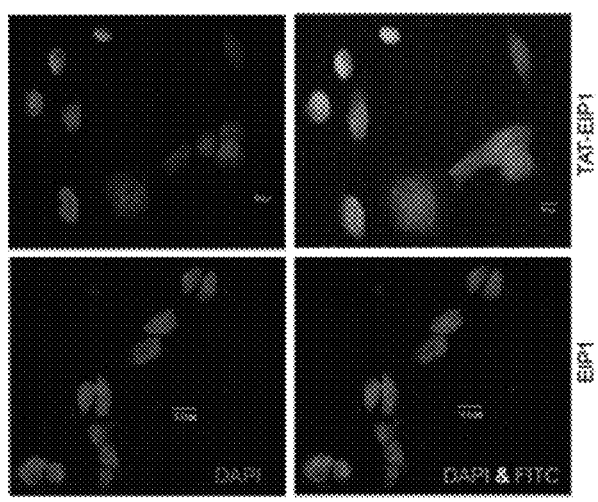
FIG. 10A-F shows that cell-permeable peptides block ERG-mediated cell invasion. (A-E) Representative Octet-RED sensorgrams for ERG binding to cell permeable peptides or controls. (F-G) OctetRED sensorgrams and kinetic binding data for the mutant TAT-EIP1. (H) VCaP cells were treated with FITC-labeled TAT-EIP1 or EIP1, mounted and counterstained with DAPI before imaging. (I) Representative pseudocolored images of PC3 (top) and PC3 cells over-expressing ERG (bottom). (J) Western blot analysis to determine expression levels of ERG and EZH2 in the stable isogenic RWPE-1 models. (K) Invasion assays of RWPE1-ERG cells in the presence of TAT-EIPs and mutant EIP1. (L) Western blot analysis of ERG expression in stable isogenic PC3 cells. (M) Invasion assays of PC3-ERG cells performed as in FIG. 3E-H.
Figure 10B:
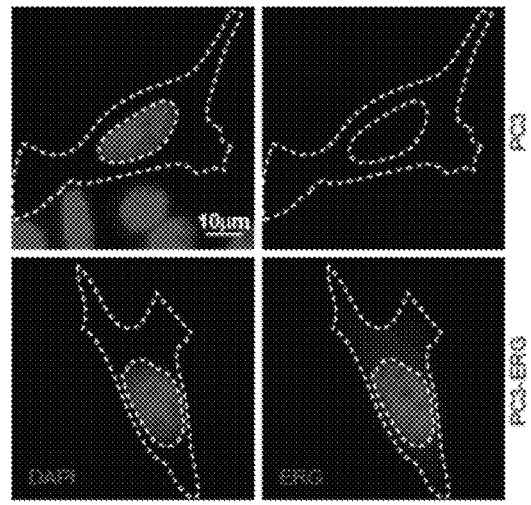
Figure 10C:
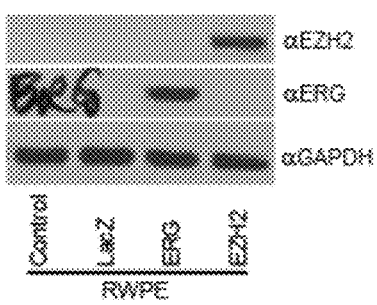
Figure 10D:
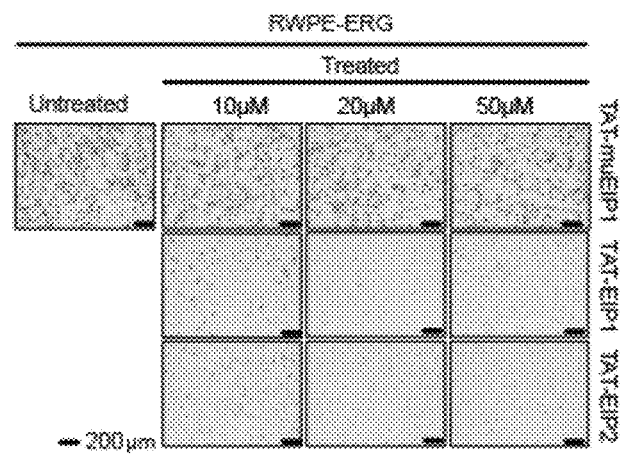
Figure 10E:
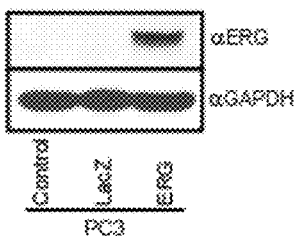
Figure 10F:
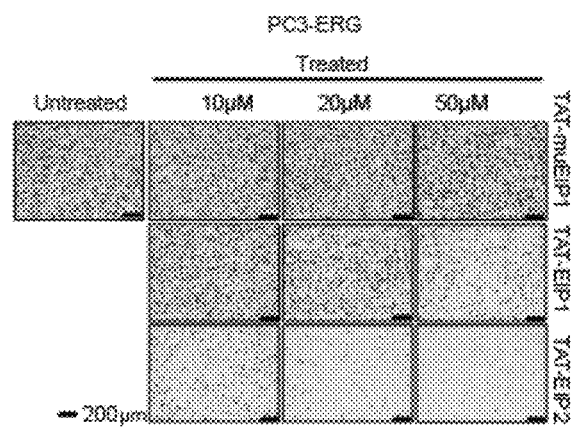

It was next determined whether the synthetic peptides could inhibit ERG-mediated oncogenic phenotypes in a panel of prostate cell lines. Cell-permeable peptides were synthesized by conjugating the EIPs with the cationic HIV-TAT motif RKKRRQRRR (SEQ ID NO:7) to facilitate uptake into the cells (Wadia and Dowdy, Adv Drug Deliv Rev 57, 579-596 2005) (FIG. 3A). Conjugating the TAT sequence to EIPs did not compromise the binding affinities to ERG; Kd values were 0.68 µM and 1.11 µM for TAT-EIP1 and TAT-EIP2 respectively (FIG. 3B), and not calculable for the controls (FIG. 10A-E). To further confirm binding specificity, a series of alanine substitution peptides based on the parental TAT-EIP1 sequence were synthesized ad the Kd value was measured for each peptide (FIG. 10F) using OctetRED. The data showed >100-fold increase in Kd for either $P^2 \rightarrow A$ or $Y \rightarrow A$ substitution, while $L^5 \rightarrow A$ displayed non-specific binding (FIG. 10G).

Figure 3D:
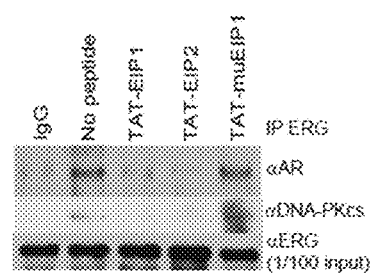

Because TAT also functions as a nuclear localization signal (Efthymiadis et al., J Biol Chem 273, 1623-1628 1998), it is well suited for the delivery of transcription factor inhibitors. Immunofluorescence confocal microscopy showed that FITC-labeled TAT-EIP1 clearly entered VCaP cells, while EIP1 without the TAT motif did not penetrate the cell membrane (FIG. 10H). To further examine the ERG:EIP interaction in situ, an immunofluorescence co-localization assay was performed in VCaP cell using the FITC-labeled peptides and an ERG antibody. A PC3 cell line stably overexpressing ERG protein was contacted with the ERG antibody and it was found that the parental PC3 cells lacking ERG did not display any significant signal, while in PC3-ERG cells, ERG displayed a strong nuclear signal and a weak cytoplasmic signal (FIG. 10I), similar to the cellular localization data described in the Human Protein Atlas (HPA) project. In VCaP cells, it was found that EIPs extensively co-localized with ERG, whereas a control peptide muEIP did not (FIG. 3C). While the control peptide was predominantly cytoplasmic, EIPs were found in both the nucleus and the cytosol, colocalizing with ERG in both compartments. The extent of green-red colocalization in the nucleus was significantly different with 78±5 percent for EIP1, while 7±3 percent for the control peptide. In concordance with the cell-free system (FIG. 2D), IP-Western blot analysis showed that TAT-EIP1/2 significantly blocked the ERG:AR and ERG:DNA-PKcs interactions in VCaP cells, whereas the mutant peptide had no effect (FIG. 3D).

Figure 3E:
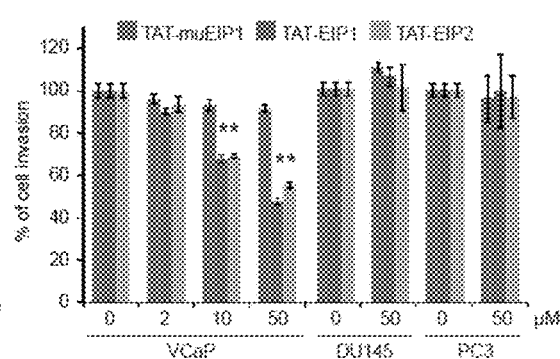
Figure 3F:
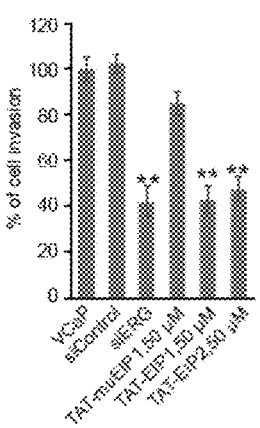
Figure 3G:
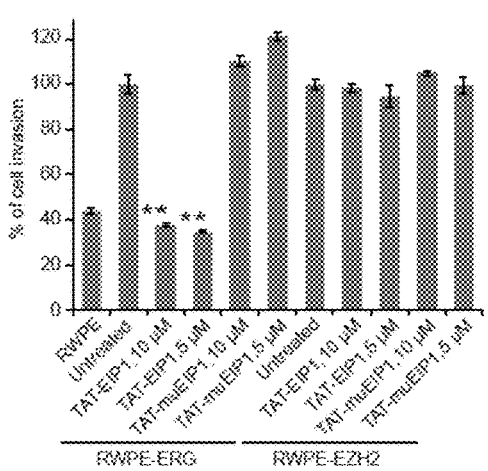
Figure 3H:
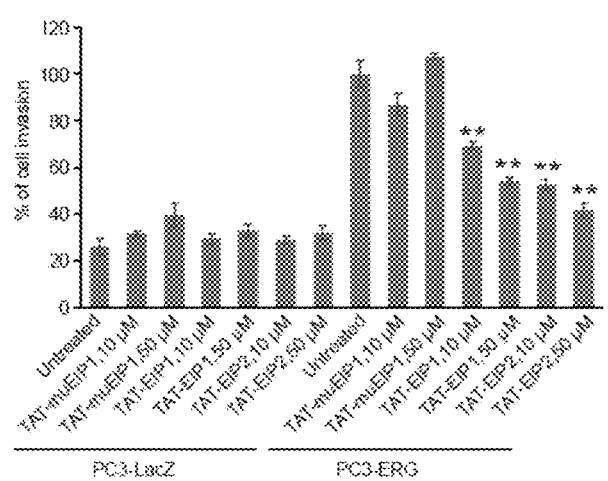

Next, it was tested whether TAT-EIPs could attenuate tumor cell invasion in modified Boyden chamber assays. Addition of TAT-EIP1/2 significantly inhibited VCaP cell invasion comparable to the levels achieved by ERG-siRNA (FIG. 3E-F) while they had no effect on ETS gene fusion-negative prostate cancer cell lines, DU145 and PC3 (FIG. 3E). Two RWPE-1 cell lines stably overexpressing either ERG or EZH2 that are highly invasive compared to parental RWPE-1 or RWPE1-LacZ cells (FIG. 10J-K) (Cao et al., Oncogene 27, 7274-7284 2008; Tomlins et al., Neoplasia 10, 177-188 2008) were utilized. Addition of TAT-EIP1/2 significantly attenuated invasion of RWPE1-ERG, but not RWPE1-EZH2 cells; control peptides had no effect on either cell line (FIG. 3G). Likewise, TAT-EIP1/2 inhibited PC3 cell invasion driven by overexpression of ERG, but not the PC3-LacZ control cells (FIG. 3H, FIG. 10L-M). Together, the data demonstrates that TAT-EIPs are able to specifically block ERG-induced cell invasion.

Retroinverso EIPs (RI-EIPs) Specifically Bind to and Destabilize ERG

Figure 19A:
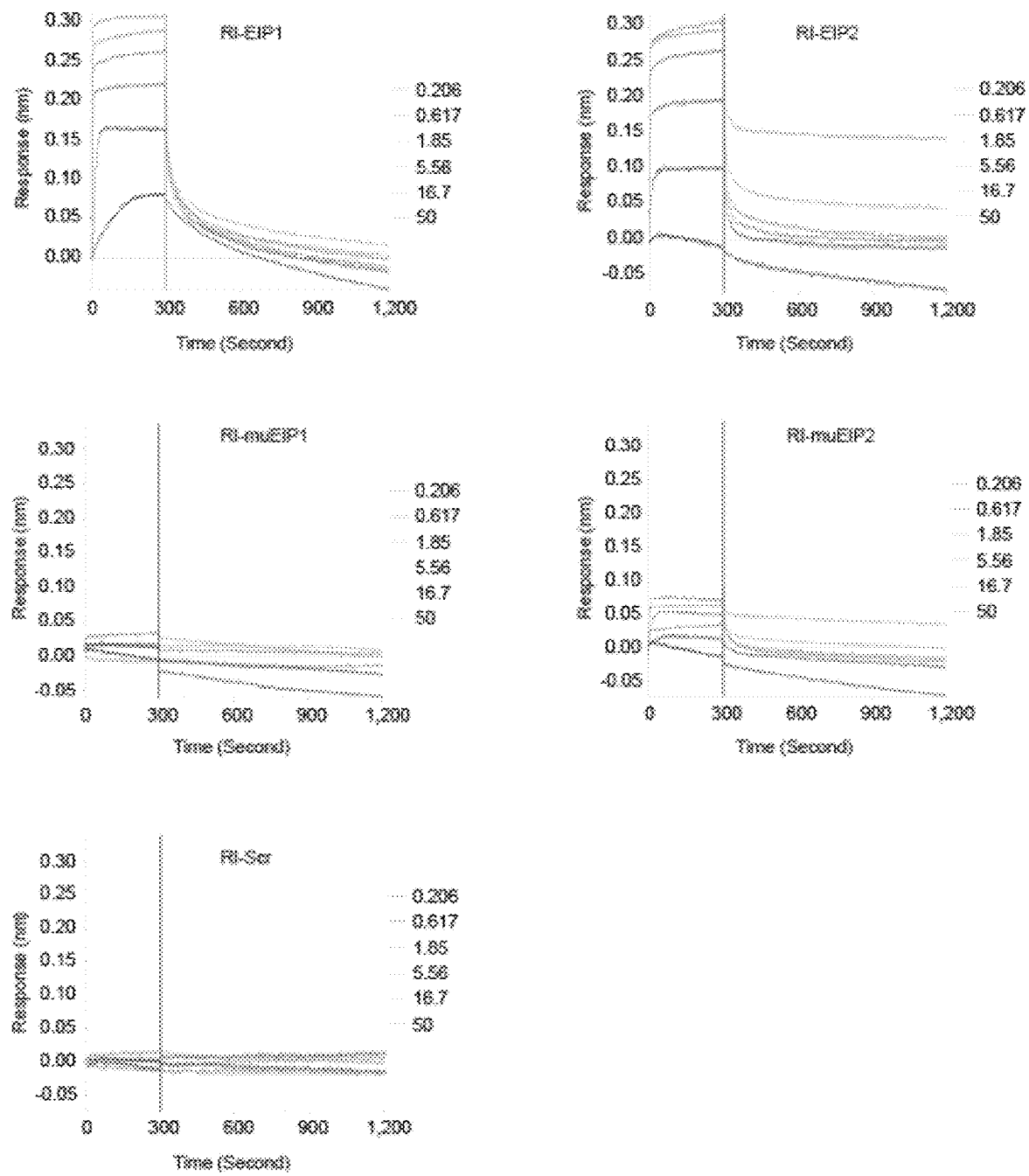
FIG. 19A-R shows that retroinverso EIPs specifically bind to and destabilize the ERG target. (A) Representative OctetRED sensorgrams for ERG binding to retroinverso peptides. (B) Boyden chamber transwell invasion assays of RWPE-ERG or LacZ cells performed as in FIG. 3E-H. (C) Boyden chamber transwell invasion assays of VCaP cells performed as in FIG. 3E-H. The data shown are the mean of three independent experiments. (D) VCaP cell proliferation measured by CellTiter-Glo after long-term treatment with RI-EIP2 (5 to 13 days as indicated). (E) Confluence rate for VCaP cells measured as in FIG. 4C except using RI-EIP2. (F-H) Confluence rate for VCaP cells measured as in FIG. 4C except the cells were cultured in charcoal stripped media. (I-J) IP-Western blot analysis of VCaP cells treated with either RI-EIPs or -muEIPs. (K) Olaparib-treated VCaP cells were analyzed following temperature shift from 42° C. to the indicated temperatures. PARP1 protein expression in the soluble fraction of the cell lysates was detected by Western blotting. (L-M) VCaP cells were treated with either RI-EIPs or RI-muEIPs and the assays were performed as in FIG. 4F. (N-O) Immunoblot analysis of ERG, AR and GAPDH in VCaP cells treated with RI-EIP2 or RI-muEIP1 for indicated time points and concentrations. The assays were performed as in FIG. 4H-I. (P) Immunoblot analysis of ERG and GAPDH in VCaP cells treated with TAT-EIPs or control peptides. (Q-R) Immunoblot analysis of ERG, PARP and GAPDH in RWPE1-ERG or PC3-ERG cells treated with RI-EIPs or control peptides.

To test the EIPs in in vivo models, a retroinverso version of the peptides was used. A retroinverso peptide is made up of D-amino acids in a reversed sequence and has a side-chain topology similar to that of its parent molecule but with inverted amide peptide bonds. In contrast to L-amino acids, retroinverso peptides were shown to enhance the biological activity in xenograft models as these peptides retain similar structural configuration of their parent molecules, but are resistant to cleavage by serum or cellular proteases (Cerchietti et al., Blood 113, 3397-3405 2009; Snyder et al., PLoS Biol 2, E36 2004). It was tested whether retroinverso peptidomimetics (RI-EIPs) (FIG. 19A) are structurally stable and retain specific ERG inhibitory properties of the parental L-amino acid peptides. The kinetic binding assay by the biolayer interferometry revealed that RI-EIPs have similar binding affinity as TAT-EIPs with 0.94 µM and 1.28 µM for RI-EIP1 and RI-EIP2 respectively; Kds were not calculable for the control peptides (FIG. 4B; FIG. 19A).

Figure 19B:
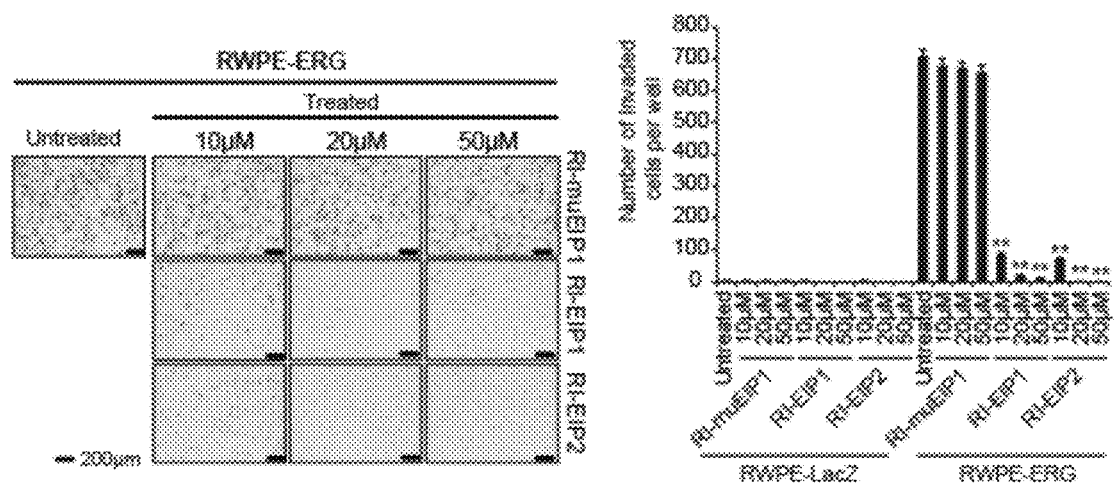
Figure 19C:
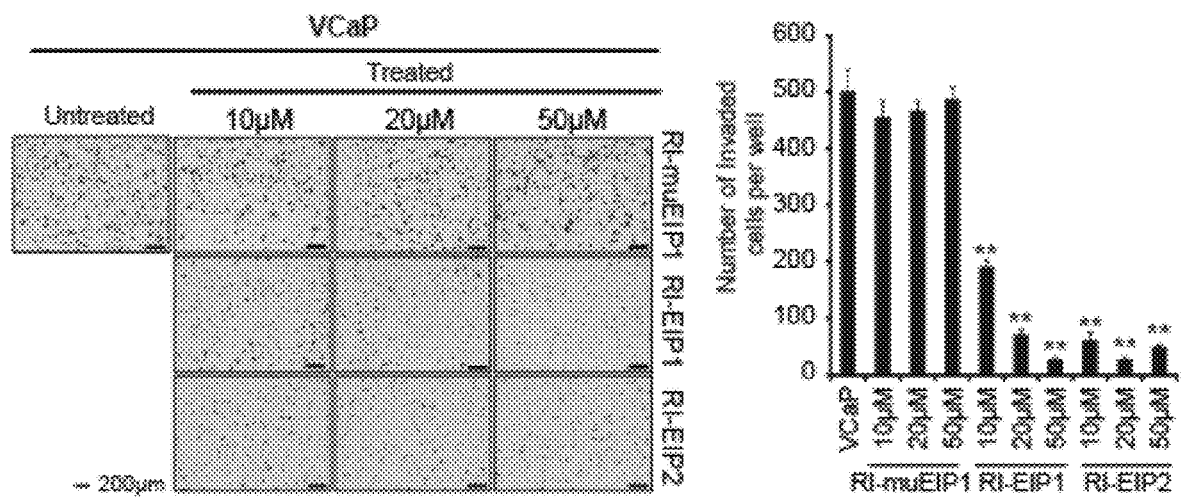
Figure 19D:
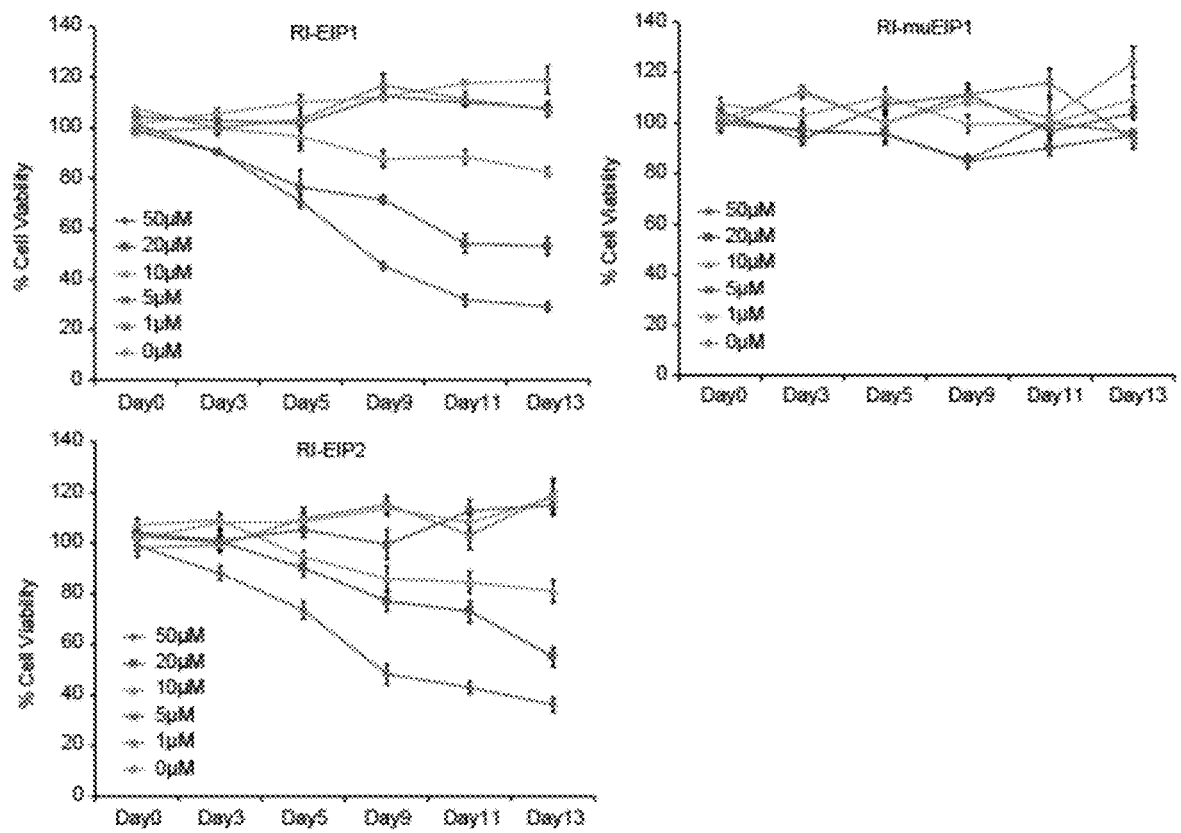
Figure 19E:
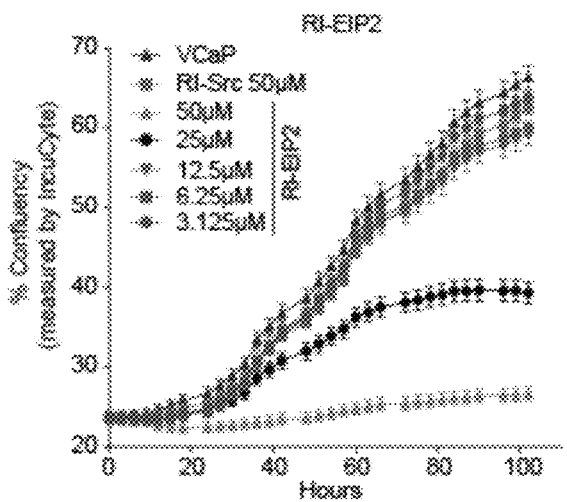
Figure 19F:
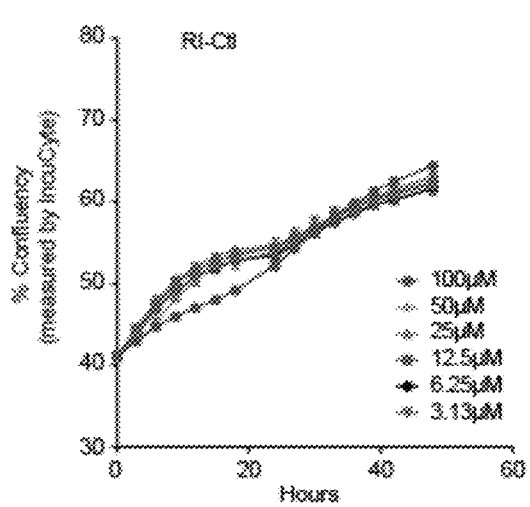
Figure 19G:
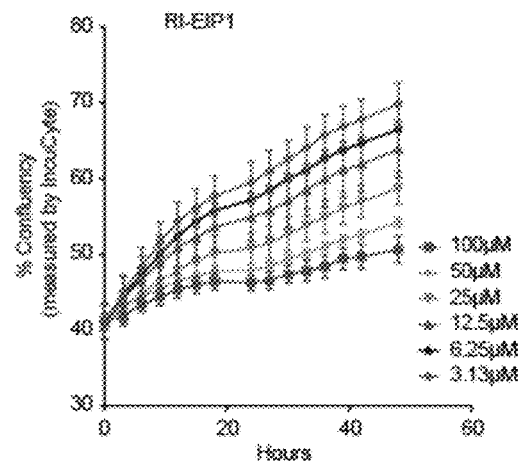
Figure 19H:
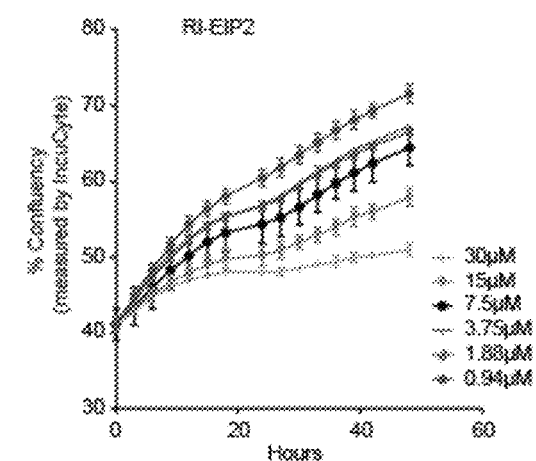

The effect of RI-EIPs on cell invasion was evaluated. Similar to TAT-EIPs, the peptidomimetics also blocked ERG-driven cell invasion in RWPE-1 cells (FIG. 19B) and inhibited cell invasion in VCaP (FIG. 19C). To determine the effect of RI-EIPs on cell proliferation, VCaP cell viability by CellTiter-Glo assay at different time points in the presence of various doses of the peptidomimetics. Starting at day 5, both RI-EIP1 and RI-EIP2 demonstrated an inhibitory effect on cell proliferation at a dosage of 10 µM and above, while RI-muEIP1 had no affect (FIG. 19D). Further, the RI-EIPs significantly decreased the confluence rate of VCaP cells (ERG fusion positive) as measured by IncuCyte in a dose-dependent fashion but not DU145 cells (ERG fusion negative) (FIG. 4C-E, FIG. 19E). The confluence rate of VCaP cells cultured in charcoal stripped media (without androgen) was also remarkably inhibited by RI-EIPs treatment in a dose-dependent fashion as compared to the control peptide (FIG. 19F-H).

Figure 19I:
Figure 19J:
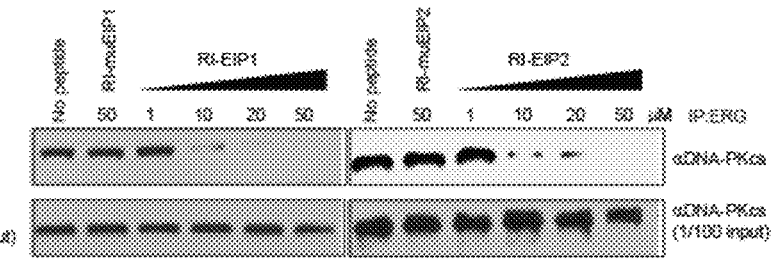
Figure 19K:
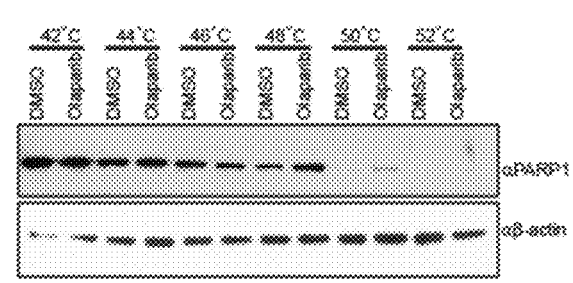
Figure 19L:
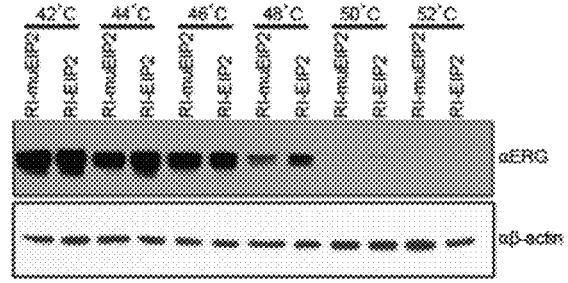
Figure 19M:
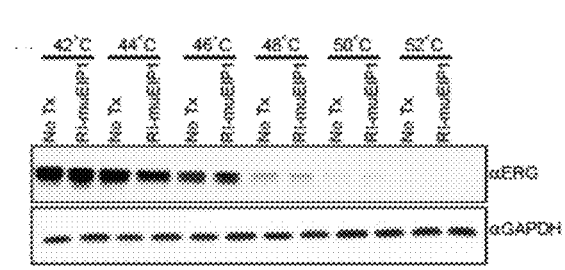

It was next determined whether RI-EIPs inhibit ERG associated protein-protein interactions and found that the treatment of VCaP cells with RI-EIPs disrupted both ERG:AR and ERG:DNA-PKcs interactions (FIG. 19I-J). The cellular thermal shift assay (CETSA) has been used to monitor drug target specificity as well as dose-dependent target engagement in cells and tissues (Martinez Molina et al., Science 341, 84-87 2013). This technique was applied to evaluate the target binding specificity of RI-EIPs. Olaparib, a PARP-1 inhibitor that induced the thermal shift of PARP-1 target protein in VCaP cell was tested first (FIG. 19K). Likewise, treatment of VCaP cells with both RI-EIPs significantly increased the levels of soluble ERG protein even at 50° C. (FIG. 4F, FIG. 19L), while most ERG protein precipitated at 48° C. in both untreated and RI-muEIP1 treated VCaP cells (FIG. 19M), clearly demonstrating the direct binding of RI-EIPs and ERG protein. The RI-EIP1-induced solubility of ERG protein was increased in a dose-dependent fashion as determined by the isothermal dose-response procedure (Martinez Molina et al., 2013; supra) (FIG. 19G). All CETSAs were performed after 3 hours treatment with the peptidomimetics at the indicated doses and temperatures.

Figure 4M:
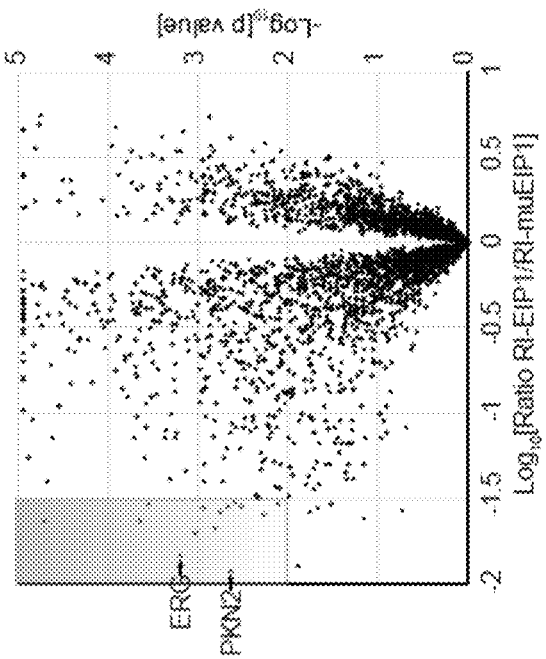
Figure 4J:
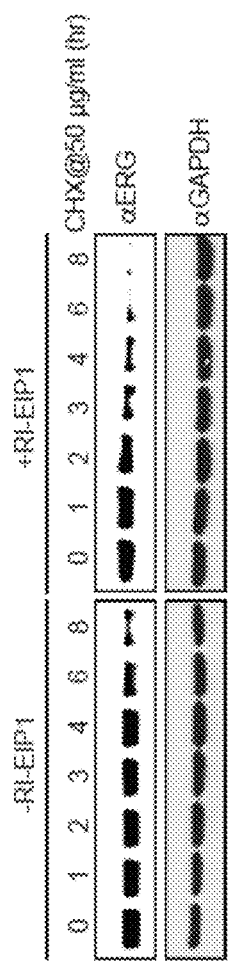
Figure 4L:
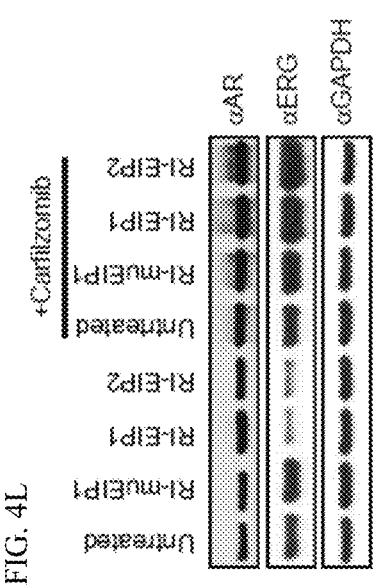
Figure 4K:
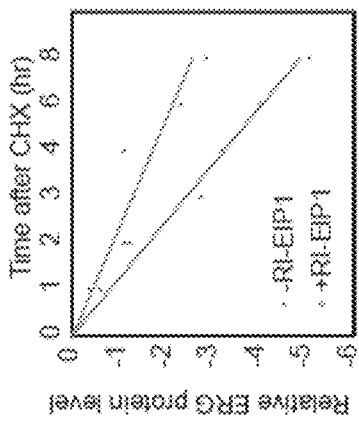
Figure 19N:
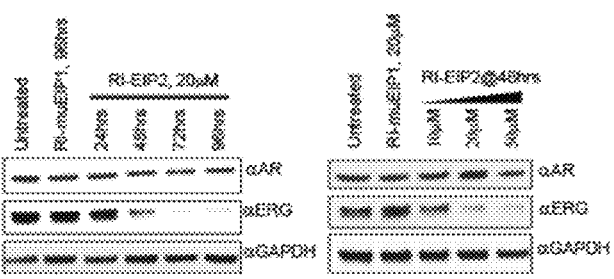
Figure 19O:
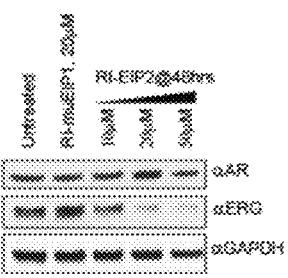
Figure 19P:
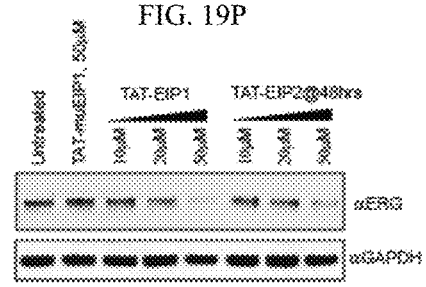
Figure 19Q:
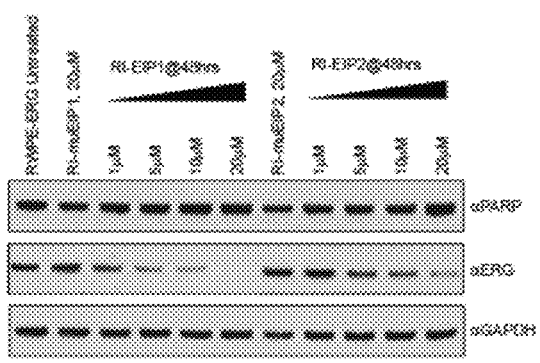
Figure 19R:
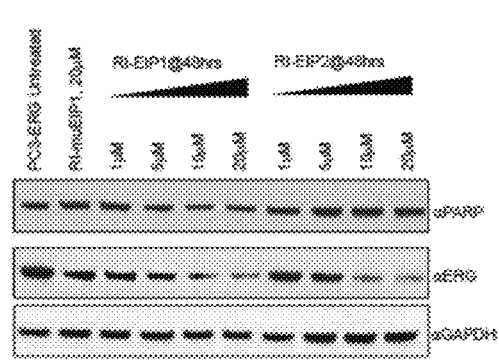

The effects of RI-EIPs on ERG and AR proteins in cells at different time points was investigated. The treatment of VCaP cells with both RI-EIP1 and RI-EIP2 significantly destabilized the ERG target protein starting at 24 hours post-treatment in a dose dependent manner, while control RI-muEIPs had no effect (FIG. 4H-I; FIG. 19N-O). This is also the case for the native peptides, where TAT-EIPs degraded the ERG protein, but not the control peptide (FIG. 19P). In the presence of cycloheximide (CHX), a protein synthesis inhibitor, RI-EIP1 significantly shortened the ERG protein half-life (FIG. 4J-K) and degradation was seen as early as 3 hours. Degradation of ERG protein was completely inhibited by carfilzomib (FIG. 4L), a proteasome inhibitor, indicating involvement of the proteasome-mediated proteolysis. These findings were confirmed in two isogenic cell models, RWPE1-ERG and PC3-ERG cells. Similar to VCaP cells, both RI-EIP1 and RI-EIP2 destabilized the ERG proteins even at 5 µM concentration (FIG. S4Q-R), consistent with earlier findings. To study the global effects of peptidomimetic treatment, unbiased proteomic analysis of VCaP cells by was confirmed by mass spectrometry after 48 hours of incubation with either RI-EIP1 or control peptides. Of 3020 proteins identified from mass spectrometry, ERG was one of the top-ranked candidates most significantly depleted upon peptidomimetic treatment ($P<0.01$) (FIG. 4M).

RI-EIPs Specifically Inhibit ERG Binding to Target Loci and Inhibit ERG Transcription Activity.

Figure 20A:
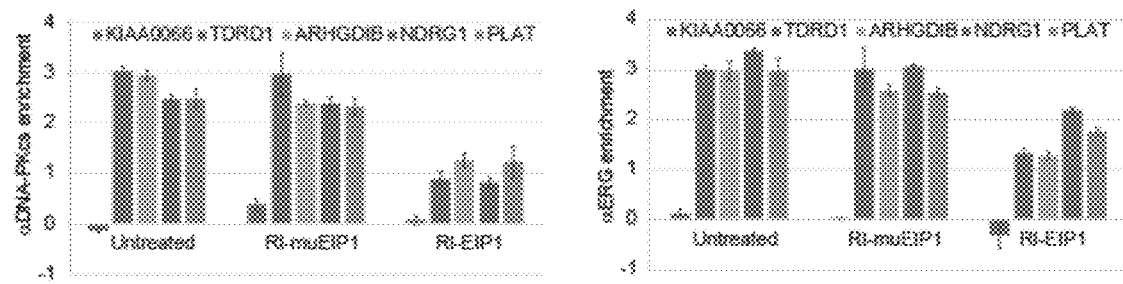
FIG. 20A-H shows that RI-EIPs disrupts ERG transcription activity, related to FIG. 5. (A) ChIP assays performed using ERG and DNA-PKcs antibodies on VCaP cells treated with the peptides for 12 hours prior to crosslinking. (B) Immunoblot analysis of ERG and GAPDH in the ChIP-seq samples precipitated by ERG antibody from the VCaP cell lysate in FIG. 5A. (C) Immunoblot analysis of ERG and GAPDH in VCaP cell treated by the indicated peptides for 12 hours. (D) Venn diagram illustrating the overlap of disregulated genes (greater than 2-fold, FDR<0.01) between siERG- and RI-EIP2-treated VCaP cells. (E) Venn diagram illustrating the overlap of disregulated genes between RI-EIP1 and RI-EIP2-treated VCaP cells. (F) Heatmap from microarray analysis of ERG knockdown by siERG or RI- EIP2 treatment in VCaP cells, comparing gene expression changes upon siERG knockdown and RI-EIP2 treatment. (G-H) Scatter plots of gene expression, comparing the gene profiles in PC3 (G) with VCaP (H).

In a cellular context, the data showed EIPs block ERG binding to DNA (FIG. S2F) as well as disrupt ERG:DNA-PKcs interaction (FIG. 3D). Chomatin immunoprecipitation (ChIP) assays in VCaP cells were performed to assess whether peptide treatment could block endogenous ERG recruitment to chromatin. These experiments clearly demonstrated that RI-EIP1, but not mutant peptide, inhibits ERG and DNA-PKcs enrichment at ERG-regulated genomic loci (FIG. 20A), supporting the hypothesis that EIPs specifically block the recruitment of ERG and its co-factors such as DNA-PKcs to ERG targeted genomic loci.

Figure 5A:
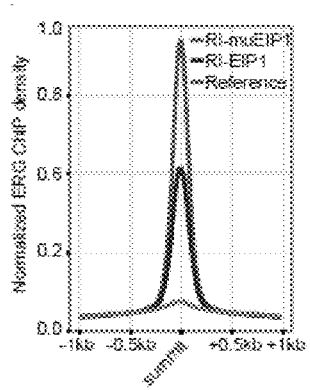
FIG. 5A-G shows that retroinverso EIPs specifically inhibit ERG binding to target loci, disrupting ERG transcription activity. (A) ChIP-seq using the ERG antibody was performed in VCaP cells treated with 50 μM RI-EIP1 or RI-muEIP1 for 12 hours. (B) Heatmap representation of ERG binding peaks in both RI-EIP1 and RI-muEIPs treatment groups. (C) Representative ChIP-seq profile at ERG target gene loci. (D) Venn diagram illustrating the overlap of disregulated genes (greater than 2-fold, FDR<0.01) between siERG- and RI-EIP1-treated VCaP cells. Knockdown of PCAT29 in VCaP cells was used as a negative control. (E) Heatmap from microarray analysis of ERG knockdown by siERG or RI-EIP1 treatment in VCaP cells, comparing gene expression changes upon siERG knockdown and RI-EIP1 treatment. (F) Gene Set Enrichment Analysis (GSEA) of RI-EIP1-treated VCaP cells shows that genes down-regulated upon RI-EIP1 treatment (VCAP_RI-EIP1_DN) are significantly and negatively enriched upon ERG knockdown. NES, normalized enrichment score; FDR, false discovery rate. (G) The relative expression of several ERG target genes in VCaP upon RI-EIP1 treatment assessed by quantitative PCR. For all experiments mean±SEM is shown.
Figure 5B:
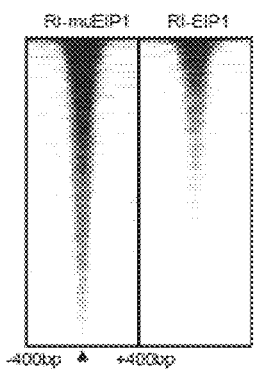
Figure 5C:
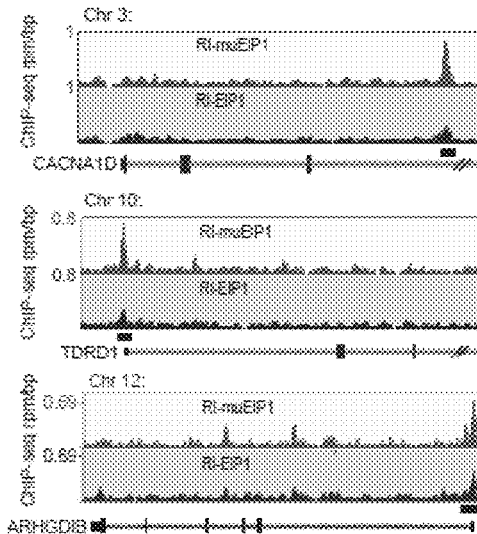
Figure 20B:
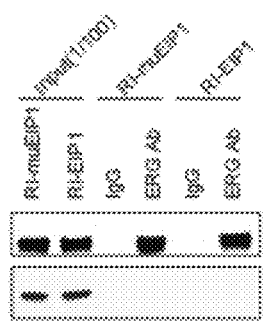

The unbiased genome-wide recruitment of ERG was assessed by chromatin immunoprecipitation coupled with high-throughput sequencing (ChIP-seq) utilizing ERG antibody in VCaP cells (Asangani et al., Nature 510, 278-282 2014; Chen et al., Nature medicine 19, 1023-1029 2013; Chng et al., The EMBO journal 31, 2810-2823 2012; Nguyen et al., Cancer cell 27, 797-808 2015; Yu et al., 2010 supra). The ERG proteins precipitated by antibodies were first confirmed to be at equal amounts by immunoblot (FIG. 20B). Over 97% of the most significant peaks ($4^{th}$ quartile) identified in RI-muEIP1-treated VCaP overlapped with the untreated VCaP cells. The average ChIP-seq signal for these $4^{th}$ quartile peaks were markedly reduced in RI-EIP1-treated cells compared to mutant peptide (FIG. 5A-B), indicating the inhibition of ERG binding at target loci upon RI-EIP treatment. Examples of gene tracks for ERG-associated genomic regions and the effects upon peptide treatments on its enrichment are shown in FIG. 5C.

Figure 5D:
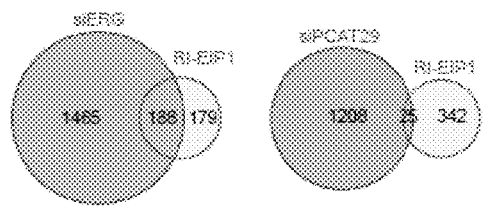
Figure 5E:
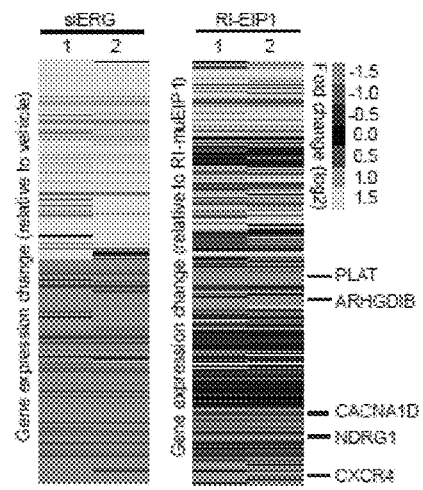
Figure 5F:
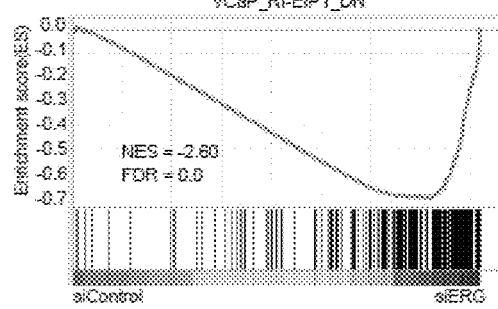
Figure 20C:
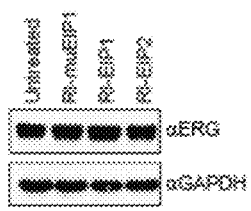
Figure 20D:
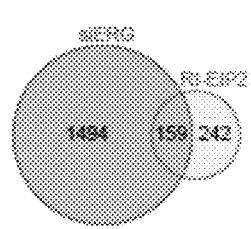
Figure 20E:
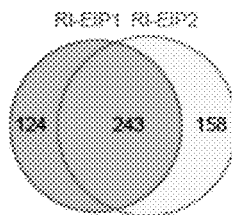
Figure 20F:
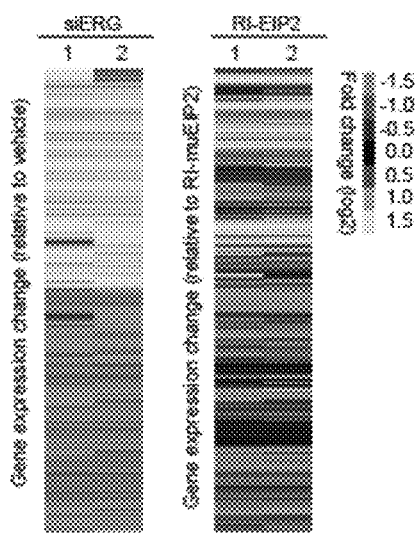
Figure 20G:
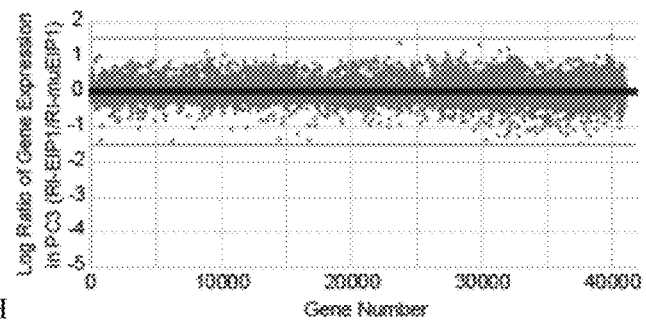
Figure 20H:
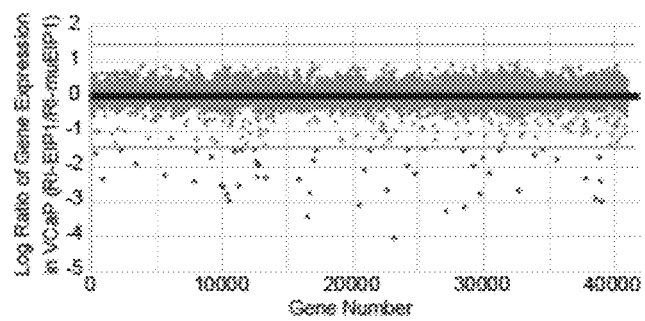

The changes in global gene expression profiles upon siERG or RI-EIPs treatment was investigated by microarray analysis on VCaP cells. Alterations in the ERG-regulated genes by siERG upon RI-EIP1 or RI-muEIP1 treatment was assessed (selection criteria greater than 2-fold, FDR<0.01). ERG protein was first assessed to be at equal amounts after the peptide treatment (FIG. 20C). There was significant overlap of the dysregulated genes between siERG- and RI-EIP1/2-treated VCaP cells, as well as between RI-EIP1 and RI-EIP2-treated VCaP cells (p<0.001) (FIG. 5D; FIG. 20D-E). Earlier, a series of prostate cancer-specific long noncoding RNAs (PCATs) were identified (Prensner et al., Nature biotechnology 29, 742-749 2011); one lncRNA, PCAT29 is an androgen-regulated lncRNA that functions as a tumor suppressor in prostate cancer (Malik et al., Molecular cancer research: MCR 12, 1081-1087 2014). For comparison, PCAT29 was knocked down by siRNA which also resulted in significant alteration of global gene expression but very few regulated genes were shared between siP-CAT29- and RI-EIP1-treated VCaP cells (FIG. 5D). A heat map view demonstrated substantial similarities in the gene expression profiles for both siERG- and RI-EIP1/2-treated cells, indicating RI-EIP1/2 treatment attenuates ERG-mediated transcriptional activities (FIG. 5E; FIG. 20F). A gene array analysis was performed in PC3 cells (ERG negative line), and no significant genes were found after RI-EIP1 treatment by applying the same criteria (greater than 2-fold, FDR<0.01) (FIG. 20G-H), clearly demonstrating that the significant genes suppressed by RI-EIPs in VCaP cells (an ERG positive line) are indeed relevant to the ERG-mediated pathway. Gene Set Enrichment Analysis (GSEA) of down-regulated genes in RI-EIP1-treated cells were also negatively enriched in siERG VCaP cells (FDR<0.01) (FIG. 5F), indicating that RI-EIP treatment has a direct effect on ERG-mediated transcription in VCaP cells.

Figure 5G:
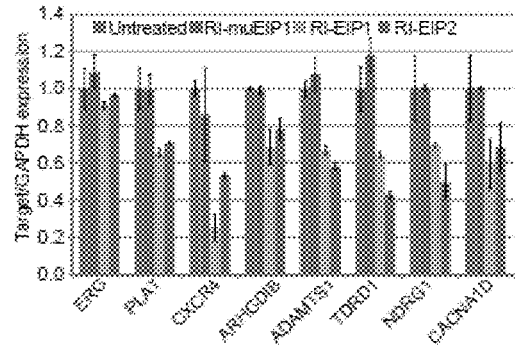

To validate the microarray data, several down-regulated genes that harbor multiple ETS binding sites in their promoter region were selected (FIG. 5C), and their expression was measured following peptide treatment. Consistent with the microarray data, quantitative RT-PCR results showed target gene expression was reduced in peptide-treated cells relative to controls (FIG. 5G). Collectively, these data indicate that the retroinverso peptidomimetics have similar effects as siERG knockdown in VCaP cells.

Retroinverso EIPs Suppress Tumor Growth In Vivo

Figure 21A:
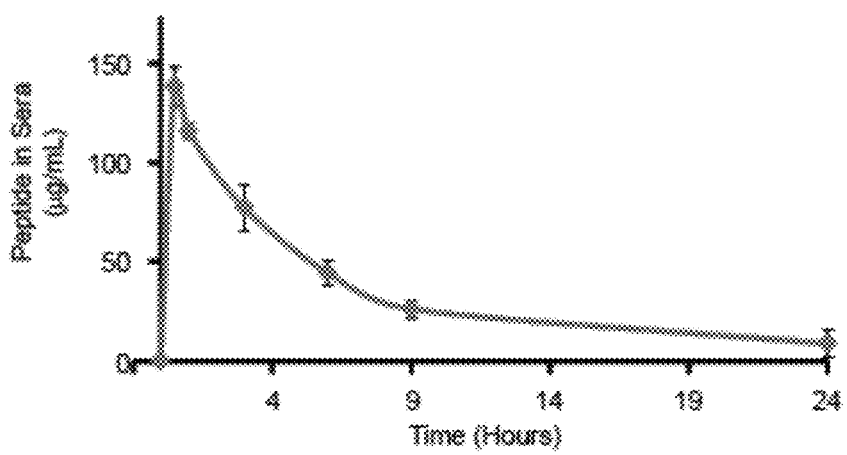
FIG. 21A-Q shows xenograft tumor response after treatment with the peptidomimetics. (A) The serum concentration of biotinylated RI-EIP1 after intraperitoneal administration of 25 mg/kg in mice harboring VCaP xenografts was assessed by colorimetric assay (graph shows results from a representative sample). (B) VCaP xenograft tumors treated with a single dose of 25 mg/kg RI-EIP1 were harvested at 3, 6, 18, 24 hours followed by IP-Western blot analysis with anti-DNA-PKcs antibody. (C) Immunoblot analysis of ERG and GAPDH in VCaP xenograft tumors treated with 25 mg/kg RI-EIP1 or RI-muEIP1 daily for 5 days. (D-E) Tumor volumes (in mm3) for each VCaP-xenografted mice treated with RI-EIP1 or RI-muEIP1 for 18 consecutive days as in FIG. 6D. (F) VCaP-xenografted mice treated with RI-EIP1 or RI-muEIP1 for 24 consecutive days at various doses as indicated. (G) VCaP xenografted mice treated with RI-EIP2 or RI-Scr at indicated time points. (H-I) Body weight of mice after long-term treatment with RI-EIPs. (J) Measurement of serum markers of toxicity in mice harboring xenografts treated for 24 consecutive days by either RI-EIP1 or RI-muEIP1. (K) Sequence alignment of ERG and ETV1. (L) Interaction of EIP with endogenous ETV1 protein expressed in LNCaP cells. Biotin-EIP1 or biotin-muEIP1 was incubated with LNCaP cell lysates. (M-N) Confluence rates for LNCaP cells were measured by IncuCyte; cells were treated with (M) RI-EIP1 or (N) RI-muEIP1 as indicated. (O) Boyden chamber transwell invasion assays were performed in chambers pre-coated with Matrigel. (P) Immunoblot analysis of ETV1 and GAPDH from LNCaP cell treated with RI-EIP1/2 or RI-muEIP1 at indicated concentrations. (Q) Quantitative PCR was used to assess the relative expression of several ERG target genes in VCaP xenograft tumors in FIG. 6D.
Figure 21B:
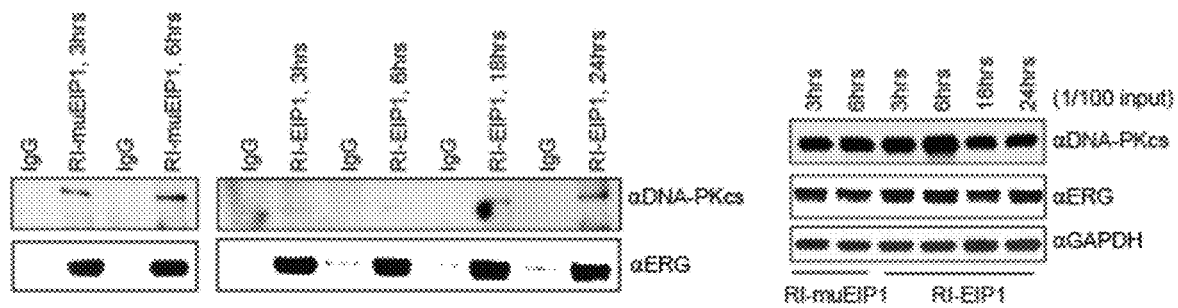

To assess the basic pharmacokinetic and pharmacodynamic properties of RI-EIP1 in vivo, the permeability and stability of the peptidomimetic was tested upon intraperitoneal (IP) administration in mice. VCaP xenografted mice were injected with a single dose of 25 mg/kg biotinylated RI-EIP1 and serum and tumors were collected at varying time intervals as indicated. Results showed that serum peptide levels reached a peak at 30 minutes after IP injection (FIG. 21A) and was still detectable in the serum up to 24 hours post-injection. Co-immunoprecipitation followed by immunoblot analysis demonstrated that a single 25 mg/kg dose of RI-EIP1 blocked the ERG:DNA-PKcs interaction at 3 and 6 hours post RI-EIP1 injection (FIG. 21B).

Next, RI-EIP1 was tested in ERG-mediated invasion and metastasis in vivo using two established models. TMPRSS2:ERG-positive VCaP cells were implanted onto the upper chorioallantoic membrane (CAM) of a fertilized chicken embryo and the relative number of cells that invade and intravasate into the vasculature of the lower CAM after treatment with the RI-EIPs was investigated (Kim et al., Cell 94, 353-362 1998). RI-EIP1 dramatically blocked both ERG-mediated invasion and intravasation (p=0.05) (FIG. 6A-B). The lungs were harvested and the number of metastasized VCaP cells was measured; as shown in FIG. 6C, RI-EIP1 treatment dramatically reduced lung metastases from VCaP tumors (p=0.03), demonstrating the efficacy of RI-EIPs.

Figure 6D:
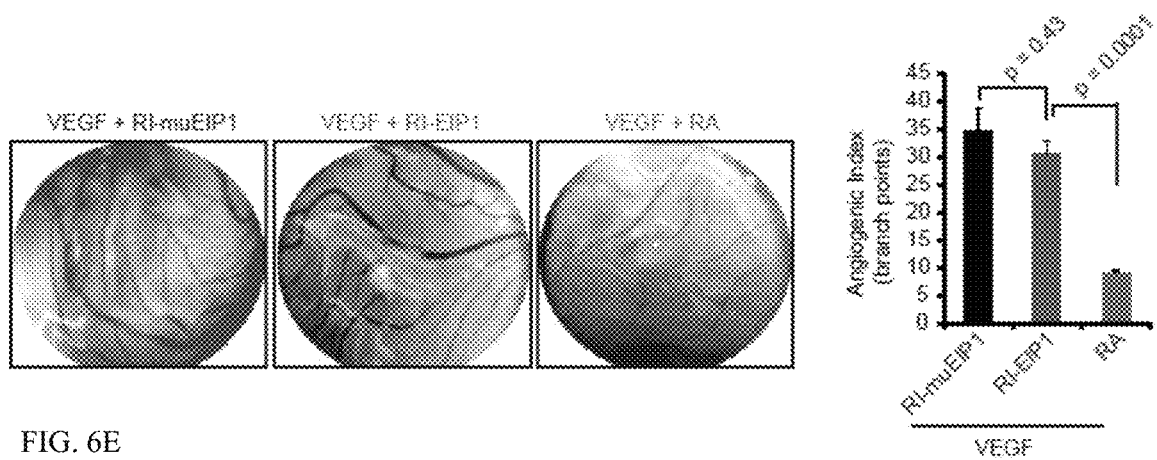
Figure 6E:
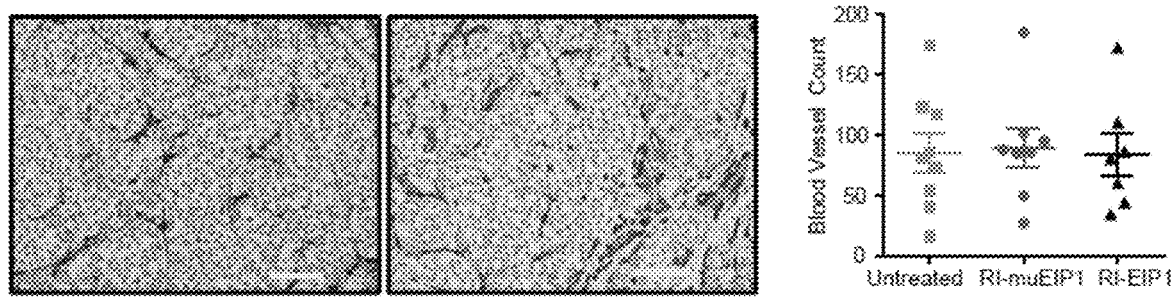
Figure 7A:
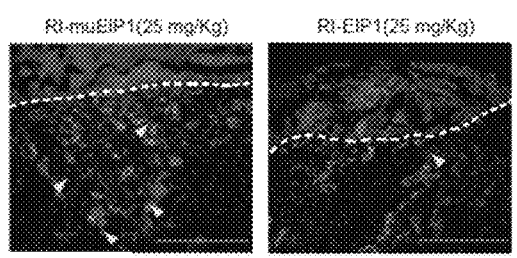
FIG. 7A-I shows that retroinverso EIPs suppress tumor growth in vivo. (A) Chicken chorioallantoic membrane (CAM) invasion assays were performed using VCaP cells that stably overexpress Cherry Red (red fluorescence emission). (B, C) CAM intravasation (B) and lung metastasis (C) assays were performed on VCaP CAM xenografts. (D) VCaP-xenografted mice were treated with RI-EIP1 or RI-muEIP1 at indicated doses for 18 consecutive days. (E) Kaplan-Meier survival data plotted as percent of animals surviving in each group using a predefined cutoff tumor volume of 1,500 mm3. (F) PC3-xenografts mice were treated with 25 mg/kg RI-EIP1 or RI-muEIP1, and average tumor volume was calculated as in (D). (G) An ETV1-positive human primary prostate cancer serial xenograft was treated as in (D). (H) Immunoblot analysis of ERG, DNA-PKcs, and GAPDH in VCaP xenograft tumors treated with 25 mg/kg RI-EIP1 or RI-muEIP1 24 hours after the final treatment in (D). (I) Schematic depicting the mechanisms of EIPs therapeutically targeting TMPRSS2:ERG fusion products in prostate cancer.
Figure 7B:
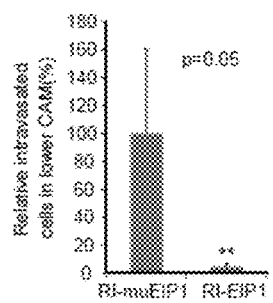
Figure 7C:
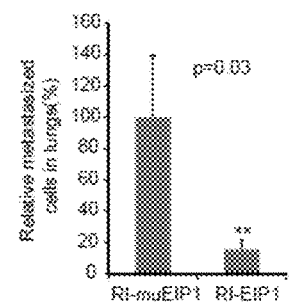
Figure 7D:
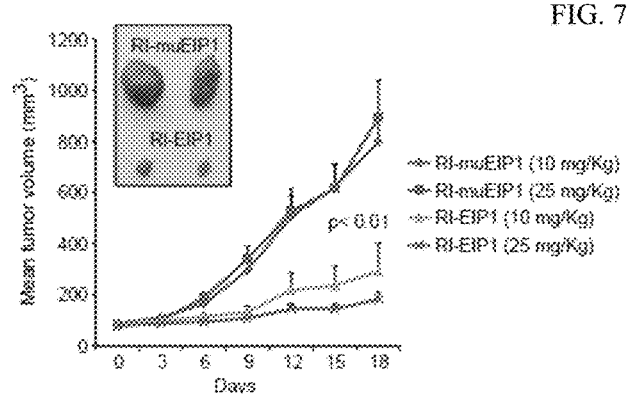
Figure 7E:
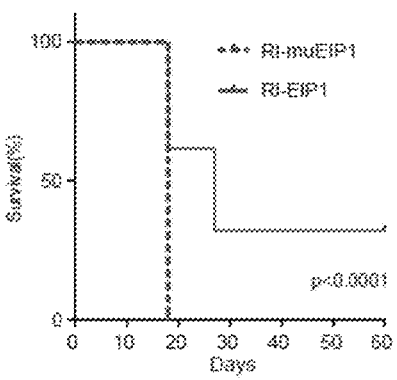
Figure 7F:
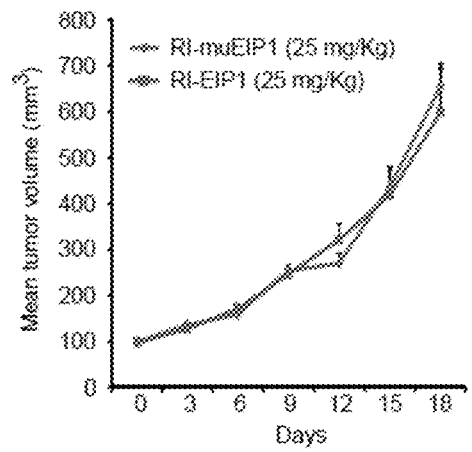
Figure 7G:
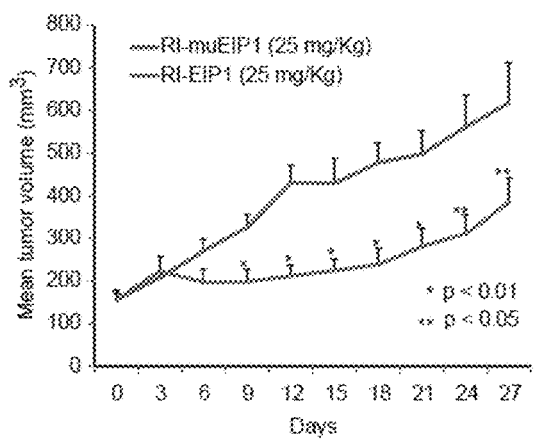
Figure 7H:
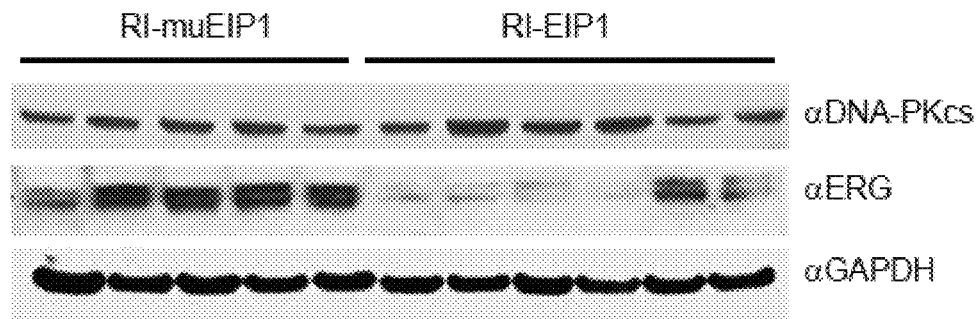
Figure 7I:
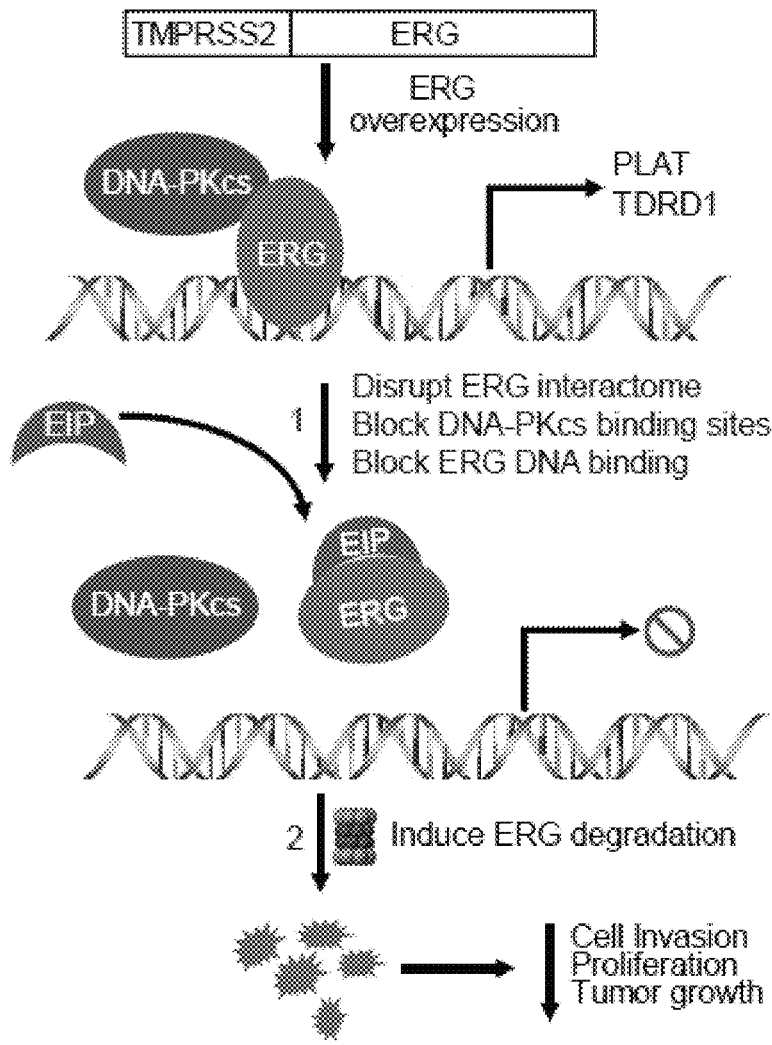
Figure 21C:
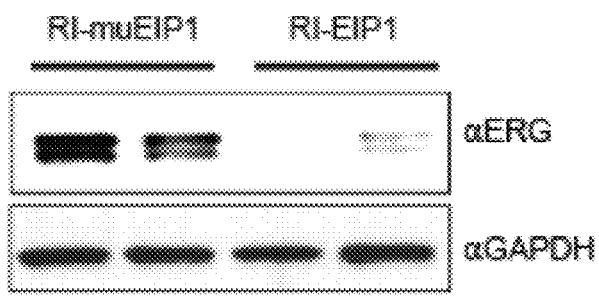
Figure 21D:
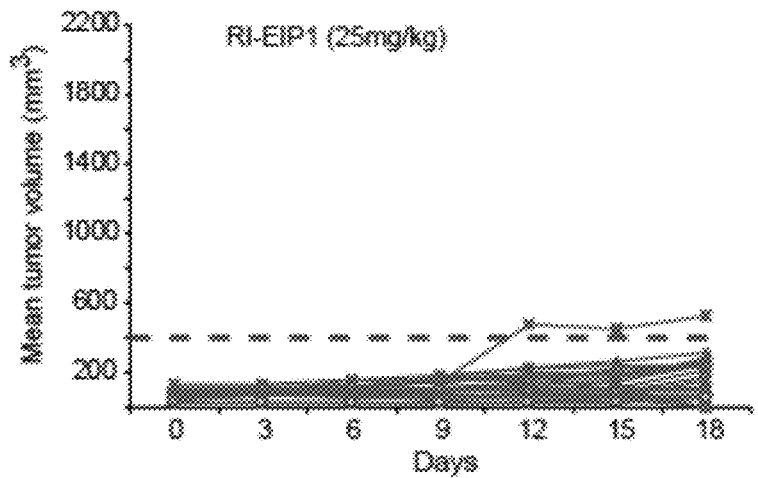
Figure 21E:
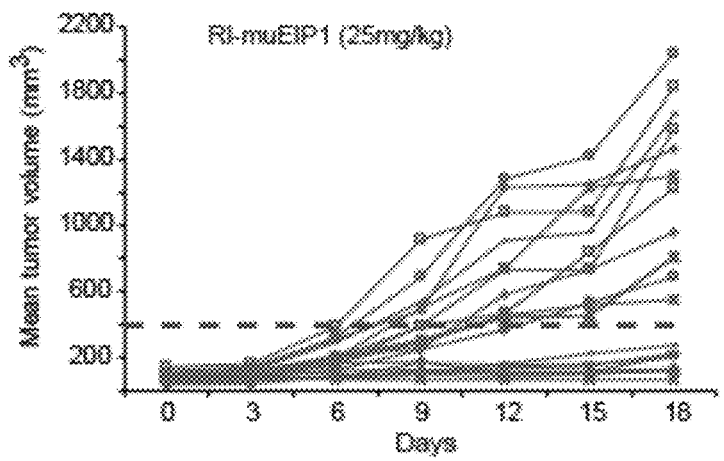
Figure 21F:
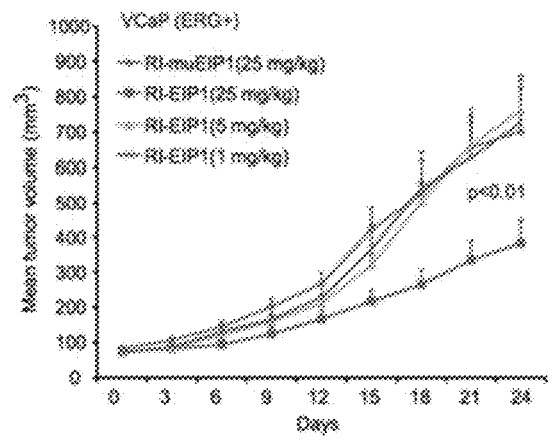
Figure 21G:
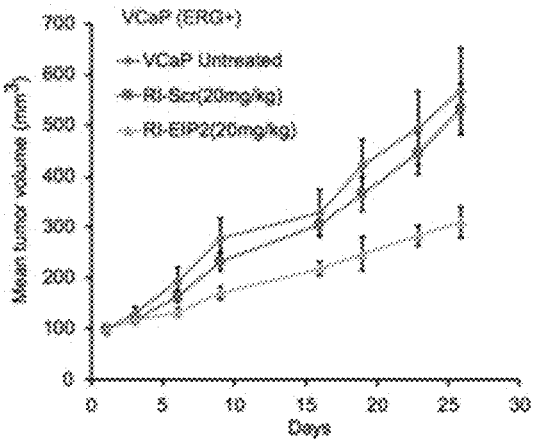

VCaP (ERG fusion-positive) or PC3 (ERG fusion-negative) cells were implanted in male athymic nude mice and the effect of RI-EIP1 on tumor growth was studied. The effects of EIPs on ERG protein degradation in the in vivo model at early time points was investigaed. The VCaP-xenografted mice were treated with 25 mg/kg RI-EIP1 or RI-muEIP1 daily for 5 days. The tumors were then collected at day 7 and immunoblot analysis showed that RI-EIP1 was able to degrade ERG protein, while control peptide had no effect (FIG. 21C). Mice with palpable tumors were randomized to receive either 25 mg/kg per day (n=10) or 10 mg/kg (n=10) of the retroinverso peptidomimetics. A dose-dependent reduction of VCaP tumor growth in RI-EIP1-treated mice relative to those treated with mutant peptide (p<0.01) was observed at day 18 (FIG. 6D). Among the high dosage group (25 mg/kg RI-EIP1), 10% (2/20) of the tumors had completely regressed with no palpable tumor at day 18 (FIG. 21D-E). The group was treated with RI-EIP1 over an extended period of time and it was found that 35% (7/20) of the tumors showed no signs of recurrence at day 30. These mice were then maintained for an additional 30 days without therapy and no recurrences were observed (FIG. 6E). Additional VCaP xenograft studies were performed using varying doses of RI-EIP1, 1 mg/kg, 5 mg/kg and 25 mg/kg and significant suppression of tumor growth was observed at 25 mg/kg dose relative to control (FIG. 13F). RI-EIP2-treated VCaP xenografts also significantly delayed tumor growth at 20 mg/kg dose (p<0.01) (FIG. 13G) consistent with biochemical and in vitro studies.

Figure 21H:
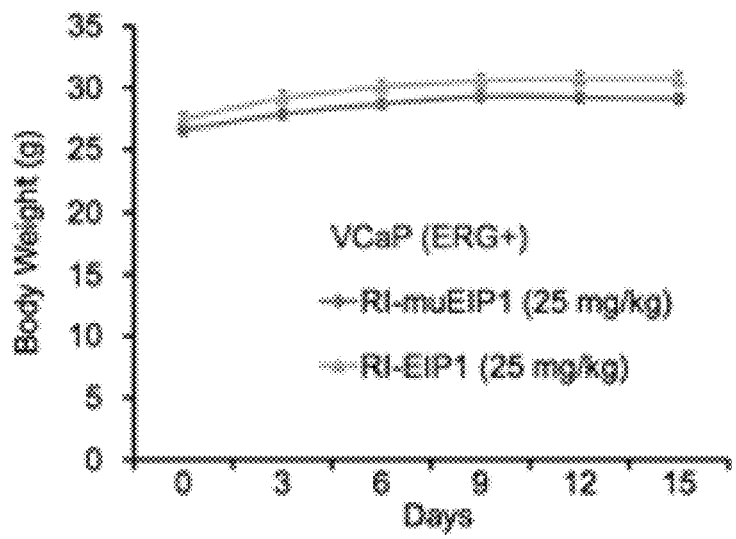
Figure 21I:
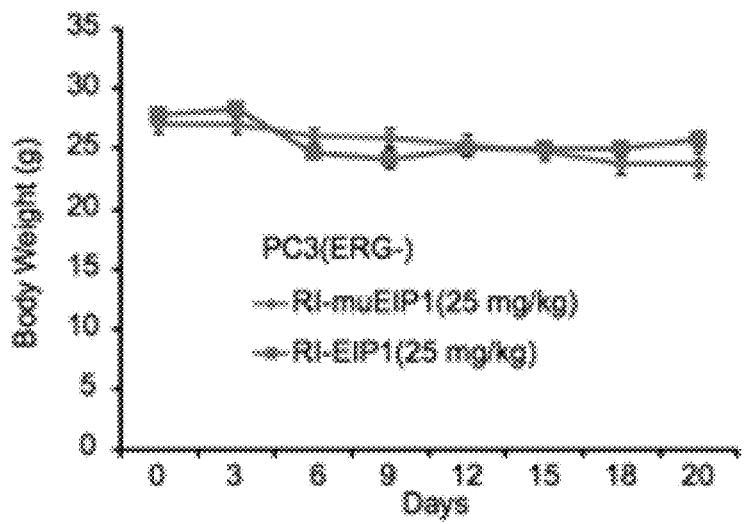
Figure 21J:
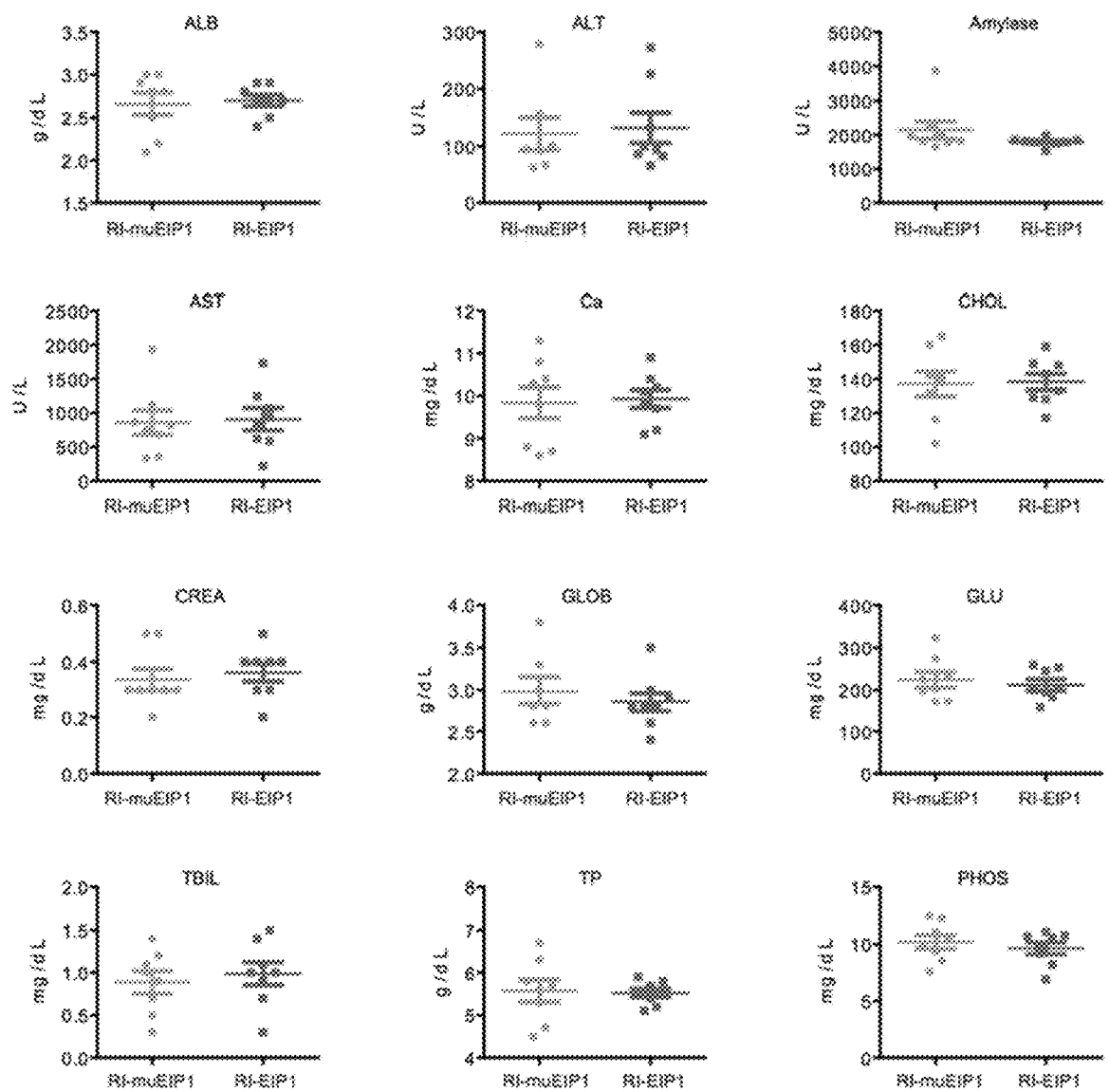

The effect of RI-EIP1 was specific to ETS-positive xenografts as no difference in tumor size was observed for PC3 xenografts treated with RI-EIP1 compared to mutant peptidomimetic (FIG. 6F). Peptidomimetics at doses up to 25 mg/kg did not significantly affect body weight (FIG. 21H-I) or markers of liver toxicity as measured by serum aspartate aminotransferase (AST) and alanine aminotransferase (ALT) levels (FIG. 21J).

Given the magnitude of the effects of EIPs on the TMPRSS2:ERG harboring tumors, the study was extended to ETV1-positive cancers. Sequence alignment showed high homology in the ETS domains of both ERG and ETV1, particularly in the EIP binding region (FIG. 21K). In vitro assays demonstrated that the biotinylated EIP pulled down endogenous ETV1 from LNCaP cells (TMPRSS2:ETV1 rearranged prostate adenocarcinoma cells) in a dose-dependent manner (FIG. 21L). Further, the RI-EIPs, but not mutant peptides, significantly decreased the confluence rate of LNCaP cell growth (FIG. 21M-N) and attenuated LNCaP cell invasion in a dose-dependent fashion (FIG. 21O). Treatment of LNCaP cells with RI-EIP1 or RI-EIP2 significantly destabilized ETV1 protein at 48 hours post-treatment in a dose dependent manner, while control RI-muEIPs had no effect (FIG. 21P). RI-EIP1 was tested in an ETV1-positive, primary human prostate cancer (MDA-PCa-2b-T, FISH confirmed (Tomlins et al., 2008; supra)) propagated in serial xenografts (but not grown in vitro as a cell line). RI-EIP1 treatment significantly reduced tumor volume demonstrating that EIPs have potential to broadly treat ETS fusion-positive tumors (FIG. 6G).

IP-Western blot analysis was performed using tumor lysates from VCaP cell xenografts harvested after 18 days treatment (FIG. 6D) and a substantial degradation of ERG protein in RI-EIP1-treated xenografts compared to those treated with mutant peptide was found (FIG. 6H). Furthermore, qPCR analysis of 26 VCaP tumors demonstrated that RI-EIP1 treatment inhibited the gene expression of ERG targets such as TDRD1, ARHGDIB, NDRG1 and CACNA1D, but not TMPRSS2:ERG gene itself (FIG. 21Q) demonstrating that pharmacological doses can be achieved in vivo to disrupt ERG function.

Figure 22D:
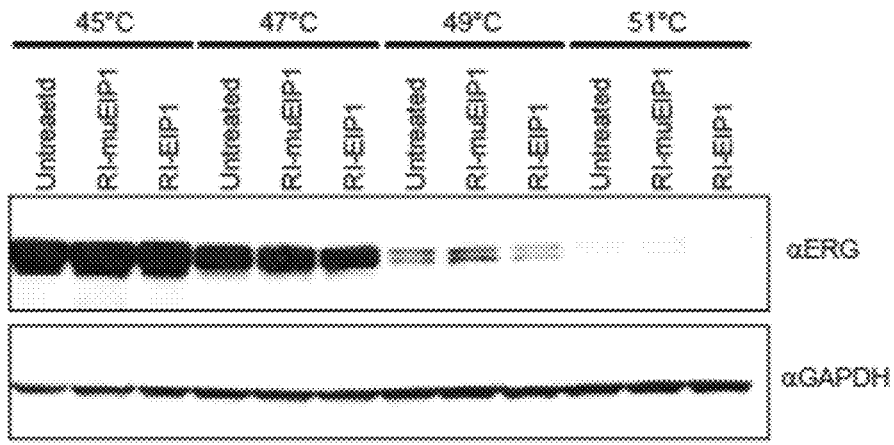
Figure 22E:
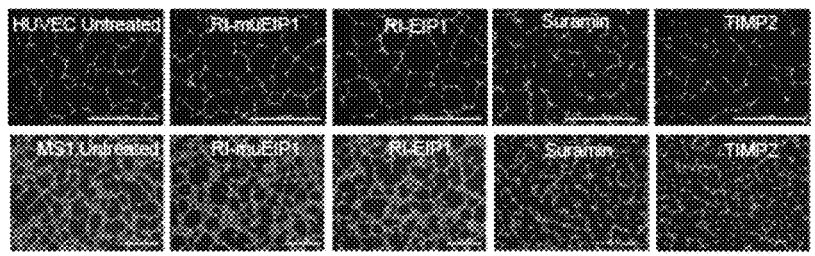
Figure 22F:
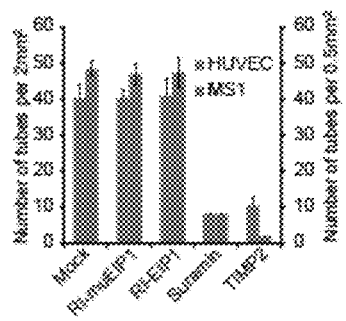
Figure 22G:
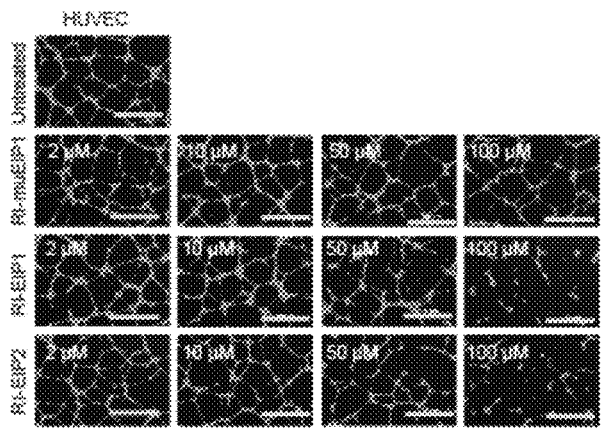
Figure 22H:
Figure 22I:
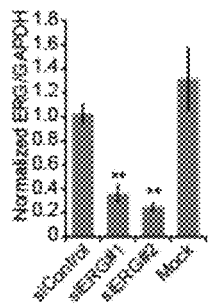

It was then determined whether RI-EIP affects normal ERG function. Pull-down experiments were performed using whole cell lysates of VCaP, human (HUVEC) or mouse (MS1) endothelial cells, all of which express high levels of ERG, revealed that the EIPs preferentially bound to pathogenic, over-expressed ERG fusion product in cancer cells over wild-type ERG expressed in human or murine endothelial cells (FIG. 22A). Using cell lysates normalized for ERG levels (FIG. 22B), pull-down experiments showed that biotinylated EIP1 bound more efficiently to VCaP ERG than HUVEC ERG (0.25 mg/ml vs 8 mg/ml) (FIG. 22C). Furthermore, while CETSA demonstrated that RI-EIP1 binds to thus increasing the thermal shift of ERG fusion protein in VCaP cells (FIG. 4F), there was a clear difference in the soluble ERG protein in VCaP (cancer) cells versus HUVEC (normal) cells (FIG. 22D).

Figure 22J:
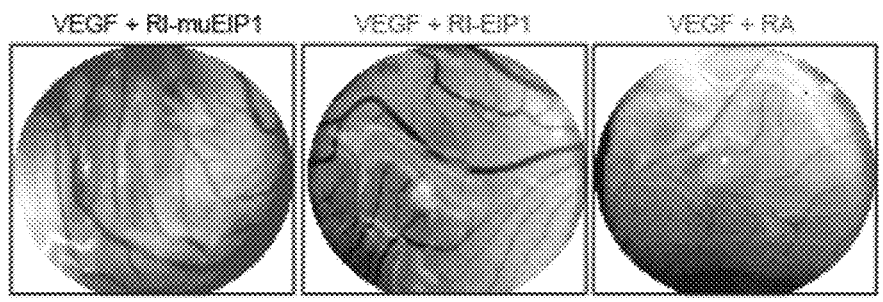
Figure 22K:
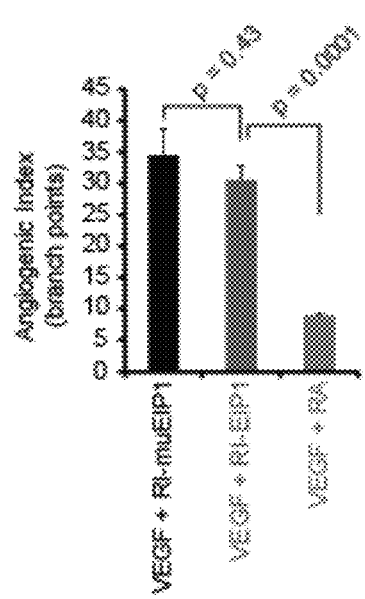
Figure 22L:
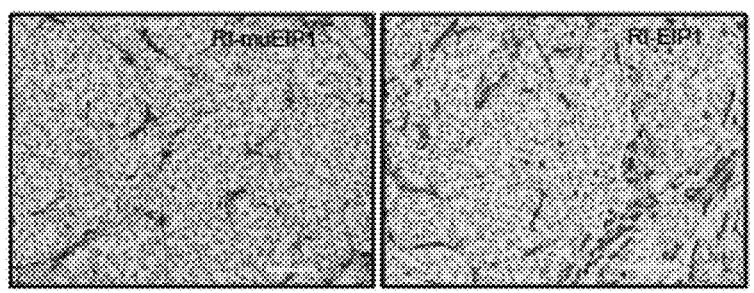
Figure 22M:
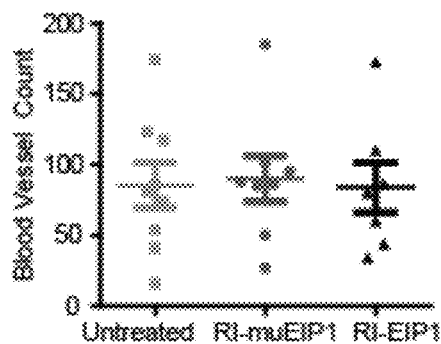

The effects of peptidomimetic treatment on ERG-regulated biological processes (Birdsey et al., Blood 111, 3498-3506 2008; McLaughlin et al., Blood 98, 3332-3339 2001) such as endothelial tube formation and angiogenesis was evaluated. RI-EIP1 treatment at 10 M did not have a significant effect on either HUVEC or MS1 cell tube formation compared to ERG knockdown in HUVEC cells (FIG. 22E-I). Further, RI-EIP1 treatment did not alter angiogenesis in vivo as assessed by CAM angiogenesis assays (FIG. 22J-K) or by scoring the number of CD31$^+$ vessels in FFPE sections of VCaP xenograft tumors (FIG. 22L-M).

TABLE 1

Binding affinity of the synthetic peptides determined by OctetRED, relate to FIG. 1.

| Synthetic peptides | SEQ ID NO: | Name | Kd (µM) |
|---|---|---|---|
| LPPYLFT | 4 | EIP1 | 0.6 |
| FSASSPA | 70 |  | 21.1 |
| FSFGSLP | 71 |  | 2.1 |
| LSFGSLP | 2 | EIP2 | 1.8 |
| LAFGSLP | 72 |  | 6.4 |
| FTFGSLP | 73 |  | 3.9 |
| LTFGSLP | 74 |  | 2.9 |
| MTFGTLP | 75 |  | 4.6 |
| YTFGTLP | 76 |  | 3.2 |
| LRFGTLP | 77 |  | 7.9 |
| LSFGSFP | 79 |  | 12.5 |
| LSFGTFP | 79 |  | 9.2 |
| LPPALFT | 111 | muEIP1 | N.D. |
| LSAGSAP | 112 | muEIP2 | N.D. |
| LPPTFLY | 113 | Scr | N.D. |

N.D.: not determined.

Example 2

Interaction of EIP Peptides with Other ETS Family Members

ETS-related gene (ERG) is a member of the ETS transcription factor gene family. The ETS family consists of 28 unique genes of which ERG, FLI1 and ETV1 are the most frequently deregulated in cancer (Molecular Pathways: Targeting ETS Gene Fusions in Cancer, Feng F Y et al., 2014 Clinical Cancer Research). In addition to the TMPRSS2: ERG fusion present in 50% of prostate cancers, the TMPRSS2:ETV1 fusion is present in 5% of these tumors. In addition, oncogenic fusions in Ewing Sarcoma comprise chromosomal translocations yielding in-frame fusions of the amino terminus of the EWS gene and the carboxyl terminus of an ETS gene that contains the DNA-binding domain. The ETS gene is Fli1 in 85% of tumors, ERG in 10%, and ETV1, ETV4 or FEV in the remaining 5% of tumors. Aberrant EWS-ERG proteins show altered DNA binding and transcriptional activation properties compared to normal ERG proteins. Moreover, in a subset of acute myelogenous leukemia, chronic myelogenous leukemia in BLAST crisis, and certain myelodysplastic syndrome, the N-terminal region of TLS (translocation liposarcoma) is fused to the C-terminus of ERG through a recurrent t(16;21) translocation. This TLS-ERG chimeric protein has also been reported in Ewing's sarcoma. The TLS-ERG chimeric protein retains the N-terminal domain of TLS that is fused to the DNA-binding domain of ERG.

Figure 11:
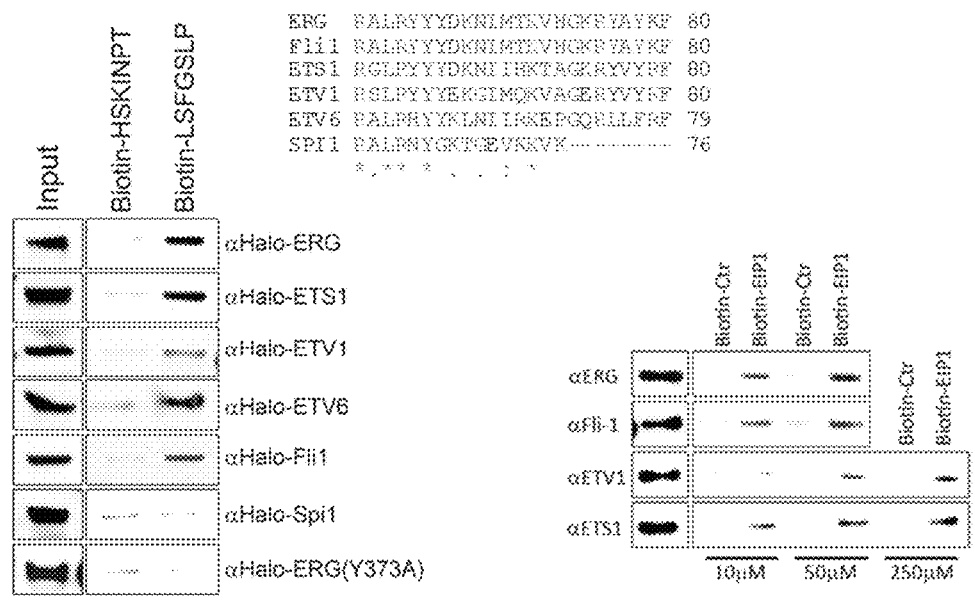
FIG. 11 shows that peptides of embodiments of the present disclosure pull down ETS family member polypeptides.
Figure 18D:
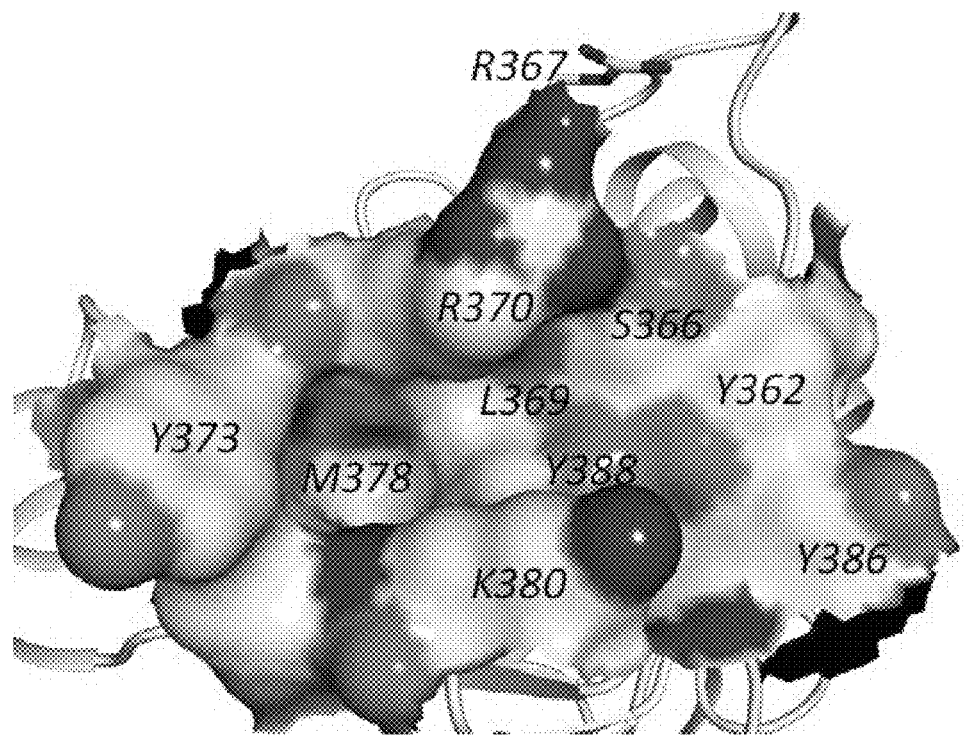
Figure 18E:
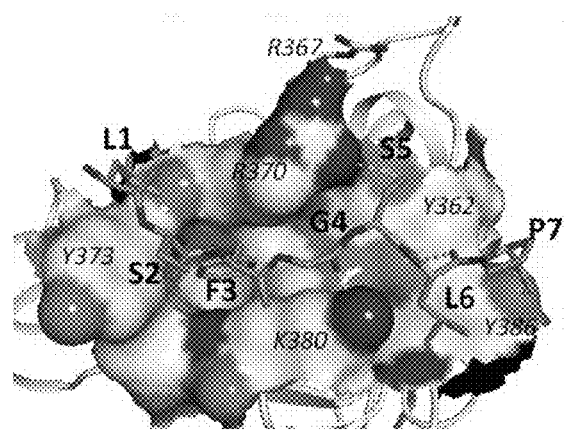
Figure 18F:
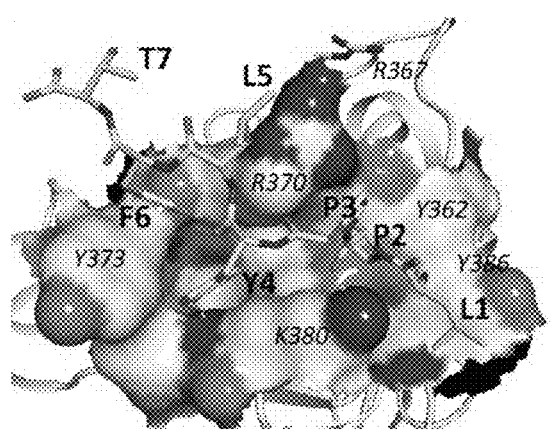

Experiments were conducted to determine if the EIP peptides described herein could interact with the DNA-binding domain of other ETS family members. A sequence comparison of the DNA-binding domain of ERG, Fli1, ETS1, ETV1, ETV6, and SPI1 as shown in FIG. 11 was performed to establish sequence similarity.

In order to perform binding experiments with EIP2 (Biotin-LSFGSLP), the full-length ERG, ETS1, ETV1, ETV6, Fli1, Spi1 and the ERG mutant Y373A were expressed as fusion proteins with a Halo-tag at the N-terminus. Halo fusion proteins were expressed using the TNT® SP6 High-Yield Wheat Germ kit (Promega) following the manufacturer's protocol. Halo-tagged ETS proteins were incubated with the control peptide Biotin-HSKINPT or the biotinylated EIP2 peptide Biotin-LSFGSLP and pull-down experiments were performed as indicated in FIG. 11. The biotin-LSFGSLP peptide was able to interact strongly with ERG, ETS1, and ETV6 DNA-binding domain, and to less extend with ETV1 and Fli1 DNA-binding domains. No interaction was detected with Spi1 or the negative control ERG (Y373A). Similar interactions were observed between Biotin-EIP1 peptide (Biotin-LPPYLFT) and the full-length ERG, Fli1, ETV1, and ETS1 in a dose dependent manner.

Example 3

Truncated and Modified EIP Peptides

Modifications and mutations were performed on the EIP1 peptide (LPPYLFT) to better understand which amino acids contributed to binding to ERG. Each terminus was modified by capping both with acetyl at the N-terminus and amide at the C-terminus. Capping of the EIP1 peptide at both the N- and C-terminus abolished binding to ERG (FIG. 13). Some of the binding was recovered by mutating the Y at position four to E or K (Kd of 3.6 and 4.3 µM respectively). Moreover, mutation of L at position five to E in the capped peptide also partially restored binding to ERG (Kd=5.1 µM).

Methods and Materials

Peptides were synthesized by employing Fmoc solid phase peptide synthesis strategy prepared either manually or by ABI 433A peptide synthesizer. After completion of synthesis, the peptides were cleaved from the resin using cleavage solution, concentrated, and precipitated with ether. The precipitates were collected and purified by HPLC.

| | |
|---|---|
| Resin | Nova PEG Rink amide (C-terminal capped) Chloro-trityl chloride (C-terminal free) |
| Coupling reagent | 0.45M HBTU/HOBt in DMF, 2M DIEA in NMP (ABI). DIC/HOBt in DMF (manual) |
| Deprotecting solution | Piperidince (100% ABI, 20% in DMF manual) |
| Cleavage solution | 92.5% TFA, 5% H$_2$O, 2.5% TIS |

Results

Based on studies using Alanine scanning on the 7-mer EIP1 peptide, the importance of the PYL residues for binding to ERG was identified. One amino acid at a time was truncated from either the N- or the C-terminus of the 7-residue EIP1 peptide until the trimer PYL was reached. Additionally, each terminus was modified by capping one or both with acetyl at N-terminus or amide at C-terminus. According to the OctetRed data generated and presented in FIG. 14, the most potent truncated peptides are 4PL-A (Ac-PPYL-NH$_2$) containing the PPYL sequence and with capping at both N- and C-terminus (Kd=2.24 µM), and 5PT-N(NH$_2$-PYLFT-NH$_2$) containing the PYLFT sequence and capping at the C-terminus. N- and C-terminal modifications for the 7-, 4-, and 3-mer peptides were generated and the data is presented in FIG. 15. For the 7-mer peptide (LPPYLFT), capping at the C-terminus abolishes binding, while capping or not at the N-terminus does not seem to have an effect. For the 4-mer peptide (PPYL), only the N- and C-terminus capped peptide displayed binding similar to the 7-mer peptide. For the 3-mer peptide (PYL), only the N-terminal capped peptides showed binding independently of modifications at the C-terminus, but binding affinity was lower than the 4-mer peptide. Therefore, the 4-mer peptide PPYL was selected for further characterization.

Since the 4PL-A (Ac-PPYL-NH$_2$) sequence is fairly hydrophobic, the addition of hydrophilic groups on prolines (Hydroproline, Hyp) or to the N-terminus (4-methylpiperazine, Pip) of 4PL-A were made to increase solubility; 3-Alanines were added as a spacer (FIG. 16). The Hyp modifications disrupted binding (NB: no binding). Mutation of PPYL to PPYE also abolished binding. The addition of 4-methylpiperazine (Pip) to the PPYL or the LPPYLFT sequences resulted in a more soluble version of 4PL-A and EIP1 peptides that bound ERG in a comparable range with 4PL-A and EIP1 (Kd~2-3 µM). The PPYL peptide was also used as a template for mutation studies (FIG. 17). Mutation of Leu using unnatural amino acids bearing larger hydrophobic side chains did not show any improvement on binding to ERG. Removal of —OH on Tyr had little effect on binding, but increasing the size of the aromatic ring or inserting a Cl atom was detrimental.

Example 4

Chemistry

This example describes exemplary peptide chemistry and synthesis of exemplary peptides of embodiments of the present disclosure. Exemplary methods are described in, for example "Peptide Synthesis and Applications (Methods in Molecular Biology" 2$^{nd}$ Edn., Ed Jensen K. J Shelton, P. T. and Pedersen S. L., Humana Press 2013; "Fmoc Solid Phase Peptide Synthesis: A Practical Approach" 1$^{st}$ Edn.' Ed. Chan, W. C. and White P. D., Oxford University Press 2000; "Chemistry of Peptide Synthesis" Benoiton N. L., CRC Press 2005; and "Peptides: Synthesi, Structures and Applications" Ed Gutte B., Academic Press 1995; Chem Reviews 104, 5823 (2004); Acct Chem Res 41, 1331 (2007), Amino Acids, Peptides and Proteins in Organic Chemistry Vol 1, 245-289 Wiley-VCH Verlag 2009; Amino Acids 38, 829 (2010), J Org Chem 65, 8704 (2000), Org Biomol Chem 5, 2138 (2007) Tetrahedron Asym 9, 3517 (1998)); each of which is herein incorporated by reference in its entirety.

In some embodiments, in order to mix sequences of normal amino acids, and retro sequences in the same peptide, either diacids or diamines are used as linkers between the two orientations. Malonate esters, with an appropriate side chain mimicking an amino acid are useful diacid linkers, and such compounds may be prepared chirally from the corresponding racemic malonate dimethyl ester and pig liver esterase (J Org Chem 75 1612 (2010)) and stitched sequentially into the peptide. The racemic malonates can also be C-methylated prior to enantioselective hydrolysis or resolution through classical salt formation or simulated moving bed chromatography. Use of an oxalate derivative will shorten the space between the two segments, and make the peptide less flexible, whereas use of a simple longer diacid such as succinic acid will leave the linker between the two segments more flexible. Diamines can also act as linkers between segments of opposite orientation, and can be unsubstituted or they can contain the normal amino acid side chains with chirality specified, for example as 1,1-diamino compounds, derived from amino acids already partially incorporated into a peptide chain (EP 0384523 (1990)), or 1,2-diamines derived from amino acids by selective reduction-amination sequences (Letters in Peptide Sciences 9, 187 (2003); Tetra Letters 47, 1717 (2006)).

Adding modules onto amino acid side chains, for example attaching a PSTM to the lysine via reductive amination or to a cysteine via a disulfide bond formation, involves the selective manipulation of side-chain and main chain protecting groups. Such reactions are described in, for example, Amino Acids, Peptides and Proteins in Organic Chemistry Vol 4, 1-97 Wiley-VCH Verlag 2011, and Solid-Phase Synthesis 129-195 Marcel Dekker 2000, which are herein incorporated by reference in their entirety.

The use of reactive amino acid side chains on various, antibody constructs to link to small molecule therapeutics is well precedented with many such conjugates entering the clinic. Prostate targeted immunoconjugates for PSMA, PSCA and STEAP1 have entered the clinic (Immunotherapy 5, 1347 (2013)). Methods for conjugation of small molecules to antibodies and antibody fragments are well developed, and described extensively in the literature (Methods in Molecular Biology Vol 1045 "Antibody-Drug Conjugates" Ed Ducry L., Springer 2013.)

Targeting the LHRHR and GRPR receptors involves the use of standard peptide ligands and has been extensively reviewed in the literature LHRHR Int J Peptides & Protein Res 17, 72 (1981); Proc Natnl Acad Sci USA 93, 7269; Clin Cancer Res 9, 4505 (2003); GRPR Curr Pharm Design 14, 3033 (2008); ibid 19, 3329 (2013); Nature Rev Urology 10 235 (2013)), each of which is herein incorporated by reference in its entirety.

PSMA (FOLH1) is described, for example, in Eur J Nucl Med Mol Imaging 41, 89, 1280 (2014); J Med Chem 57, 2657 (2014); Prostate 74, 702 (2014)) and therapeutic approaches (J. Med Chem 51, 7737 (2008); Biomacromolecules, 15, 915 (2014); Bioorg Med Chem. 22, 4099 (2014); Bioorg Med Chem Lett 24, 2340 (2014)), each of which is herein incorporated by reference in its entirety.

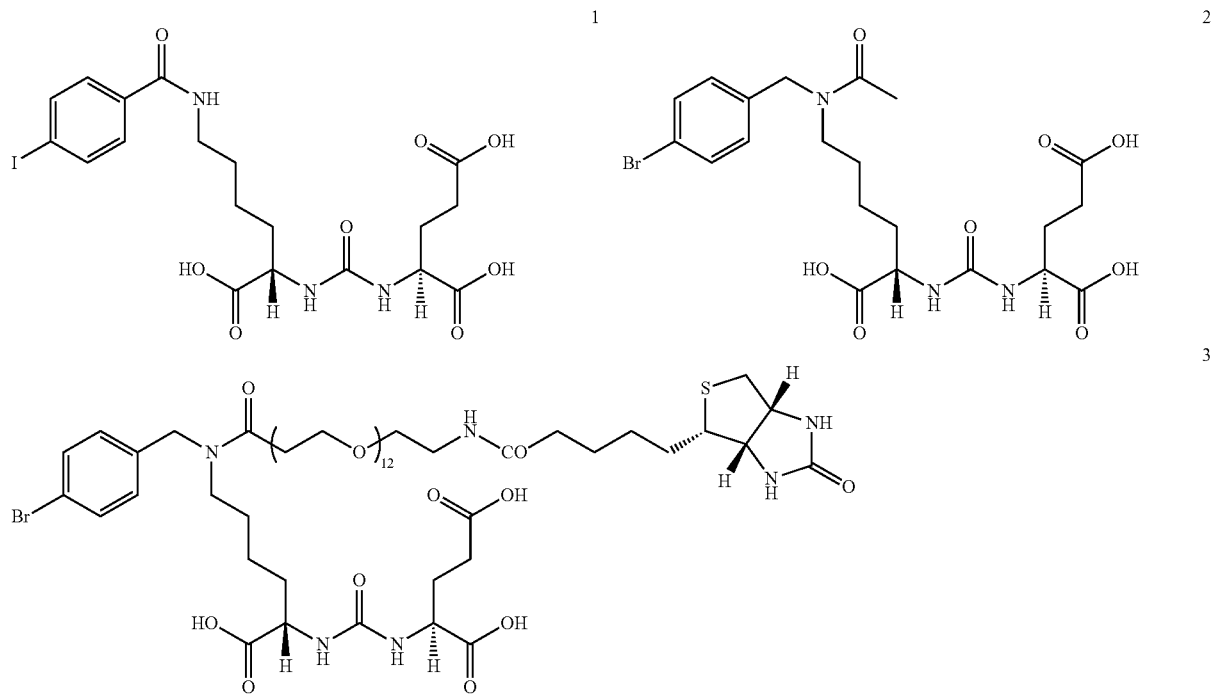

α,α'-Glu-Lys Urea-Based PSMA Ligands

Exemplary PSMA ligands are ureas of L-Glu and L-Lys, with an aromatic species on the e-lysine position. Compounds 1 (J Med Chem 51, 7737 (2008)) and 2 are reported to have $IC_{50}$s of 60 and 40 µM for PSMA Analogue 3, with a large tether, can be used to attach it to either a peptide or a nanoparticle such as a micelle or dendrimer has an $IC_{50}$ of 1.3 nM (2 & 3 Bioorg Med Chem. 22, 4099 (2014). Several similar systems have been described in the literature, with variants on both the Glu and the Lys being allowable whilst retaining nanomolar inhibition. Other tethering anchors have with 3-20 nM $IC_{50}$s for PSMA, and as several X-ray structures of small molecule inhibitors bound to PSMA are described.

Scheme 1. Synthesis of Polarized Linkers
Synthesis of Small Molecule PSMA-targeted Compounds

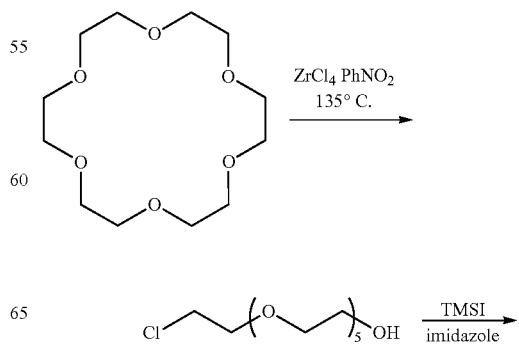

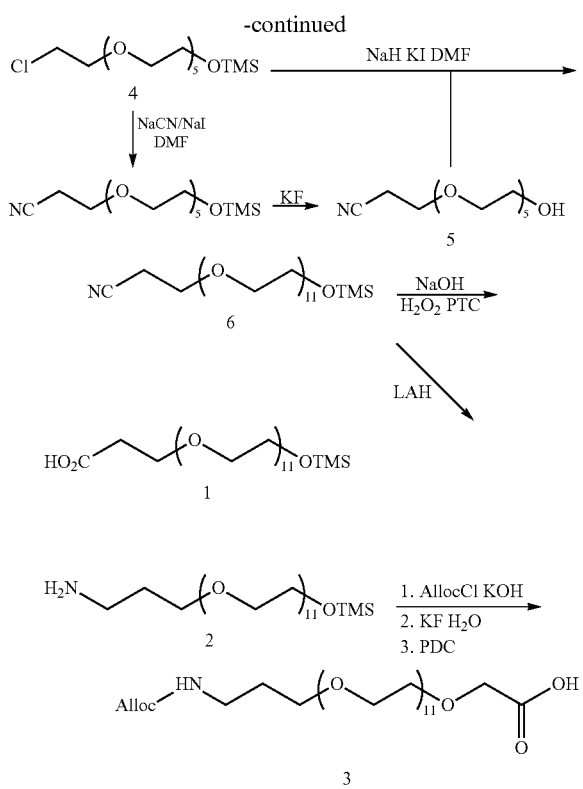

36-Trimethylsiloxy-4,7,10,13,16,19,22,25,28,31,34-undecyloxahexatriacontanoic acid 1

18-Crown-6 is efficiently cleaved to 17-chloro 3,6,9,12,15-pentaoxaheptadecan-1-ol by zirconium tetrachloride in nitrobenzene at 135° C. (Tet Letters 54, 4533 (2013)), and the alcohol is silylated under forcing, but near neutral conditions, with TMSI/imidazole to give the key silyl ether 4. Half of 4 is treated with NaCN, to form the corresponding nitrile, and the TMS ether is cleaved to give cyanoalcohol 5. Williamson ether synthesis couples 4 and 5 to give the long chain cyano-silyl ether 6. Treatment of 6 with basic hydrogen peroxide, in the presence of a phase transfer catalyst such as tetrabutylammonium bisulfate gives acid 1. Similarly, the silyl ether of 5 can be converted into a linker acid 18-trimethylsiloxy-4,7,10,13,16-pentaoxaoctadecanoic acid if so desired.

36-Trimethylsiloxy-4,7,10,13,16,19,22,25,28,31,34-undecyloxahexatriacontanyl-1-amine 2

Treatment of the long chain cyano-silyl ether 6 with lithium aluminum hydride gives amine 2. Similarly, the silyl ether of 5 can be converted into a linker amine 18-trimethylsiloxy-4,7,10,13,16-pentaoxaoctadecan-1-ylamine if so desired.

36-Amino-3,6,9,12,15,18,21,24,27,30,33-undecyloxahexatriacontanoic acid 3

Treatment of 36-trimethylsiloxy 4,7,10,13,16,19,22,25,28,31,34-undecyloxahexatriacontanylamine 2 with allyl chloroformate under Schotten-Baumann conditions gives the corresponding Alloc-protected amine. The silyl ether is then removed with fluoride ion, and the primary alcohol is oxidixed to the carboxylic acid with pyridinium dichromate to give 3. Alternatively the silyl group can as described below be directly oxidized to the aldehyde, which is then oxidized up to the carboxylic acid with NaClO$_2$ in dioxane. Use of the same chemistry on 18-trimethylsiloxy 4,7,10,13,16-pentaoxaoctadecan-1-ylamine gives the equivalent 18 atom linker.

Scheme 2. General Synthesis for N-Terminal PSMA-targeted EIP conjugated peptides 4. Di-O-tert-butyl (S,S)-2-(3-(6-(N-(4-bromobenzyl)amino)-1-(tert-butoxy)-1-oxohexan-2-yl)ureido)pentanedioate. 7

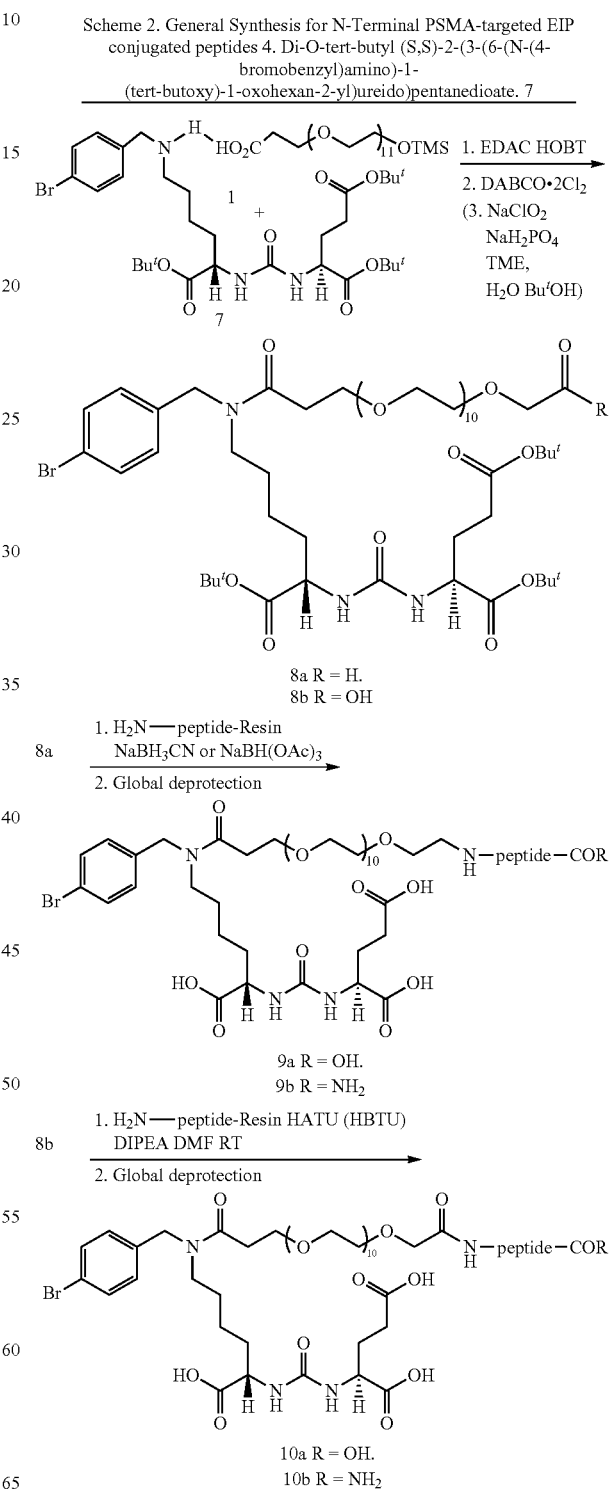

(S)-Glutamic acid di-t-butyl ester is reacted first with 0.34 equivalents of triphosgene and TEA in DCM at −78° C., and then allowed to warm to RT (J Amer Chem Soc 131, 17090 (2009)). Then O-t-butyl ε,N-benzyloxycarbonyl lysine hydrochloride and further triethylamine are added to form the α,Nα,N dipeptidyl urea. The Cbz group is removed under 1 atmosphere of hydrogen in MeOH containing 20% Pd/C at RT. Reductive amination of the free amine with 4-bromobenzaldehyde and NaBH$_3$CN and acetic acid in methanol produces 7 in moderate yield (Bioorg Med Chem 22, 4099 (2014)).

Di-O-tert-butyl (S,S)-2-(3-(6-[N-(4-bromobenzyl)-N-(1,36-dioxo-4,7,10,13,16,19,22,25,28,31,34-undecyloxahexatriacontanyl)amino]-1-(tert-butoxy)-1-oxohexan-2-yl)ureido)pentanedioate. 8a Secondary amine 7 and long chain acid 1 are reacted together with HOBT and EDAC to form the corresponding tertiary amide. The terminal silyloxy group is cleaved, and oxidized to an aldehyde to give 8a. This oxidation can be done in several ways, for example, the DABCO.chlorine (or bromine) complex. 18-trimethylsiloxy 4,7,10,13,16-pentaoxaoctadecanoic acid can also be used in this sequence to give the shorter 18 atom linker, with only 4 instead of 10 ethylene oxide repeats. Oxidation of either of these aldehydes under mild conditions (eg. NaClO$_2$, NaH$_2$PO$_4$, aqueous t-butanol/ACN, tetramethylethylene) to the corresponding acid 8b allows for the linker to be added to the peptide via an acylation reaction, rather than a reductive amination. N-Terminally PSMA Ligand-Tethered Amino-CPP-NLS-EIP Peptides. 9a/b.

A fully protected peptide is made by standard solid phase peptide synthesis (SPPS) using Fmoc/t-butyl technology (Int J Peptide Protein Res 35, 161 (1990)). Use of a normal resin leads to the C-terminal acid 9a after the final deblocking, whereas use of an aminated resin leads to the C-terminal amide 9b after the final deblocking. The N-terminal Fmoc protecting group is removed as normal, and the free amine is now reductively aminated with aldehyde 8, using either mildly acidic borohydride conditions (NaBH$_3$CN/AcOH NaBH(OAc)$_3$) or catalytic hydrogenation under mildly acidic conditions. The entire molecule is then globally deprotected with TFA (Methods Mol Biol 35, 63 (1994)), to give 9a/b after RP-HPLC purification.

The following compounds of structures 9a or 9b, which all incorporate combined CPP/NLS domains, and contain a single retro-inverso peptide chain are made via the process described above

```
Compound 9a-1:
peptide-CO2H is d-(GRKKRRQRRRGGPLSGFSL (SEQ ID NO:

35))

Compound 9a-2:
peptide-CO2H is d-(GRWRRRRNRRAQRGGPLSGFSL(SEQ ID

NO: 36))

Compound 9a-3:
peptide-CO2H is d-(GVKRKKKPGGPLSGFSL(SEQ ID NO:

37))

Compound 9a-4:
peptide-CO2H is d-(GRKKRRQRRRGGPFTGFTF(SEQ ID NO:

38))

Compound 9a-5:
peptide-CO2H is d-(GRWRRRRNRRAQRGGPFTGFTF(SEQ ID

NO: 39))

Compound 9a-6:
peptide-CO2H is d-(GVKRKKKPGGPFTGFTF(SEQ ID NO:

40))

Compound 9a-7:
peptide-CO2H is d-(GRKKRRQRRRGGTFLYPPL(SEQ ID NO:

41))

Compound 9a-8:
peptide-CO2H is d-(GRWRRRRNRRAQRGGTFLYPPL(SEQ ID

NO: 42))

Compound 9a-9:
peptide-CO2H is d-(GVKRKKKPGGTFLYPPL(SEQ ID NO:

43))

Compound 9a-10:
peptide-CO2H is d-(GRKKRRQRRRGGLYPP(SEQ ID NO:

44))

Compound 9a-11:
peptide-CO2H is d-(GRWRRRRNRRAQRGGLYPP(SEQ ID NO:

45))

Compound 9a-12:
peptide-CO2H is d-(GVKRKKKPGGLYPP(SEQ ID NO: 46))

Compound 913-1:
peptide-CONH2 is d-(GRKKRRQRRRGGPLSGFSL(SEQ ID NO:

35))

Compound 9b-2:
peptide-CONH2 is d-(GRWRRRRNRRAQRGGPLSGFSL(SEQ ID

NO: 36))

Compound 9b-3:
peptide-CONH2 is d-(GVKRKKKPGGPLSGFSL(SEQ ID NO:

37))

Compound 9b-4:
peptide-CONH2 is d-(GRKKRRQRRRGGPFTGFTF(SEQ ID NO:

38))

Compound 9b-5:
peptide-CONH2 is d-(GRWRRRRNRRAQRGGPFTGFTF(SEQ ID

NO: 39))

Compound 9b-6:
peptide-CONH2 is d-(GVKRKKKPGGPFTGFTF(SEQ ID NO:

40))

Compound 9b-7:
peptide-CONH2 is d-(GRKKRRQRRRGGTFLYPPL(SEQ ID NO:

41))

Compound 9b-8:
peptide-CONH2 is d-(GRWRRRRNRRAQRGGTFLYPPL(SEQ ID

NO: 42))
```

Compound 9b-9:
peptide-CONH₂ is d-(GVKRKKKPGGTFLYPPL(SEQ ID NO: 43))

Compound 9b-10:
peptide-CONH₂ is d-(GRKKRRQRRRGGLYPP(SEQ ID NO: 44))

Compound 9b-11:
peptide-CONH₂ is d-(GRWRRRRNRRAQRGGLYPP(SEQ ID NO: 45))

Compound 9b-12:
peptide-CONH₂ is d-(GVKRKKKPGGLYPP(SEQ ID NO: 46))

N-Terminally PSMA Ligand-Tethered Amido-CPP-NLS-EIP Peptides. 10a/b.

A fully protected peptide is made by standard solid phase peptide synthesis (SPPS) using Fmoc/t-butyl technology (Int J Peptide Protein Res 35, 161 (1990)). Use of a normal resin leads to the C-terminal acid 10a after the final deblocking, whereas use of an aminated resin leads to the C-terminal amide 10b after the final deblocking (J Peptide Sci 16, 551 (2010)). The N-terminal Fmoc protecting group is removed as normal, and the free amine is now acylated with the acid 8b, using HBTU (or HATU) DIPEA in DMF at RT. The entire molecule is then globally deprotected with TFA (Methods Mol Biol 35, 63 (1994)), to give 10a/b after RP-HPLC purification.

The following compounds of structures 10a or 10b, which all incorporate combined CPP/NLS domains, and contain a single retro-inverso peptide chain are made via the process described above Compound 10a-1:
peptide-CO₂H is d-(GRKKRRQRRRGGPLSGFSL(SEQ ID NO: 35))

Compound 10a-2:
peptide-CO₂H is d-(GRWRRRRNRRAQRGGPLSGFSL(SEQ ID NO: 36))

Compound 10a-3:
peptide-CO₂H is d-(GVKRKKKPGGPLSGFSL(SEQ ID NO: 37))

Compound 10a-4:
peptide-CO₂H is d-(GRKKRRQRRRGGPFTGFTF(SEQ ID NO: 38))

Compound 10a-5:
peptide-CO₂H is d-(GRWRRRRNRRAQRGGPFTGFTF(SEQ ID NO: 39))

Compound 10a-6:
peptide-CO₂H is d-(GVKRKKKPGGPFTGFTF(SEQ ID NO: 40))

Compound 10a-7:
peptide-CO₂H is d-(GRKKRRQRRRGGTFLYPPL(SEQ ID NO: 41))

Compound 10a-8:
peptide-CO₂H is d-(GRWRRRRNRRAQRGGTFLYPPL(SEQ ID NO: 42))

Compound 10a-9:
peptide-CO₂H is d-(GVKRKKKPGGTFLYPPL(SEQ ID NO: 43))

Compound 10a-10:
peptide-CO₂H is d-(GRKKRRQRRRGGLYPP(SEQ ID NO: 44))

Compound 10a-11:
peptide-CO₂H is d-(GRWRRRRNRRAQRGGLYPP(SEQ ID NO: 45))

Compound 10a-12:
peptide-CO₂H is d-(GVKRKKKPGGLYPP(SEQ ID NO: 46))

Compound 10b-1:
peptide-CONH₂ is d-(GRKKRRQRRRGGPLSGFSL(SEQ ID NO: 35))

Compound 10b-2:
peptide-CONH₂ is d-(GRWRRRRNRRAQRGGPLSGFSL(SEQ ID NO: 36))

Compound 10b-3:
peptide-CONH₂ is d-(GVKRKKKPGGPLSGFSL(SEQ ID NO: 37))

Compound 10b-4:
peptide-CONH₂ is d-(GRKKRRQRRRGG PFTGFTF(SEQ ID NO: 38))

Compound 10b-5:
peptide-CONH₂ is d-(GRWRRRRNRRAQRGGPFTGFTF(SEQ ID NO: 39))

Compound 10b-6:
peptide-CONH₂ is d-(GVKRKKKPGGPFTGFTF(SEQ ID NO: 40))

Compound 10b-7:
peptide-CONH₂ is d-(GRKKRRQRRRGGTFLYPPL(SEQ ID NO: 41))

Compound 10b-8:
peptide-CONH₂ is d-(GRWRRRRNRRAQRGGTFLYPPL(SEQ ID NO: 42))

Compound 10b-9:
peptide-CONH₂ is d-(GVKRKKKPGGTFLYPPL(SEQ ID NO: 43))

Compound 10b-10:
peptide-CONH₂ is d-(GRKKRRQRRRGGLYPP(SEQ ID NO: 44))

Compound 10b-11:
peptide-CONH₂ is d-(GRWRRRRNRRAQRGGLYPP(SEQ ID NO: 45))

Compound 10b-12:
peptide-CONH₂ is d-(GVKRKKKPGGLYPP(SEQ ID NO: 46))

Scheme 3. General Synthesis for C-Terminal PSMA-targeted EIP conugated peptides 12. Di-O-tert-butyl (S,S)-2-(3-(6-[N-(4-bromobenzyl)N-(36-amino-1-oxo-3,6,9,12,15,18,21,24,27,30,33-undecyloxahexatriacontanyl)amino]-1-(tert-butoxy)-1-oxohexan-2-yl)ureido)pentanedioate

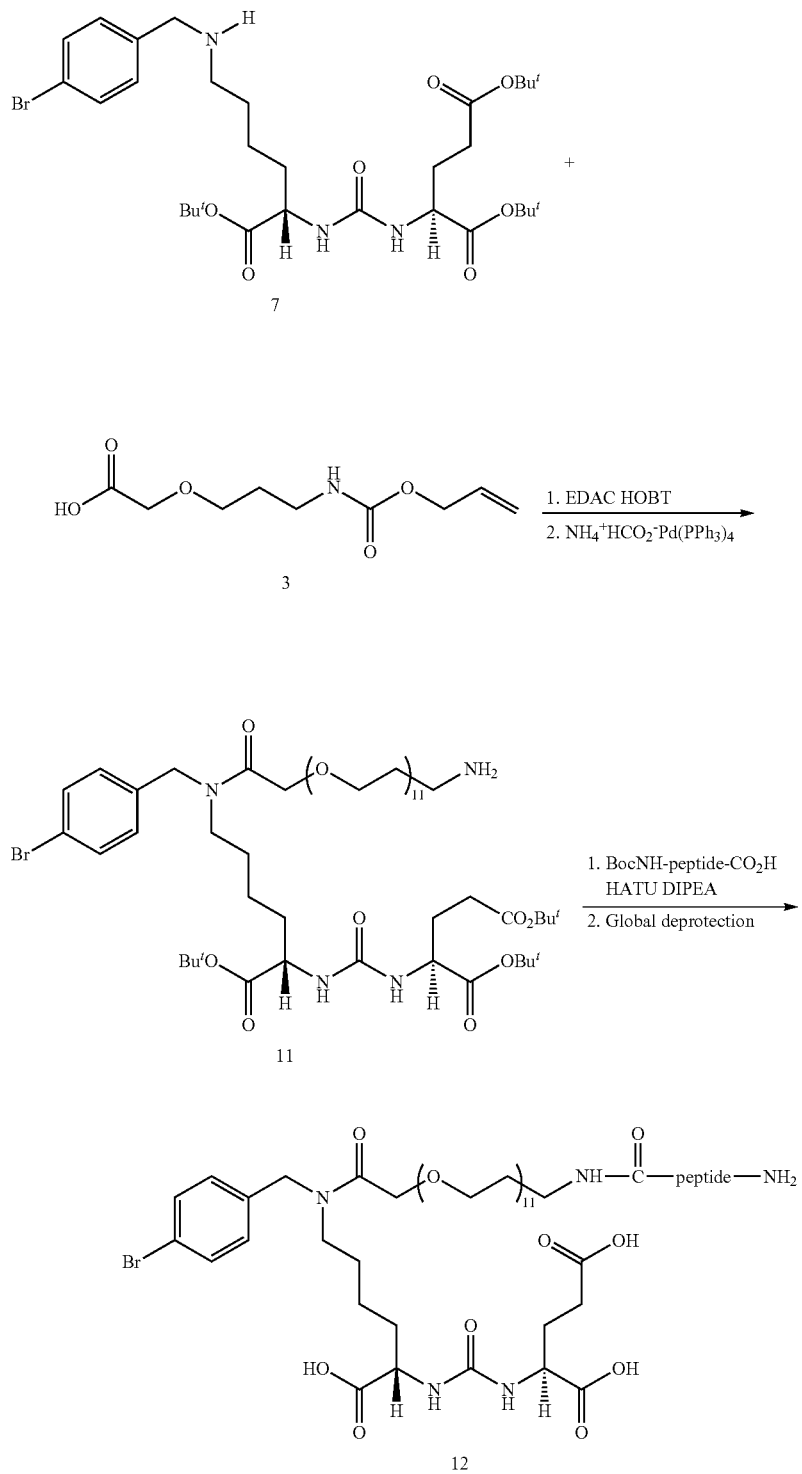

Secondary amine 7 and long chain acid 3 are reacted together with HOBT and EDAC to form the corresponding tertiary amide. This is then selectively deblocked on the 36-amino position by using ammonium formate and catalytic Pd to give the title amine 11. Use of the corresponding 18-atom chain Alloc-acid leads to a shorter linker section, with 5 rather than 11 ethylene oxide repeats, which can be used identically in linker chemistry.

C-Terminally PSMA Ligand-Tethered CPP-NLS-EIP Peptides. 12

The fully protected peptide is made on a SASRIN (or other very mild acid cleavable resin) solid phase resin by Fmoc/t-Bu techniques, and is cleaved off the resin in otherwise fully protected form by hexafluoroisopropanol/DCM or 1% TFA in DCM. The free C-terminal acid is then condensed with di-O-tert-butyl (S, S)-2-(3-(6-[N-(4-bromobenzyl)N-(36-amino-1-oxo-3,6,9,12,15,18,21,24,27,30, 33-undecyloxahexatriacontanyl)amino]-1-(tert-butoxy)-1-oxohexan-2-yl)ureido)pentanedioate 11 using TBTU and DIPEA in DMF (Bioorg Med Chem 22, 4099 (2014)). The full deblock of the peptide is carried out with TFA, and the final peptide 12 is purified by RP-HPLC.

The following compounds of structures 12, which all incorporate combined CPP/NLS domains, and contain a single retro-inverso peptide chain are made via the process described above

```
Compound 12-1:
H2N-peptide-CO(NH) is d-(H2N-RKKRRQRRRGGPLSGFSL (SEQ ID NO: 47))

Compound 12-2:
H2N-peptide-CO(NH) is d-(H2N-RWRRRRNRRAQRGGPLSGFSL (SEQ ID NO: 48))

Compound 12-3:
H2N-peptide-CO(NH) is d-(H2N-VKRKKKPGGPLSGFSL(SEQ

ID NO: 49))

Compound 12-4:
H2N-peptide-CO(NH) is d-(RKKRRQRRRGGPFTGFTF(SEQ ID

NO: 50))

Compound 12-5:
H2N-peptide-CO(NH) is d-(H2N-RWRRRRNRRAQRGGPFTGFTF (SEQ ID NO: 51))

Compound 12-6:
H2N-peptide-CO(NH) is d-(H2N-VKRKKKPGGPFTGFTF(SEQ

ID NO: 52))

Compound 12-7:
H2N-peptide-CO(NH) is d-(H2N-RKKRRQRRRGGTFLYPPL (SEQ ID NO: 53))

Compound 12-8:
H2N-peptide-CO(NH) is d-(H2N-RWRRRRNRRAQRGGTFLYPPL (SEQ ID NO: 54))

Compound 12-9:
H2N-peptide-CO(NH) is d-(H2N-VKRKKKPGGTFLYPPL(SEQ

ID NO: 55))

Compound 12-10:
H2N-peptide-CO(NH) is d-(H2N-RKKRRQRRRGGLYPP(SEQ

ID NO: 56))

Compound 12-11:
H2N-peptide-CO(NH) is d-(H2N-RWRRRRNRRAQRGGLYPP

SEQ ID NO: 57))

Compound 12-12:
H2N-peptide-CO(NH) is d-(H2N-VKRKKKPGGLYPP(SEQ ID

NO: 58))
```

Synthesis of GRPR Targeted Compounds.

The usual targeting sequence for GRPR is the C-terminal residues of bombesin, thus, in some embodiments, it is placed at the C-terminus. The bombesin-based sequence fQWAVaHLM-OMe has been shown to be a good affinity GRPR antagonist (Peptides 13, 775 (1992)), and this can be used as a targeting moiety. In some embodiments, use of a spacer residue allows introduction of a malonate to act as a linker to a retro-inverso CPP-NLS EIP segment, as described below.

N-Terminally GRPR-Targeted Peptides

The fully protected bombesin sequence GfQWAVaHLM-NH2 (f=d-F, a=d-A) is prepared using standard Fmoc/t-Bu technology on an amine resin linker, and after removal of the last Fmoc residue is condensed with malonic acid monoallyl ester. The amide is cleaved from the resin and the malonic acid is deblocked using ammonium formate and catalytic Pd. It is then coupled to the unprotected N-terminal amine of an otherwise fully protected retro-inverso peptide comprising the CPP-NLS-EIP domain of the molecule, built by Fmoc/t-Bu technology, and still attached to the resin, using an appropriate coupling agent such as HATU/DIPEA. The completed peptide can then be cleaved from the resin under conditions which induce complete deblocking to give the compound after RP-HPLC purification.

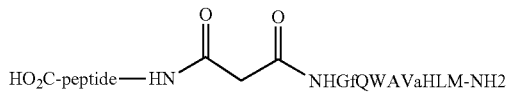

13a

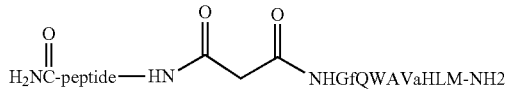

13b

The following compounds of structures 13a or 13b, which all incorporate combined CPP/NLS domains, and contain a single retro-inverso peptide chain are made via the process described above

```
Compound 13a-1:
peptide-CO2H is d-(GRKKRRQRRRGGPLSGFSL(SEQ ID NO:

35))

Compound 13a-2:
peptide-CO2H is d-(GRWRRRRNRRAQRGGPLSGFSL(SEQ ID

NO: 36))

Compound 13a-3:
peptide-CO2H is d-(GVKRKKKPGGPLSGFSL(SEQ ID NO:

37))
```

-continued

Compound 13a-4:
peptide-CO$_2$H is d-(GRKKRRQRRRGGPFTGFTF(SEQ ID NO: 38))

Compound 13a-5:
peptide-CO$_2$H is d-(GRWRRRRNRRAQRGGPFTGFTF(SEQ ID NO: 39))

Compound 13a-6:
peptide-CO$_2$H is d-(GVKRKKKPGGPFTGFTF(SEQ ID NO: 40))

Compound 13a-7:
peptide-CO$_2$H is d-(GRKKRRQRRRGGTFLYPPL(SEQ ID NO: 41))

Compound 13a-8:
peptide-CO$_2$H is d-(GRWRRRRNRRAQRGGTFLYPPL(SEQ ID NO: 42))

Compound 13a-9:
peptide-CO$_2$H is d-(GVKRKKKPGGTFLYPPL(SEQ ID NO: 43))

Compound 13a-10:
peptide-CO$_2$H is d-(GRKKRRQRRRGGLYPP(SEQ ID NO: 44))

Compound 13a-11:
peptide-CO$_2$H is d-(GRWRRRRNRRAQRGGLYPP(SEQ ID NO: 45))

Compound 13a-12:
peptide-CO$_2$H is d-(GVKRKKKPGGLYPP(SEQ ID NO: 46))

Compound 13b-1:
peptide-CONH$_2$ is d-(GRKKRRQRRRGGPLSGFSL(SEQ ID NO: 35))

Compound 13b-2:
peptide-CONH$_2$ is d-(GRWRRRRNRRAQRGGPLSGFSL(SEQ ID NO: 36))

Compound 13b-3:
peptide-CONH$_2$ is d-(GVKRKKKPGGPLSGFSL(SEQ ID NO: 37))

Compound 13b-4:
peptide-CONH$_2$ is d-(GRKKRRQRRRGGPFTGFTF(SEQ ID NO: 38))

Compound 13b-5:
peptide-CONH$_2$ is d-(GRWRRRRNRRAQRGGPFTGFTF(SEQ ID NO: 39))

Compound 13b-6:
peptide-CONH$_2$ is d-(GVKRKKKPGGPFTGFTF(SEQ ID NO: 40))

Compound 13b-7:
peptide-CONH$_2$ is d-(GRKKRRQRRRGGTFLYPPL(SEQ ID NO: 41))

Compound 13b-8:
peptide-CONH$_2$ is d-(GRWRRRRNRRAQRGGTFLYPPL(SEQ ID NO: 42))

Compound 13b-9:
peptide- CONH$_2$ is d-(GVKRKKKPGGTFLYPPL(SEQ ID NO: 43))

Compound 13b-10:
peptide-CONH$_2$ is d-(GRKKRRQRRRGGLYPP(SEQ ID NO: 44))

Compound 13b-11:
peptide-CONH$_2$ is d-(GRWRRRRNRRAQRGGLYPP(SEQ ID NO: 45))

Compound 13b-12:
peptide-CONH$_2$ is d-(GYKRKKKPGGLYPP(SEQ ID NO: 46))

Synthesis of LHRHR Targeted Compounds.

Use of intact LHRH as a targeting moiety is generally on the N-terminus of native peptides if the agent used is a single peptide chain, because the N-terminal residue is pyroglutamic acid, where it is a chain-terminating residue, by using the amine for cyclization. LHRH, the ligand of LHRHR, is a decapeptide pyro-EHWSYGLRPG-NH$_2$ and its close analogue Leuprolide is pyro-EHWSY1LRP-NHEt, a LHRH agonist in wide clinical use for prostate cancer with an ED$_{50}$ of about 0.2 nM, and a half life of 3 hours in humans, with its major loss being due to kidney excretion. $^6$Gly of LHRH has been modified to d-Leu in Leuprolide, and it can be further modified to d-Lys. This very potent modified Leuprolide has the advantage that the e-amine can be easily acylated with very high selectivity, and has been shown to be very effective at targeting a cytotoxin to tumors in vivo (Proc Natl Acad Sci USA 102, 12962).

36-Oxo-3,6,9,12,15,18,21,24,27,30,33,37-dodecyloxatetracont-39-enanoic acid 14

Acid 1 is converted to the corresponding allyl ester by treatment of its sodium salt with allyl bromide. The trimethylsilyl group is then removed with fluoride ion, and the primary alcohol oxidized up to an acid 14 with a reagent such as excess PDC.

N-Terminally LHRHR-Targeted Peptides

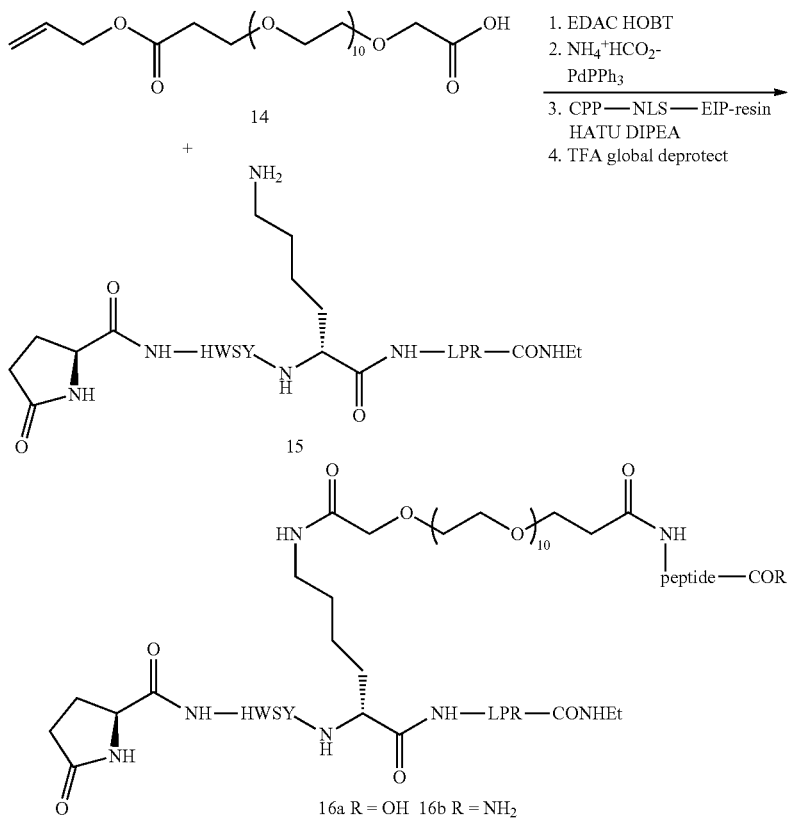

Scheme 4. General Synthesis for N-Terminal Leuprolide-targeted EIP conjugated peptides 16.

dK6dL Leuprolide, 15, is prepared by standard peptide chemistry, and the 6-lysyl amine is acylated with 36-oxo-3,6,9,12,15,18,21,24,27,30,33,37-dodecyloxatetracont-39-enanoic acid, 14, using a coupling agent such as EDAC/HOBT The allyl ester is then removed with Pd-catalyzed formate, and the freed acid residue is then used to acylate the unprotected N-terminus of a retro-inverso peptide, produced by Fmoc/t-Bu technology as described earlier, which is still otherwise fully protected, and still attached to the resin, using an appropriate coupling agent such as HATU/DIPEA. The completed peptide can then be cleaved from the resin under conditions which induce complete deblocking to give the compounds 16a/b after RP-HPLC purification.

The following compounds of structures 16a or 16b, which all incorporate combined CPP/NLS domains, and contain a single retro-inverso peptide chain are made via the process described above:

Compound 16a-1:
peptide-CO$_2$H is d-(GRKKRRQRRRGGPLSGFSL(SEQ ID NO: 35))

Compound 16a-2:
peptide-CO$_2$H is d-(GRWRRRRNRRAQRGGPLSGFSL(SEQ ID NO: ))

Compound 16a-3:
peptide-CO$_2$H is d-(GVKRKKKPGGPLSGFSL(SEQ ID NO: 37))

Compound 16a-4:
peptide-CO$_2$H is d-(GRKKRRQRRRGGPFTGFTF(SEQ ID NO: 38))

Compound 16a-5:
peptide-CO$_2$H is d-(GRWRRRRNRRAQRGGPFTGFTF(SEQ ID NO: 39))

Compound 16a-6:
peptide-CO$_2$H is d-(GVKRKKKPGGPFTGFTF(SEQ ID NO: 40))

Compound 16a-7:
peptide-CO$_2$H is d-(GRKKRRQRRRGGTFLYPPL(SEQ ID NO: 41))

Compound 16a-8:
peptide-CO$_2$H is d-(GRWRRRRNRRAQRGGTFLYPPL(SEQ ID NO: 42))

Compound 16a-9:
peptide-CO$_2$H is d-(GVKRKKKPGGTFLYPPL(SEQ ID NO: 43))

-continued

Compound 16a-10:
peptide-CO$_2$H is d-(GRKKRRQRRRGGLYPP(SEQ ID NO: 44))

Compound 16a-11:
peptide-CO$_2$H is d-(GRWRRRRNRRAQRGGLYPP(SEQ ID NO: 45))

Compound 16a-12:
peptide-CO$_2$H is d-(GVKRKKKPGGLYPP(SEQ ID NO: 46))

Compound 16b-1:
peptide-CONH$_2$ is d-(GRKKRRQRRRGGPLSGFSL(SEQ ID NO: 35))

Compound 16b-2:
peptide-CONH$_2$ is d-(GRWRRRRNRRAQRGGPLSGFSL(SEQ ID NO: 36))

Compound 16b-3:
peptide-CONH$_2$ is d-(GVKRKKKPGGPLSGFSL(SEQ ID NO: 37))

Compound 16b-4:
peptide-CONH$_2$ is d-(GRKKRRQRRRGGPFTGFTF(SEQ ID NO: 38))

Compound 16b-5:
peptide-CONH$_2$ is d-(GRWRRRRNRRAQRGGPFTGFTF(SEQ ID NO: 39))

-continued

Compound 16b-6:
peptide-CONH$_2$ is d-(GVKRKKKPGGPFTGFTF(SEQ ID NO: 40))

Compound 16b-7:
peptide-CONH$_2$ is d-(GRKKRRQRRRGGTFLYPPL(SEQ ID NO: 41))

Compound 16b-8:
peptide-CONH$_2$ is d-(GRWRRRRNRRAQRGGTFLYPPL(SEQ ID NO: 42))

Compound 16b-9:
peptide- CONH$_2$ is d-(GVKRKKKPGGTFLYPPL(SEQ ID NO: 43))

Compound 16b-10:
peptide-CONH$_2$ is d-(GRKKRRQRRRGGLYPP(SEQ ID NO: 44))

Compound 16b-11:
peptide-CONH$_2$ is d-(GRWRRRRNRRAQRGGLYPP(SEQ ID NO: 45))

Compound 16b-12:
peptide-CONH$_2$ is d-(GVKRKKKPGGLYPP(SEQ ID NO: 46))

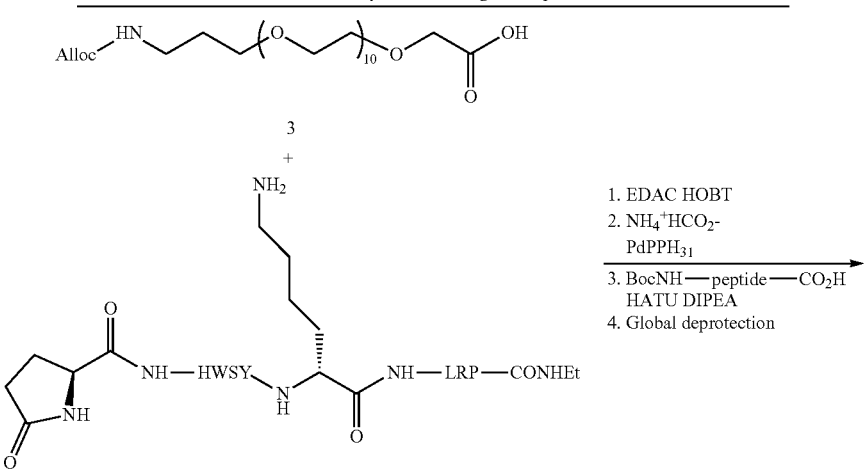

Scheme 5. General Synthesis for C-Terminal Leuprolide-targeted EIP conjugated peptides 17.
C-Terminally LHRHR-Targeted Peptides

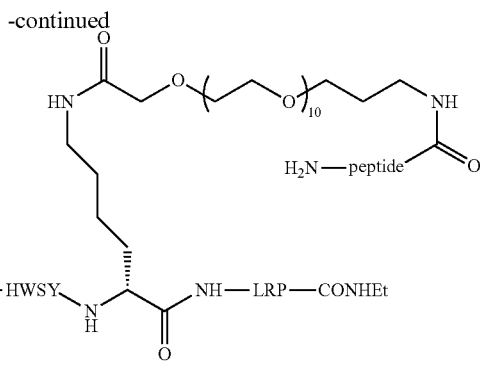

17

Leuprolide analogue 15 and long chain acid 3 are reacted together with HOBT and EDAC to form the corresponding secondary amide amide. This is then selectively deblocked on the 36-amino position by using ammonium formate and catalytic Pd toliberate the free primary amine. The desired fully protected peptide is made on a SASRIN (or other very mild acid cleavable resin) solid phase resin by Fmoc/t-Bu techniques, and is cleaved off the resin in otherwise fully protected form by hexafluoroisopropanol/DCM or 1% TFA in DCM. The free C-terminal acid is then condensed with the free amine on the Leuprolide linker terminus using TBTU and DIPEA in DMF. The full deblock of the peptide is carried out with TFA, and the final peptide 17 is purified by RP-HPLC.

The following compounds of structures 17, which all incorporate combined CPP/NLS domains, and contain a single retro-inverso peptide chain are made via the process described above:

```
Compound 17-1:
H2N-peptide-CO(NH) is d-(H2N-RKKRRQRRRGGPLSGFSL (SEQ ID NO: 47))

Compound 17-2:
H2N-peptide-CO(NH) is d-(H2N-RWRRRRNRRAQRGGPLSGFSL (SEQ ID NO: 48))

Compound 17-3:
H2N-peptide-CO(NH) is d-(H2N-VKRKKKPGGPLSGFSL(SEQ

ID NO: 49))

Compound 17-4:
H2N-peptide-CO(NH) is d-(RKKRRQRRRGGPFTGFTF(SEQ ID

NO: 50))

Compound 17-5:
H2N-peptide-CO(NH) is d-(H2N-RWRRRRNRRAQRGGPFTGFTF (SEQ ID NO: 51))

Compound 17-6:
H2N-peptide-CO(NH) is d-(H2N-VKRKKKPGGPFTGFTF(SEQ

ID NO: 52))

Compound 17-7:
H2N-peptide-CO(NH) is d-(H2N-RKKRRQRRRGGTFLYPPL

SEQ ID NO: 53))

Compound 17-8:
H2N-peptide-CO(NH) is d-(H2N-RWRRRRNRRAQRGGTFLYPPL (SEQ ID NO: 54))

Compound 17-9:
H2N-peptide-CO(NH) is d-(H2N-VKRKKKPGGTFLYPPL(SEQ

ID NO: 55))

Compound 17-10:
H2N-peptide-CO(NH) is d-(H2N-RKKRRQRRRGGLYPP(SEQ

ID NO: 56))

Compound 17-11:
H2N-peptide-CO(NH) is d-(H2N-RWRRRRNRRAQRGGLYPP (SEQ ID NO: 57))

Compound 17-12:
H2N-peptide-CO(NH) is d-(H2N-VKRKKKPGGLYPP(SEQ ID

NO: 58))
```

Block-Copolymer Acid-Sensitive Linked Micellar Peptides

Block copolymers of polyethylene glycol and polyaspartate contain internal polycarboxylic acid domains, which can be modified to acyl hydrazines, allowing coupling of drugs as acylhydrazones. These form micelles, and are chemically stable at pH 7.4, and because of their relatively large size, are not readily excreted through the kidney, leading to long plasma half lives. After internalization into cells, a process which is tumor selective due to the EPR effect, the acyl hydrazones are cleaved in the acidic endosomal compartment to release the peptide drugs.

Scheme 6. Condensation of EIP-containing peptide to block co=polymer with an acid-labile acylhydrazone linker

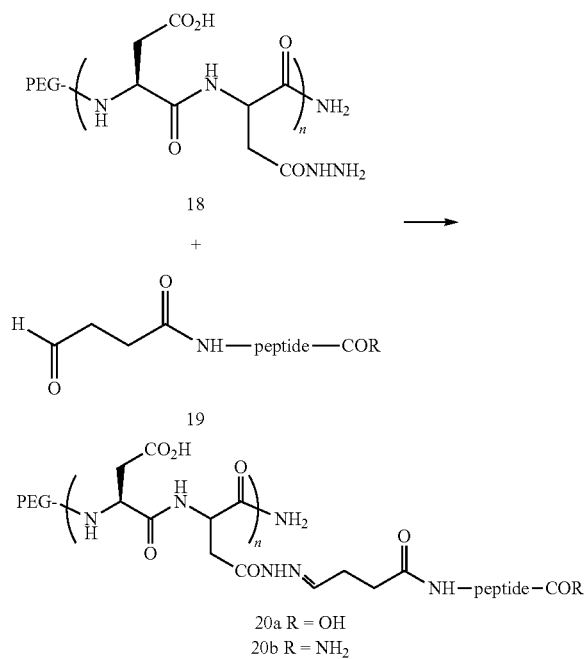

A PEG-polyaspartate block copolymer is prepared as described in J Control Release 188, 67 (2014), and using their protocol is partially converted to the corresponding acyl hydrazole to give 18. Complete conversion of carboxylates into acyl hydrazines is not attempted, due both to the large size of the drug to be attached, and the need to partially neutralize the large positive charge of the CPP-NLS portions of the peptide.

The desired peptide is prepared by the normal SPPS Fmoc/t-Bu technology, and after the N-terminal Fmoc group has been removed, the peptide is treated with 4,4-diethoxybutanoic acid and a coupling agent such as HATU/DIPEA. The peptide is then globally deprotected, including being cleaved from the resin, and is purified under acid conditions as a poly-TFA salt of 19 by RP-HPLC. The peptide is then mixed in aqueous conditions with the copolymer, and the pH is raised to pH 7 or above, to form the hydrazone 20a/b, which is purified by dialysis, and lyophilized, and can be reconstituted as micelles by sonication in PBS.

The following compounds of structures 20a or 20b, which all incorporate combined CPP/NLS domains, and contain a single retro-inverso peptide chain are made via the process described above:

Compound 20a-1:
peptide-CO$_2$H is d-(GRKKRRQRRRGGPLSGFSL(SEQ ID NO: 35))

Compound 20a-2:
peptide-CO$_2$H is d-(GRWRRRRNRRAQRGGPLSGFSL(SEQ ID NO: 36))

Compound 20a-3:
peptide-CO$_2$H is d-(GVKRKKKPGGPLSGFSL(SEQ ID NO: 37))

Compound 20a-4:
peptide-CO$_2$H is d-(GRKKRRQRRRGGPFTGFTF(SEQ ID NO: 38))

Compound 20a-5:
peptide-CO$_2$H is d-(GRWRRRRNRRAQRGGPFTGFTF(SEQ ID NO: 39))

Compound 20a-6:
peptide-CO$_2$H is d-(GVKRKKKPGGPFTGFTF(SEQ ID NO: 40))

Compound 20a-7:
peptide-CO$_2$H is d-(GRKKRRQRRRGGTFLYPPL(SEQ ID NO: 41))

Compound 20a-8:
peptide-CO$_2$H is d-(GRWRRRRNRRAQRGGTFLYPPL(SEQ ID NO: 42))

Compound 20a-9:
peptide-CO$_2$H is d-(GVKRKKKPGGTFLYPPL(SEQ ID NO: 43))

Compound 20a-10:
peptide-CO$_2$H is d-(GRKKRRQRRRGGLYPP(SEQ ID NO: 44))

Compound 20a-11:
peptide-CO$_2$H is d-(GRWRRRRNRRAQRGGLYPP(SEQ ID NO: 45))

Compound 20a-12:
peptide-CO$_2$H is d-(GVKRKKKPGGLYPP(SEQ ID NO: 46))

Compound 20b-1:
peptide-CONH$_2$ is d-(GRKKRRQRRRGGPLSGFSL(SEQ ID NO: 35))

Compound 20b-2:
peptide-CONH$_2$ is d-(GRWRRRRNRRAQRGGPLSGFSL(SEQ ID NO: 36))

Compound 20b-3:
peptide-CONH$_2$ is d-(GVKRKKKPGGPLSGFSL(SEQ ID NO: 37))

Compound 20b-4:
peptide-CONH$_2$ is d-(GRKKRRQRRRGGPFTGFTF(SEQ ID NO: 38))

Compound 20b-5:
peptide-CONH$_2$ is d-(GRWRRRRNRRAQRGGPFTGFTF(SEQ ID NO: 39))

Compound 20b-6:
peptide-CONH$_2$ is d-(GVKRKKKPGGPFTGFTF(SEQ ID NO: 40))

-continued

Compound 20b-7:
peptide-CONH$_2$ is d-(GRKKRRQRRRGGTFLYPPL(SEQ ID NO: 41))

Compound 20b-8:
peptide-CONH$_2$ is d-(GRWRRRRNRRAQRGGTFLYPPL(SEQ ID NO: 42))

Compound 20b-9:
peptide- CONH$_2$ is d-(GVKRKKKPGGTFLYPPL(SEQ ID NO: 43))

Compound 20b-10:
peptide-CONH$_2$ is d-(GRKKRRQRRRGGLYPP(SEQ ID NO: 44))

Compound 20b-11:
peptide-CONH$_2$ is d-(GRWRRRRNRRAQRGGLYPP(SEQ ID NO: 45))

Compound 20b-12:
peptide-CONH$_2$ is d-(GVKRKKKPGGLYPP(SEQ ID NO: 46))

Targeted Dendrimer-Linked Extended EIP Peptides

Dendrimers are highly branching polymers, which can be built to form loose 3D structures with a whole series of identical chemical linking groups on the outer surface of them. They have been used for in vivo work in a number of different ways. They are usually based on amines and amides, and probably the best studied are the PAMAM dendrimers which have alternative repeating units of ethylene diamine and acrylic acid, starting with an ethylene diamine core. As two acrylic acids Michael add to each amine, and then each acid is amidated with ethylene diamine, this polymer has alternating tertiary amine and secondary amide functionalities, and has a twofold increase in number of active branching groups at every tertiary amine. The alternating functional units are divided into generations (G0, G1, G2 etc.) with the zero generation having four primary amines, the first eight, the second sixteen etc, if ethylene diamine is last monomer added. If acrylic acid is the last monomer added, the dendrimers are referred to as half generations, with the 0.5 generation having eight carboxylic acids, the 1.5 generation sixteen, etc. The third and fourth generation PAMAM dendrimers have molecular weights of about 6900 and 14200 respectively and 32 or 64 free amines, and are useful dendrimers for the current indication. These dendrimers can be obtained where anywhere up half of the amines have been converted to PEG groups, and these have advantages in terms of reduced kidney filtration and reduced immunogenicity, and for this indication we will consider G3 and G4 dendrimers, 50% acylated with end-methoxylated PEG-200.

In some embodiments, targeting the dendrimers is by the PSMA ligand 8b, described earlier, although one might equally well use modified leuprolide or bombesin analogues. The PEGylated dendrimers are treated with acid 3-5 equivalents of 8b and a coupling agent such as EDAC/DIPEA to give a dendrimer loading of 3-5 PSMA ligands on average per dendrimer.

The retro-inverso CPP-NLS-EIP peptide is built on the appropriate resin using Fmoc/t-Bu technology in the usual fashion, and the N-terminal amino acid is deprotected. The PSA-cleavable linker sequence GHSSKLQL is then added to the N-terminus using Fmoc (l)-amino acids, and the N-terminal Fmoc is again removed. This free amine is then condensed with acid 14, using a coupling agent such as HATU/DIPEA, and the completed peptide is selectively cleaved from the resin, followed by Pd catalyzed formate removal of the allyl group. The free carboxylic acid on the PEG chain is then used to acylate free amines on the dendrimer using a coupling reagent such as HATU/DIPEA. If the peptide has a free carboxylic acid, it may also couple directly to the dendrimer, but the space around the dendrimer, especially with the PEGylation already in place is going to be sterically rather crowded, and the less hindered (and PEG-like acid will be much more reactive under these conditions. It is possible that a portion of free sites are occupied by the completed peptide before the reaction becomes too sluggish to continue. At the completion of this coupling reaction, the reaction mixture is treated with acetic anhydride, to cap the remaining unreacted amines on the dendrimer, and then the whole assembly is globally deprotected by treatment with TFA. The dendrimers are rinsed exhaustively, and dialyzed, and can be lyophilized prior to use.

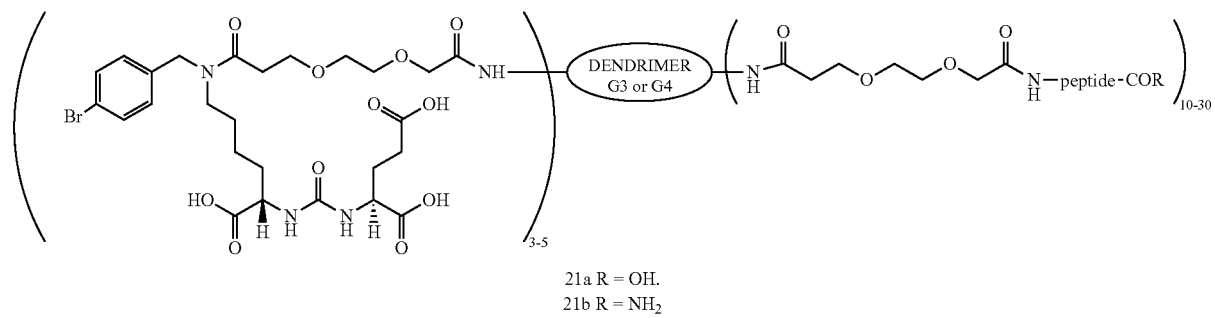

21a R = OH.
21b R = NH$_2$

The following compounds of structures 21a or 21b, which all incorporate combined CPP/NLS domains, and contain a single partial retro-inverso and partially native peptide chain are made via the process described above:

Compound 21a-1:
peptide-CO$_2$H is l-(GHSSKLQL)-d-(GRKKRRQRRRGGPLSGFSL(SEQ ID NO: 35))

Compound 21a-2:
peptide-CO$_2$H is l-(GHSSKLQL)-d-(GRWRRRRNRRAQRGGPLSGFSL(SEQ ID NO: 36))

Compound 21a-3:
peptide-CO₂H is l-(GHSSKLQL)-d-(GVKRKKKPGGPLSGFSL (SEQ ID NO: 37))

Compound 21a-4:
peptide-CO₂H is l-(GHSSKLQL)-d-(GRKKRRQRRRGGPFTGFTF(SEQ ID NO: 38))

Compound 21a-5:
peptide-CO₂H is l-(GHSSKLQL)-d-(GRWRRRRNRRAQRGGPFTGFTF(SEQ ID NO: 39))

Compound 21a-6:
peptide-CO₂H is l-(GHSSKLQL)-d-(GVKRKKKPGGPFTGFTF (SEQ ID NO: 40))

Compound 21a-7:
peptide-CO₂H is l-(GHSSKLQL)-d-(GRKKRRQRRRGGTFLYPPL(SEQ ID NO: 41))

Compound 21a-8:
peptide-CO₂H is l-(GHSSKLQL)-d-(GRWRRRRNRRAQRGGTFLYPPL(SEQ ID NO: 42))

Compound 21a-9:
peptide-CO₂H is l-(GHSSKLQL)-d-(GVKRKKKPGGTFLYPPL (SEQ ID NO: 43))

Compound 21a-10:
peptide-CO₂H is l-(GHSSKLQL)-d-(GRKKRRQRRRGGLYPP (SEQ ID NO: 44))

Compound 21a-11:
peptide-CO₂H is l-(GHSSKLQL)-d-(GRWRRRRNRRAQRGGLYPP(SEQ ID NO: 45))

Compound 21a-12:
peptide-CO₂H is l-(GHSSKLQL)-d-(GVKRKKKPGGLYPP(SEQ ID NO: 46))

Compound 21b-1:
peptide-CONH₂ is l-(GHSSKLQL)-d-(GRKKRRQRRRGGPLSGFSL(SEQ ID NO: 35))

Compound 21b-2:
peptide-CONH₂ is l-(GHSSKLQL)-d-(GRWRRRRNRRAQRGGPLSGFSL(SEQ ID NO: 36))

Compound 21b-3:
peptide-CONH₂ is l-(GHSSKLQL)-d-(GVKRKKKPGGPLSGFSL (SEQ ID NO: 37))

Compound 21b-4:
peptide-CONH₂ is l-(GHSSKLQL)-d-(GRKKRRQRRRGGPFTGFTF(SEQ ID NO: 38))

Compound 21b-5:
peptide-CONH₂ is l-(GHSSKLQL)-d-(GRWRRRRNRRAQRGGPFTGFTF(SEQ ID NO: 39))

Compound 21b-6:
peptide-CONH₂ is l-(GHSSKLQL)-d-(GVKRKKKPGGPFTGFTF (SEQ ID NO: 40))

Compound 21b-7:
peptide-CONH₂ is l-(GHSSKLQL)-d-(GRKKRRQRRRGGTFLYPPL(SEQ ID NO: 41))

Compound 21b-8:
peptide-CONH₂ is l-(GHSSKLQL)-d-(GRWRRRRNRRAQRGGTFLYPPL(SEQ ID NO: 42))

Compound 21b-9:
peptide-CONH₂ is l-(GHSSKLQL)-d-(GVKRKKKPGGTFLYPPL(SEQ ID NO: 43))

Compound 21b-10:
peptide-CONH₂ is l-(GHSSKLQL)-d-(GRKKRRQRRRGGLYPP (SEQ ID NO: 44))

Compound 21b-11:
peptide-CONH₂ is l-(GHSSKLQL)-d-(GRWRRRRNRRAQRGGLYPP(SEQ ID NO: 45))

Compound 21b-12:
peptide-CONH₂ is l-(GHSSKLQL)-d-(GVKRKKKPGGLYPP (SEQ ID NO: 46))

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

SEQUENCE LISTING

<160> NUMBER OF SEQ ID NOS: 122

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Arg Ala Leu Arg Tyr Tyr Tyr Asp Lys
1               5

```
<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Leu Ser Phe Gly Ser Leu Pro
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Leu Tyr Pro Pro
1

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Leu Pro Pro Tyr Leu Phe Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Pro Lys Lys Lys Arg Lys Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Pro Ala Ala Lys Arg Val Lys Leu Asp
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Arg Lys Lys Arg Arg Gln Arg Arg Arg
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gly Lys Lys Gln Tyr Lys Leu Lys His
1               5

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Lys Arg Ser Ala Glu Gly Ser Asn Pro Pro Lys Pro Leu Lys Lys Leu
1               5                   10                  15

Arg

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Pro Leu Ser Gly Phe Ser Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Pro Phe Thr Gly Phe Thr Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Thr Phe Leu Tyr Pro Pro Leu
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Arg Gln Ala Arg Arg Asn Arg Arg Arg Arg Trp Arg
1               5                   10
```

```
<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Val Lys Arg Lys Lys Lys Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Asp Leu Lys Val Arg Lys Ala Ala Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

His Lys Leu Lys Tyr Gln Lys Lys Gly
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Pro Pro Tyr Leu
1

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Leu Arg Lys Lys Leu Pro Lys Pro Pro Asn Ser Gly Glu Ala Ser Arg
1               5                   10                  15

Lys

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Arg Arg Arg Gln Arg Arg Lys Lys Arg
1               5
```

```
<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Arg Trp Arg Arg Arg Arg Asn Arg Arg Ala Gln Arg
1               5                   10

<210> SEQ ID NO 21
<211> LENGTH: 27
<212> TYPE: PRT
<213> ORGANISM: Artificial Sequence
<220> FEATURE:
<223> OTHER INFORMATION: Synthetic

<400> SEQUENCE: 21

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 22
<211> LENGTH: 21
<212> TYPE: PRT
<213> ORGANISM: Artificial Sequence
<220> FEATURE:
<223> OTHER INFORMATION: Synthetic

<400> SEQUENCE: 22

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 23
<211> LENGTH: 27
<212> TYPE: PRT
<213> ORGANISM: Artificial Sequence
<220> FEATURE:
<223> OTHER INFORMATION: Synthetic

<400> SEQUENCE: 23

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
```

```
<211> LENGTH: 18
<212> TYPE: PRT
<213> ORGANISM: Artificial Sequence
<220> FEATURE:
<223> OTHER INFORMATION: Synthetic

<400> SEQUENCE: 25

Lys Leu Ala Leu Lys Leu Ala Leu Lys Ala Leu Lys Ala Ala Leu Lys
1               5                   10                  15

Leu Ala

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

Gly Leu Trp Arg Ala Leu Trp Arg Leu Leu Arg Ser Leu Trp Arg Leu
1               5                   10                  15

Leu Trp Arg Ala
            20

<210> SEQ ID NO 27
<211> LENGTH: 16
<212> TYPE: PRT
<213> ORGANISM: Artificial Sequence
<220> FEATURE:
<223> OTHER INFORMATION: Synthetic

<400> SEQUENCE: 27

Arg Gln Ile Lys Ile Trp Phe Gln Asn Arg Arg Met Lys Trp Lys Lys
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Arg Arg Trp Trp Arg Arg Trp Arg Arg
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Asn Ala Lys Thr Arg Arg His Glu Arg Arg Arg Lys Leu Ala Ile Glu
1               5                   10                  15

Arg

<210> SEQ ID NO 30
<211> LENGTH: 16
<212> TYPE: PRT
<213> ORGANISM: Artificial Sequence
<220> FEATURE:
<223> OTHER INFORMATION: Synthetic

<400> SEQUENCE: 30
```

```
Arg Lys Lys Arg Arg Arg Glu Ser Arg Lys Lys Arg Arg Arg Glu Ser
1               5                   10                  15
```

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

```
Gly Arg Pro Arg Glu Ser Gly Lys Lys Arg Lys Arg Lys Arg Leu Lys
1               5                   10                  15

Pro
```

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

```
Ala Ala Val Leu Leu Pro Val Leu Leu Ala Ala Pro
1               5                   10
```

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

```
Cys Ser Ile Pro Pro Glu Val Lys Phe Asn Lys Pro Phe Val Tyr Leu
1               5                   10                  15

Ile
```

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

```
Leu His Arg His Arg
1               5
```

<210> SEQ ID NO 35
<211> LENGTH: 19
<212> TYPE: PRT
<213> ORGANISM: Artificial Sequence
<220> FEATURE:
<223> OTHER INFORMATION: Synthetic

<400> SEQUENCE: 35

```
Gly Arg Lys Lys Arg Arg Gln Arg Arg Arg Gly Gly Pro Leu Ser Gly
1               5                   10                  15

Phe Ser Leu
```

<210> SEQ ID NO 36
<211> LENGTH: 22
<212> TYPE: PRT

```
<213> ORGANISM: Artificial Sequence
<220> FEATURE:
<223> OTHER INFORMATION: Synthetic

<400> SEQUENCE: 36

Gly Arg Trp Arg Arg Arg Arg Asn Arg Arg Ala Gln Arg Gly Gly Pro
1               5                   10                  15

Leu Ser Gly Phe Ser Leu
            20

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Gly Val Lys Arg Lys Lys Lys Pro Gly Gly Pro Leu Ser Gly Phe Ser
1               5                   10                  15

Leu

<210> SEQ ID NO 38
<211> LENGTH: 19
<212> TYPE: PRT
<213> ORGANISM: Artificial Sequence
<220> FEATURE:
<223> OTHER INFORMATION: Synthetic

<400> SEQUENCE: 38

Gly Arg Lys Lys Arg Arg Gln Arg Arg Arg Gly Gly Pro Phe Thr Gly
1               5                   10                  15

Phe Thr Phe

<210> SEQ ID NO 39
<211> LENGTH: 22
<212> TYPE: PRT
<213> ORGANISM: Artificial Sequence
<220> FEATURE:
<223> OTHER INFORMATION: Synthetic

<400> SEQUENCE: 39

Gly Arg Trp Arg Arg Arg Arg Asn Arg Arg Ala Gln Arg Gly Gly Pro
1               5                   10                  15

Phe Thr Gly Phe Thr Phe
            20

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Gly Val Lys Arg Lys Lys Lys Pro Gly Gly Pro Phe Thr Gly Phe Thr
1               5                   10                  15

Phe

<210> SEQ ID NO 41
<211> LENGTH: 19
<212> TYPE: PRT
<213> ORGANISM: Artificial Sequence
<220> FEATURE:
```

<223> OTHER INFORMATION: Synthetic

<400> SEQUENCE: 41

Gly Arg Lys Lys Arg Arg Gln Arg Arg Gly Gly Thr Phe Leu Tyr
1               5                   10                  15

Pro Pro Leu

<210> SEQ ID NO 42
<211> LENGTH: 22
<212> TYPE: PRT
<213> ORGANISM: Artificial Sequence
<220> FEATURE:
<223> OTHER INFORMATION: Synthetic

<400> SEQUENCE: 42

Gly Arg Trp Arg Arg Arg Asn Arg Arg Ala Gln Arg Gly Gly Thr
1               5                   10                  15

Phe Leu Tyr Pro Pro Leu
            20

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Gly Val Lys Arg Lys Lys Lys Pro Gly Gly Thr Phe Leu Tyr Pro Pro
1               5                   10                  15

Leu

<210> SEQ ID NO 44
<211> LENGTH: 16
<212> TYPE: PRT
<213> ORGANISM: Artificial Sequence
<220> FEATURE:
<223> OTHER INFORMATION: Synthetic

<400> SEQUENCE: 44

Gly Arg Lys Lys Arg Arg Gln Arg Arg Gly Gly Leu Tyr Pro Pro
1               5                   10                  15

<210> SEQ ID NO 45
<211> LENGTH: 19
<212> TYPE: PRT
<213> ORGANISM: Artificial Sequence
<220> FEATURE:
<223> OTHER INFORMATION: Synthetic

<400> SEQUENCE: 45

Gly Arg Trp Arg Arg Arg Asn Arg Arg Ala Gln Arg Gly Gly Leu
1               5                   10                  15

Tyr Pro Pro

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Gly Val Lys Arg Lys Lys Lys Pro Gly Gly Leu Tyr Pro Pro

```
                1               5                    10
```

<210> SEQ ID NO 47
<211> LENGTH: 18
<212> TYPE: PRT
<213> ORGANISM: Artificial Sequence
<220> FEATURE:
<223> OTHER INFORMATION: Synthetic

<400> SEQUENCE: 47

```
Arg Lys Lys Arg Arg Gln Arg Arg Arg Gly Gly Pro Leu Ser Gly Phe
1               5                   10                  15

Ser Leu
```

<210> SEQ ID NO 48
<211> LENGTH: 21
<212> TYPE: PRT
<213> ORGANISM: Artificial Sequence
<220> FEATURE:
<223> OTHER INFORMATION: Synthetic

<400> SEQUENCE: 48

```
Arg Trp Arg Arg Arg Arg Asn Arg Arg Ala Gln Arg Gly Gly Pro Leu
1               5                   10                  15

Ser Gly Phe Ser Leu
            20
```

<210> SEQ ID NO 49
<211> LENGTH: 16
<212> TYPE: PRT
<213> ORGANISM: Artificial Sequence
<220> FEATURE:
<223> OTHER INFORMATION: Synthetic

<400> SEQUENCE: 49

```
Val Lys Arg Lys Lys Lys Pro Gly Gly Pro Leu Ser Gly Phe Ser Leu
1               5                   10                  15
```

<210> SEQ ID NO 50
<211> LENGTH: 18
<212> TYPE: PRT
<213> ORGANISM: Artificial Sequence
<220> FEATURE:
<223> OTHER INFORMATION: Synthetic

<400> SEQUENCE: 50

```
Arg Lys Lys Arg Arg Gln Arg Arg Arg Gly Gly Pro Phe Thr Gly Phe
1               5                   10                  15

Thr Phe
```

<210> SEQ ID NO 51
<211> LENGTH: 21
<212> TYPE: PRT
<213> ORGANISM: Artificial Sequence
<220> FEATURE:
<223> OTHER INFORMATION: Synthetic

<400> SEQUENCE: 51

```
Arg Trp Arg Arg Arg Arg Asn Arg Arg Ala Gln Arg Gly Gly Pro Phe
1               5                   10                  15

Thr Gly Phe Thr Phe
            20
```

<210> SEQ ID NO 52

```
<211> LENGTH: 16
<212> TYPE: PRT
<213> ORGANISM: Artificial Sequence
<220> FEATURE:
<223> OTHER INFORMATION: Synthetic

<400> SEQUENCE: 52

Val Lys Arg Lys Lys Lys Pro Gly Gly Pro Phe Thr Gly Phe Thr Phe
1               5                   10                  15

<210> SEQ ID NO 53
<211> LENGTH: 18
<212> TYPE: PRT
<213> ORGANISM: Artificial Sequence
<220> FEATURE:
<223> OTHER INFORMATION: Synthetic

<400> SEQUENCE: 53

Arg Lys Lys Arg Arg Gln Arg Arg Gly Gly Thr Phe Leu Tyr Pro
1               5                   10                  15

Pro Leu

<210> SEQ ID NO 54
<211> LENGTH: 21
<212> TYPE: PRT
<213> ORGANISM: Artificial Sequence
<220> FEATURE:
<223> OTHER INFORMATION: Synthetic

<400> SEQUENCE: 54

Arg Trp Arg Arg Arg Arg Asn Arg Arg Ala Gln Arg Gly Gly Thr Phe
1               5                   10                  15

Leu Tyr Pro Pro Leu
            20

<210> SEQ ID NO 55
<211> LENGTH: 16
<212> TYPE: PRT
<213> ORGANISM: Artificial Sequence
<220> FEATURE:
<223> OTHER INFORMATION: Synthetic

<400> SEQUENCE: 55

Val Lys Arg Lys Lys Lys Pro Gly Gly Thr Phe Leu Tyr Pro Pro Leu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Arg Lys Lys Arg Arg Gln Arg Arg Gly Gly Leu Tyr Pro Pro
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: Synthetic

<400> SEQUENCE: 57

Arg Trp Arg Arg Arg Arg Asn Arg Arg Ala Gln Arg Gly Gly Leu Tyr
```

```
1               5                   10                  15

Pro Pro

<210> SEQ ID NO 58
<211> LENGTH: 13
<212> TYPE: PRT
<213> ORGANISM: Artificial Sequence
<220> FEATURE:
<223> OTHER INFORMATION: Synthetic

<400> SEQUENCE: 58

Val Lys Arg Lys Lys Lys Pro Gly Gly Leu Tyr Pro Pro
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Synthetic

<400> SEQUENCE: 59

Gly His Ser Ser Lys Leu Gln Leu
1               5

<210> SEQ ID NO 60
<211> LENGTH: 19
<212> TYPE: PRT
<213> ORGANISM: Artificial Sequence
<220> FEATURE:
<223> OTHER INFORMATION: Synthetic

<400> SEQUENCE: 60

Gly Arg Arg Arg Gln Arg Arg Lys Lys Arg Gly Gly Thr Phe Leu Tyr
1               5                   10                  15

Pro Pro Leu

<210> SEQ ID NO 61
<211> LENGTH: 19
<212> TYPE: PRT
<213> ORGANISM: Artificial Sequence
<220> FEATURE:
<223> OTHER INFORMATION: Synthetic

<400> SEQUENCE: 61

Gly Arg Arg Arg Gln Arg Arg Lys Lys Arg Gly Gly Pro Leu Ser Gly
1               5                   10                  15

Phe Ser Leu

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

His Ser Ser Lys Leu Gln Leu
1               5

<210> SEQ ID NO 63
<211> LENGTH: 6
<212> TYPE: PRT
<213> ORGANISM: Artificial Sequence
<220> FEATURE:
```

<223> OTHER INFORMATION: Synthetic

<400> SEQUENCE: 63

Met Ala Gly Gln Arg Leu
1               5

<210> SEQ ID NO 64
<211> LENGTH: 20
<212> TYPE: PRT
<213> ORGANISM: Artificial Sequence
<220> FEATURE:
<223> OTHER INFORMATION: Synthetic

<400> SEQUENCE: 64

Lys Arg Ser Ala Glu Gly Ser Asn Pro Pro Lys Pro Leu Lys Lys Leu
1               5                   10                  15

Arg Asn Leu Ser
            20

<210> SEQ ID NO 65
<211> LENGTH: 17
<212> TYPE: PRT
<213> ORGANISM: Artificial Sequence
<220> FEATURE:
<223> OTHER INFORMATION: Synthetic

<400> SEQUENCE: 65

Arg Leu Lys Lys Leu Pro Lys Pro Pro Asn Ser Gly Glu Ala Ser Arg
1               5                   10                  15

Lys

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Gln Trp Ala Val Gly His Leu Met
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Glu His Trp Ser Tyr Gly Leu Arg Pro Gly
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Lys Tyr Leu Ala Tyr Pro Asp Ser Val His Ile Trp
1               5                   10

<210> SEQ ID NO 69

```
<211> LENGTH: 12
<212> TYPE: PRT
<213> ORGANISM: Artificial Sequence
<220> FEATURE:
<223> OTHER INFORMATION: Synthetic

<400> SEQUENCE: 69

Trp Gln Pro Asp Thr Ala His His Trp Ala Thr Leu
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Phe Ser Ala Ser Ser Pro Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic

<400> SEQUENCE: 71

Phe Ser Phe Gly Ser Leu Pro
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic

<400> SEQUENCE: 72

Leu Ala Phe Gly Ser Leu Pro
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic

<400> SEQUENCE: 73

Phe Thr Phe Gly Ser Leu Pro
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic

<400> SEQUENCE: 74

Leu Thr Phe Gly Ser Leu Pro
1               5

<210> SEQ ID NO 75
<211> LENGTH: 7
```

<212> TYPE: PRT
<213> ORGANISM: Artificial Sequence
<220> FEATURE:
<223> OTHER INFORMATION: Synthetic

<400> SEQUENCE: 75

Met Thr Phe Gly Thr Leu Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic

<400> SEQUENCE: 76

Tyr Thr Phe Gly Thr Leu Pro
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic

<400> SEQUENCE: 77

Leu Arg Phe Gly Thr Leu Pro
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

Leu Ser Phe Gly Ser Phe Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic

<400> SEQUENCE: 79

Leu Ser Phe Gly Thr Phe Pro
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic

<400> SEQUENCE: 80

His Ser Lys Ile Asn Pro Thr
1               5

<210> SEQ ID NO 81
<211> LENGTH: 7
<212> TYPE: PRT

```
<213> ORGANISM: Artificial Sequence
<220> FEATURE:
<223> OTHER INFORMATION: Synthetic

<400> SEQUENCE: 81

Val Pro Ser Gly Ser Pro Phe
1               5

<210> SEQ ID NO 82
<211> LENGTH: 19
<212> TYPE: PRT
<213> ORGANISM: Artificial Sequence
<220> FEATURE:
<223> OTHER INFORMATION: Synthetic

<400> SEQUENCE: 82

Leu Pro Pro Tyr Leu Phe Thr Gly Gly Arg Lys Lys Arg Arg Gln Arg
1               5                   10                  15

Arg Arg Gly

<210> SEQ ID NO 83
<211> LENGTH: 19
<212> TYPE: PRT
<213> ORGANISM: Artificial Sequence
<220> FEATURE:
<223> OTHER INFORMATION: Synthetic

<400> SEQUENCE: 83

Leu Ser Phe Gly Ser Leu Pro Gly Gly Arg Lys Lys Arg Arg Gln Arg
1               5                   10                  15

Arg Arg Gly

<210> SEQ ID NO 84
<211> LENGTH: 19
<212> TYPE: PRT
<213> ORGANISM: Artificial Sequence
<220> FEATURE:
<223> OTHER INFORMATION: Synthetic

<400> SEQUENCE: 84

Leu Pro Pro Ala Leu Phe Thr Gly Gly Arg Lys Lys Arg Arg Gln Arg
1               5                   10                  15

Arg Arg Gly

<210> SEQ ID NO 85
<211> LENGTH: 19
<212> TYPE: PRT
<213> ORGANISM: Artificial Sequence
<220> FEATURE:
<223> OTHER INFORMATION: Synthetic

<400> SEQUENCE: 85

Gly Arg Arg Arg Gln Arg Arg Lys Lys Arg Gly Gly Thr Phe Leu Tyr
1               5                   10                  15

Pro Pro Leu

<210> SEQ ID NO 86
<211> LENGTH: 19
<212> TYPE: PRT
<213> ORGANISM: Artificial Sequence
<220> FEATURE:
<223> OTHER INFORMATION: Synthetic

<400> SEQUENCE: 86
```

Gly Arg Arg Arg Gln Arg Lys Lys Arg Gly Gly Pro Leu Ser Gly
1               5                   10                  15

Phe Ser Leu

<210> SEQ ID NO 87
<211> LENGTH: 86
<212> TYPE: PRT
<213> ORGANISM: Artificial Sequence
<220> FEATURE:
<223> OTHER INFORMATION: Synthetic

<400> SEQUENCE: 87

Gly Gln Ile Gln Leu Trp Gln Phe Leu Glu Leu Ser Asp Ser
1               5                   10                  15

Ser Asn Ser Ser Cys Ile Thr Trp Glu Gly Thr Asn Gly Glu Phe Lys
                20                  25                  30

Met Thr Asp Pro Asp Glu Val Ala Arg Arg Trp Gly Glu Arg Lys Ser
            35                  40                  45

Trp Pro Asn Met Asn Tyr Asp Lys Leu Ser Arg Ala Leu Arg Tyr Tyr
        50                  55                  60

Asp Lys Asn Ile Met Thr Lys Val His Gly Lys Arg Tyr Ala Tyr Lys
65                  70                  75                  80

Phe Asp Phe His Gly Ile
                85

<210> SEQ ID NO 88
<211> LENGTH: 29
<212> TYPE: PRT
<213> ORGANISM: Artificial Sequence
<220> FEATURE:
<223> OTHER INFORMATION: Synthetic

<400> SEQUENCE: 88

Gly Gln Ile Gln Leu Trp Gln Phe Leu Glu Leu Ser Asp Ser
1               5                   10                  15

Ser Asn Ser Ser Cys Ile Thr Trp Glu Gly Thr Asn Gly
                20                  25

<210> SEQ ID NO 89
<211> LENGTH: 29
<212> TYPE: PRT
<213> ORGANISM: Artificial Sequence
<220> FEATURE:
<223> OTHER INFORMATION: Synthetic

<400> SEQUENCE: 89

Ser Ser Asn Ser Ser Cys Ile Thr Trp Glu Gly Thr Asn Gly Glu Phe
1               5                   10                  15

Lys Met Thr Asp Pro Asp Glu Val Ala Arg Arg Trp Gly
                20                  25

<210> SEQ ID NO 90
<211> LENGTH: 29
<212> TYPE: PRT
<213> ORGANISM: Artificial Sequence
<220> FEATURE:
<223> OTHER INFORMATION: Synthetic

<400> SEQUENCE: 90

Glu Phe Lys Met Thr Asp Pro Asp Glu Val Ala Arg Arg Trp Gly Glu
1               5                   10                  15

Arg Lys Ser Lys Pro Asn Met Asn Tyr Asp Lys Leu Ser

```
                    20                  25

<210> SEQ ID NO 91
<211> LENGTH: 29
<212> TYPE: PRT
<213> ORGANISM: Artificial Sequence
<220> FEATURE:
<223> OTHER INFORMATION: Synthetic

<400> SEQUENCE: 91

Arg Ala Leu Arg Tyr Tyr Tyr Asp Lys Asn Ile Met Thr Lys Val His
1               5                   10                  15

Gly Lys Arg Tyr Ala Tyr Lys Phe Asp Phe His Gly Ile
                20                  25

<210> SEQ ID NO 92
<211> LENGTH: 29
<212> TYPE: PRT
<213> ORGANISM: Artificial Sequence
<220> FEATURE:
<223> OTHER INFORMATION: Synthetic

<400> SEQUENCE: 92

Met Thr Asp Pro Asp Glu Val Ala Arg Arg Trp Gly Glu Arg Lys Ser
1               5                   10                  15

Lys Pro Asn Met Asn Tyr Asp Lys Leu Ser Arg Ala Leu
                20                  25

<210> SEQ ID NO 93
<211> LENGTH: 29
<212> TYPE: PRT
<213> ORGANISM: Artificial Sequence
<220> FEATURE:
<223> OTHER INFORMATION: Synthetic

<400> SEQUENCE: 93

Pro Asp Glu Val Ala Arg Arg Trp Gly Glu Arg Lys Ser Lys Pro Asn
1               5                   10                  15

Met Asn Tyr Asp Lys Leu Ser Arg Ala Leu Arg Tyr Tyr
                20                  25

<210> SEQ ID NO 94
<211> LENGTH: 29
<212> TYPE: PRT
<213> ORGANISM: Artificial Sequence
<220> FEATURE:
<223> OTHER INFORMATION: Synthetic

<400> SEQUENCE: 94

Val Ala Arg Arg Trp Gly Glu Arg Lys Ser Lys Pro Asn Met Asn Tyr
1               5                   10                  15

Asp Lys Leu Ser Arg Ala Leu Arg Tyr Tyr Tyr Asp Lys
                20                  25

<210> SEQ ID NO 95
<211> LENGTH: 29
<212> TYPE: PRT
<213> ORGANISM: Artificial Sequence
<220> FEATURE:
<223> OTHER INFORMATION: Synthetic

<400> SEQUENCE: 95

Arg Trp Gly Glu Arg Lys Ser Lys Pro Asn Met Asn Tyr Asp Lys Leu
1               5                   10                  15
```

Ser Arg Ala Leu Arg Tyr Tyr Tyr Asp Lys Asn Ile Met
            20                  25

<210> SEQ ID NO 96
<211> LENGTH: 29
<212> TYPE: PRT
<213> ORGANISM: Artificial Sequence
<220> FEATURE:
<223> OTHER INFORMATION: Synthetic

<400> SEQUENCE: 96

Lys Ser Lys Pro Asn Met Asn Tyr Asp Lys Leu Ser Arg Ala Leu Arg
1               5                   10                  15

Tyr Tyr Tyr Asp Lys Asn Ile Met Thr Lys Val His Gly
            20                  25

<210> SEQ ID NO 97
<211> LENGTH: 27
<212> TYPE: PRT
<213> ORGANISM: Artificial Sequence
<220> FEATURE:
<223> OTHER INFORMATION: Synthetic

<400> SEQUENCE: 97

Met Asn Tyr Asp Lys Leu Ser Arg Ala Leu Arg Tyr Tyr Tyr Asp Lys
1               5                   10                  15

Asn Ile Met Thr Lys Val His Gly Lys Arg Tyr
            20                  25

<210> SEQ ID NO 98
<211> LENGTH: 24
<212> TYPE: PRT
<213> ORGANISM: Artificial Sequence
<220> FEATURE:
<223> OTHER INFORMATION: Synthetic

<400> SEQUENCE: 98

Lys Ala Leu Arg Tyr Tyr Tyr Asp Lys Asn Ile Met Thr Lys Val His
1               5                   10                  15

Gly Lys Arg Tyr Ala Tyr Lys Phe
            20

<210> SEQ ID NO 99
<211> LENGTH: 24
<212> TYPE: PRT
<213> ORGANISM: Artificial Sequence
<220> FEATURE:
<223> OTHER INFORMATION: Synthetic

<400> SEQUENCE: 99

Lys Ala Leu Arg Val Tyr Tyr Val Lys Asn Ile Met Thr Lys Val His
1               5                   10                  15

Gly Lys Arg Tyr Ala Tyr Lys Phe
            20

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

Leu Arg Gln Gly Ala Met
1               5

<210> SEQ ID NO 101
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 101

Lys Arg Xaa Arg
1

<210> SEQ ID NO 102
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 102

Xaa Xaa Xaa Lys Arg Xaa Xaa
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 103

Xaa Xaa Xaa Lys Arg Xaa
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 104

Xaa Xaa Arg Lys Xaa Xaa Xaa

```
1               5

<210> SEQ ID NO 105
<211> LENGTH: 7
<212> TYPE: PRT
<213>

<223> OTHER INFORMATION: Xaa can be any naturally occurring amino acid

<400> SEQUENCE: 108

Xaa Arg Lys Xaa Xaa Xaa
1               5

<210> SEQ ID NO 109
<211> LENGTH: 23
<212> TYPE: DNA
<213> ORGANISM: Artificial Sequence
<220> FEATURE:
<223> OTHER INFORMATION: Synthetic

<400> SEQUENCE: 109
gatcttcgaa acggaagttc gag                                           23

<210> SEQ ID NO 110
<211> LENGTH: 21
<212> TYPE: PRT
<213> ORGANISM: Artificial Sequence
<220> FEATURE:
<223> OTHER INFORMATION: Synthetic

<400> SEQUENCE: 110

Asn Thr Gly Gly Ala Ala Phe Ile Phe Pro Asn Thr Ser Val Tyr Pro
1               5                   10                  15

Glu Ala Thr Gln Arg
            20

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Leu Pro Pro Ala Leu Phe Thr
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic

<400> SEQUENCE: 112

Leu Ser Ala Gly Ser Ala Pro
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Leu Pro Pro Thr Phe Leu Tyr
1               5

<210> SEQ ID NO 114
<211> LENGTH: 486
<212> TYPE: PRT
<213> ORGANISM: Artificial Sequence
<220> FEATURE:
<223> OTHER INFORMATION: Synthetic

<400> SEQUENCE: 114

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Asp Tyr
        35                  40                  45

Gly Gln Thr Ser Lys Met Ser Pro Arg Val Pro Gln Gln Asp Trp Leu
    50                  55                  60

Ser Gln Ala Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Asn Lys
                85                  90                  95

Gly Gly Lys Met Val Gly Ser Pro Asp Thr Val Gly Met Ser Tyr Gly
            100                 105                 110

Ser Tyr Met Glu Glu Lys His Val Pro Pro Asn Met Thr Thr Asn
        115                 120                 125

Glu Arg Arg Val Ile Val Pro Ala Asp Pro Thr Leu Trp Ser Thr Asp
130                 135                 140

His Val Arg Gln Trp Leu Glu Trp Ala Val Lys Glu Tyr Gly Leu Leu
145                 150                 155                 160

Asp Val Asp Val Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Ser His
            260                 265                 270

Leu Thr Pro Gln Ser Lys Ala Ala Gln Pro Ser Pro Ser Ala Val Pro
        275                 280                 285

Lys Thr Glu Asp Gln Arg Pro Gln Leu Asp Pro Tyr Gln Ile Leu Gly
    290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Asn Cys
                325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
        355                 360                 365

Tyr Asp Lys Leu Ser Arg Ala Leu Arg Tyr Tyr Asp Lys Asn Ile
    370                 375                 380

Met Thr Lys Val His Gly Lys Arg Tyr Ala Tyr Lys Phe Asp Phe His
385                 390                 395                 400

```
Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
            420                 425                 430

Gln Lys Met Asn Phe Val Ser Pro His Pro Pro Ala Leu Pro Val Thr
        435                 440                 445

Ser Ser Ser Phe Phe Ala Ser Pro Asn Pro Tyr Trp Asn Ser Pro Thr
450                 455                 460

Gly Gly Ile Tyr Pro Asn Thr Arg Leu Pro Ala Ser His Met Pro Ser
465                 470                 475                 480

His Leu Gly Thr Tyr Tyr
                485

<210> SEQ ID NO 115
<211> LENGTH: 479
<212> TYPE: PRT
<213> ORGANISM: Artificial Sequence
<220> FEATURE:
<223> OTHER INFORMATION: Synthetic

<400> SEQUENCE: 115

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
50                  55                  60

Thr Ile Lys Met Glu Cys Asn Pro Ser Gln Val Asn Gly Ser Arg Asn
65                  70                  75                  80

Ser Pro Asp Glu Cys Ser Val Ala Lys Gly Gly Lys Met Val Gly Ser
                85                  90                  95

Pro Asp Thr Val Gly Met Asn Tyr Gly Ser Tyr Met Glu Glu Lys His
            100                 105                 110

Met Pro Pro Pro Asn Met Thr Thr Asn Glu Arg Arg Val Ile Val Pro
        115                 120                 125

Ala Asp Pro Thr Leu Trp Ser Thr Asp His Val Arg Gln Trp Leu Glu
            130                 135                 140

Trp Ala Val Lys Glu Tyr Gly Leu Pro Asp Val Asn Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Ala Phe Ile Phe Pro Asn Thr Ser Val Tyr Pro Glu Ala
225                 230                 235                 240

Thr Gln Arg Ile Thr Thr Arg Pro Asp Leu Pro Tyr Glu Pro Pro Arg
                245                 250                 255

Arg Ser Ala Trp Thr Gly His Gly His Pro Thr Pro Gln Ser Lys Ala
            260                 265                 270
```

```
Ala Gln Pro Ser Pro Ser Thr Val Pro Lys Thr Glu Asp Gln Arg Pro
            275                 280                 285

Gln Leu Asp Pro Tyr Gln Ile Leu Gly Pro Thr Ser Ser Arg Leu Ala
        290                 295                 300

Asn Pro Gly Ser Gly Gln Ile Gln Leu Trp Gln Phe Leu Leu Glu Leu
305                 310                 315                 320

Leu Ser Asp Ser Ser Asn Ser Ser Cys Ile Thr Trp Glu Gly Thr Asn
                325                 330                 335

Gly Glu Phe Lys Met Thr Asp Pro Asp Glu Val Ala Arg Arg Trp Gly
            340                 345                 350

Glu Arg Lys Ser Lys Pro Asn Met Asn Tyr Asp Lys Leu Ser Arg Ala
        355                 360                 365

Leu Arg Tyr Tyr Tyr Asp Lys Asn Ile Met Thr Lys Val His Gly Lys
    370                 375                 380

Arg Tyr Ala Tyr Lys Phe Asp Phe His Gly Ile Ala Gln Ala Leu Gln
385                 390                 395                 400

Pro His Pro Pro Glu Ser Ser Leu Tyr Lys Tyr Pro Ser Asp Leu Pro
                405                 410                 415

Tyr Met Gly Ser Tyr His Ala His Pro Gln Lys Met Asn Phe Val Ala
            420                 425                 430

Pro His Pro Pro Ala Leu Pro Val Thr Ser Ser Ser Phe Phe Ala Ala
        435                 440                 445

Pro Asn Pro Tyr Trp Asn Ser Pro Thr Gly Gly Ile Tyr Pro Asn Thr
    450                 455                 460

Arg Leu Pro Thr Ser His Met Pro Ser His Leu Gly Thr Tyr Tyr
465                 470                 475

<210> SEQ ID NO 116
<211> LENGTH: 478
<212> TYPE: PRT
<213> ORGANISM: Artificial Sequence
<220> FEATURE:
<223> OTHER INFORMATION: Synthetic

<400> SEQUENCE: 116

Met Ala Ser Thr Ile Lys Glu Ala Leu Ser Val Val Ser Glu Asp Gln
1               5                   10                  15

Ser Leu Phe Glu Cys Ala Tyr Gly Ser Pro His Leu Ala Lys Thr Glu
            20                  25                  30

Met Thr Ala Ser Ser Ser Ser Glu Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Asn Gln Val Asn Gly Ser Arg Asn
65                  70                  75                  80

Ser Pro Asp Asp Cys Ser Val Ala Lys Gly Gly Lys Met Val Ser Ser
                85                  90                  95

Ser Asp Asn Val Gly Met Asn Tyr Gly Ser Tyr Met Glu Glu Lys His
            100                 105                 110

Ile Pro Pro Pro Asn Met Thr Thr Asn Glu Arg Arg Val Ile Val Pro
        115                 120                 125

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asp Ile Leu Leu Phe
145                 150                 155                 160
```

```
Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Thr Phe Ile Phe Pro Asn Thr Ser Val Tyr Pro Glu Ala
225                 230                 235                 240

Thr Gln Arg Ile Thr Thr Arg Pro Asp Leu Pro Tyr Glu Gln Ala Arg
                245                 250                 255

Arg Ser Ala Trp Thr Ser His Ser His Pro Thr Gln Ser Lys Ala Thr
            260                 265                 270

Gln Pro Ser Ser Ser Thr Val Pro Lys Thr Glu Asp Gln Arg Pro Gln
        275                 280                 285

Leu Asp Pro Tyr Gln Ile Leu Gly Pro Thr Ser Ser Arg Leu Ala Asn
    290                 295                 300

Pro Gly Ser Gly Gln Ile Gln Leu Trp Gln Phe Leu Leu Glu Leu Leu
305                 310                 315                 320

Ser Asp Ser Ser Asn Ser Asn Cys Ile Thr Trp Glu Gly Thr Asn Gly
                325                 330                 335

Glu Phe Lys Met Thr Asp Pro Asp Glu Val Ala Arg Arg Trp Gly Glu
            340                 345                 350

Arg Lys Ser Lys Pro Asn Met Asn Tyr Asp Lys Leu Ser Arg Ala Leu
        355                 360                 365

Arg Tyr Tyr Tyr Asp Lys Asn Ile Met Thr Lys Val His Gly Lys Arg
    370                 375                 380

Tyr Ala Tyr Lys Phe Asp Phe His Gly Ile Ala Gln Ala Leu Gln Pro
385                 390                 395                 400

His Pro Pro Glu Ser Ser Met Tyr Lys Tyr Pro Ser Asp Leu Pro Tyr
                405                 410                 415

Met Ser Ser Tyr His Ala His Pro Gln Lys Met Asn Phe Val Ala Pro
            420                 425                 430

His Pro Pro Ala Leu Pro Val Thr Ser Ser Ser Phe Phe Ala Ala Pro
        435                 440                 445

Asn Pro Tyr Trp Asn Ser Pro Thr Gly Gly Ile Tyr Pro Asn Thr Arg
    450                 455                 460

Leu Pro Ala Ala His Met Pro Ser His Leu Gly Thr Tyr Tyr
465                 470                 475

<210> SEQ ID NO 117
<211> LENGTH: 80
<212> TYPE: PRT
<213> ORGANISM: Artificial Sequence
<220> FEATURE:
<223> OTHER INFORMATION: Synthetic

<400> SEQUENCE: 117

Ile Gln Leu Trp Gln Phe Leu Leu Glu Leu Leu Ser Asp Ser Ser Asn
1               5                   10                  15

Ser Ser Cys Ile Thr Trp Glu Gly Thr Asn Gly Glu Phe Lys Met Thr
            20                  25                  30

Asp Pro Asp Glu Val Ala Arg Arg Trp Gly Glu Arg Lys Ser Lys Pro
        35                  40                  45
```

```
Asn Met Asn Tyr Asp Lys Leu Ser Arg Ala Leu Arg Tyr Tyr Tyr Asp
 50                  55                  60

Lys Asn Ile Met Thr Lys Val His Gly Lys Arg Tyr Ala Tyr Lys Phe
 65                  70                  75                  80

<210> SEQ ID NO 118
<211> LENGTH: 80
<212> TYPE: PRT
<213> ORGANISM: Artificial Sequence
<220> FEATURE:
<223> OTHER INFORMATION: Synthetic

<400> SEQUENCE: 118

Ile Gln Leu Trp Gln Phe Leu Glu Leu Leu Ser Asp Ser Ala Asn
  1               5                  10                  15

Ala Ser Cys Ile Thr Trp Glu Gly Thr Asn Gly Glu Phe Lys Met Thr
                 20                  25                  30

Asp Pro Asp Glu Val Ala Arg Arg Trp Gly Glu Arg Lys Ser Lys Pro
                 35                  40                  45

Asn Met Asn Tyr Asp Lys Leu Ser Arg Ala Leu Arg Tyr Tyr Tyr Asp
 50                  55                  60

Lys Asn Ile Met Thr Lys Val His Gly Lys Arg Tyr Ala Tyr Lys Phe
 65                  70                  75                  80

<210> SEQ ID NO 119
<211> LENGTH: 80
<212> TYPE: PRT
<213> ORGANISM: Artificial Sequence
<220> FEATURE:
<223> OTHER INFORMATION: Synthetic

<400> SEQUENCE: 119

Ile Gln Leu Trp Gln Phe Leu Glu Leu Leu Thr Asp Lys Ser Cys
  1               5                  10                  15

Gln Ser Phe Ile Ser Trp Thr Gly Asp Gly Trp Glu Phe Lys Leu Ser
                 20                  25                  30

Asp Pro Asp Glu Val Ala Arg Arg Trp Gly Lys Arg Lys Asn Lys Pro
                 35                  40                  45

Lys Met Asn Tyr Glu Lys Leu Ser Arg Gly Leu Arg Tyr Tyr Tyr Asp
 50                  55                  60

Lys Asn Ile Ile His Lys Thr Ala Gly Lys Arg Tyr Val Tyr Arg Phe
 65                  70                  75                  80

<210> SEQ ID NO 120
<211> LENGTH: 79
<212> TYPE: PRT
<213> ORGANISM: Artificial Sequence
<220> FEATURE:
<223> OTHER INFORMATION: Synthetic

<400> SEQUENCE: 120

Leu Gln Leu Trp Gln Phe Leu Val Ala Leu Leu Asp Asp Pro Ser Asn
  1               5                  10                  15

Ser His Phe Ile Ala Trp Thr Gly Arg Gly Met Glu Phe Lys Leu Ile
                 20                  25                  30

Glu Pro Glu Glu Val Ala Arg Arg Trp Gly Ile Gln Lys Asn Arg Pro
                 35                  40                  45

Ala Met Asn Tyr Asp Lys Leu Ser Arg Ser Leu Arg Tyr Tyr Glu Lys
 50                  55                  60
```

Gly Ile Met Gln Lys Val Ala Gly Glu Arg Tyr Val Tyr Lys Phe
65              70                  75

<210> SEQ ID NO 121
<211> LENGTH: 79
<212> TYPE: PRT
<213> ORGANISM: Artificial Sequence
<220> FEATURE:
<223> OTHER INFORMATION: Synthetic

<400> SEQUENCE: 121

Leu Trp Asp Tyr Val Tyr Gln Leu Leu Ser Asp Ser Arg Tyr Glu Asn
1               5                   10                  15

Phe Ile Arg Trp Glu Asp Lys Glu Ser Lys Ile Phe Arg Ile Val Asp
                20                  25                  30

Pro Asn Gly Leu Ala Arg Leu Trp Gly Asn His Lys Asn Arg Thr Asn
            35                  40                  45

Met Thr Tyr Glu Lys Met Ser Arg Ala Leu Arg His Tyr Tyr Lys Leu
        50                  55                  60

Asn Ile Ile Arg Lys Glu Pro Gly Gln Arg Leu Leu Phe Arg Phe
65              70                  75

<210> SEQ ID NO 122
<211> LENGTH: 76
<212> TYPE: PRT
<213> ORGANISM: Artificial Sequence
<220> FEATURE:
<223> OTHER INFORMATION: Synthetic

<400> SEQUENCE: 122

Ile Arg Leu Tyr Gln Phe Leu Leu Asp Leu Leu Arg Ser Gly Asp Met
1               5                   10                  15

Lys Asp Ser Ile Trp Trp Val Asp Lys Asp Lys Gly Thr Phe Gln Phe
                20                  25                  30

Ser Ser Lys His Lys Glu Ala Leu Ala His Arg Trp Gly Ile Gln Lys
            35                  40                  45

Gly Asn Arg Lys Lys Met Thr Tyr Gln Lys Met Ala Arg Ala Leu Arg
        50                  55                  60

Asn Tyr Gly Lys Thr Gly Glu Val Lys Lys Val Lys
65              70                  75

We claim:

1. A composition comprising a peptide selected from d-(GRKKRRQRRRGGPLSGFSL (SEQ ID NO:35)); d-(GRWRRRRNRRAQRGGPLSGFSL (SEQ ID NO:36)); d-(GVKRKKKPGGPLSGFSL (SEQ ID NO:37)); d-(GRKKRRQRRRGGPFTGFTF (SEQ ID NO:38)); d-(GRWRRRRNRRAQRGGPFTGFTF (SEQ ID NO:39)); d-(GVKRKKKPGGPFTGFTF (SEQ ID NO: 40)); d-(GRKKRRQRRRGGTFLYPPL (SEQ ID NO:41)); d-(GRWRRRRNRRAQRGGTFLYPPL (SEQ ID NO:42)); d-(GVKRKKKPGGTFLYPPL (SEQ ID NO:43)); d-(GRKKRRQRRRGGLYPP (SEQ ID NO:44)); d-(GRWRRRRNRRAQRGGLYPP (SEQ ID NO:45)); d-(GVKRKKKPGGLYPP (SEQ ID NO:46)); d-(H2N-RKKRRQRRRGGPLSGFSL (SEQ ID NO:47)); d-(H2N-RWRRRRNRR AQRGGPLSGFSL (SEQ ID NO: 48)); d-(H2N-VKRKKKPGGPLSGFSL (SEQ ID NO:49)); d-(RKKRRQRRRGGPFTGFTF(SEQ ID NO:50)); d-(H2N-RWRRRRNRRAQRGGPFTGFTF (SEQ ID NO:51)); d-(H2N-VKRKKKPGGPFTGFTF (SEQ ID NO:52)); d-(H2N-RKKRRQRRRGGTFLYPPL (SEQ ID NO:53)); d-(H2N-RWRRRRNRRAQRGGTFLYPPL (SEQ ID NO:54)); d-(H2N-VKRKKKPGGTFLYPPL (SEQ ID NO:55)); d-(H2N-RKKRRQRRRGGLYPP (SEQ ID NO:56)); d-(H2N-RWRRRRNRRAQRGGLYPP (SEQ ID NO:57)); d-(H2N-VKRKKKPGGLYPP (SEQ ID NO:58)); l-(GHSSKLQL (SEQ ID NO: 59))-d-(GRKKRRQRRRGGPLSGFSL (SEQ ID NO:35)); l-(GHSSKLQL (SEQ ID NO:59))-d-(GRWRRRRNRRAQRGGPLSGFSL (SEQ ID NO:36)); l-(GHSSKLQL (SEQ ID NO:59))-d-(GVKRKKKPGGPLSGFSL (SEQ ID NO:37)); l-(GHSSKLQL (SEQ ID NO: 59))-d-(GRKKRRQRRRGGPFTGFTF (SEQ ID NO:38)); l-(GHSSKLQL(SEQ ID NO:59))-d-(GRWRRRRNRRAQRGGPFTGFTF (SEQ ID NO:39)); l-(GHSSKLQL (SEQ ID NO:59))-d-(GVKRKKKPGGPFTGFTF (SEQ ID NO:40)); l-(GHSSKLQL)-d-(GRKKRRQRRRGGTFLYPPL (SEQ ID NO:41)); l-(GHSSKLQL (SEQ ID NO:59))-d-(GRWRRRRNRRAQRGGTFLYPPL (SEQ ID NO:42)); l-(GHSSKLQL (SEQ ID NO:59))-d-(GVKRKKKPGGTFLYPPL (SEQ ID NO:43)); l-(GHSSKLQL (SEQ ID NO:59))-d-(GRKKRRQRRRGGLYPP (SEQ ID NO:44)); l-(GHSSKLQL (SEQ ID NO:59))-d-(GRWRRRRNRRAQRGGLYPP (SEQ ID NO:45)); l-(GHSSKLQL (SEQ ID NO:59) d-(GVKRK-KKPGGLYPP (SEQ ID NO:46)); d-GRRRQRRKKRGGT-FLYPPL (SEQ ID NO:60); and dGRRRQRRKKRGGPLS-GFSL (SEQ ID NO:61).

2. The composition of claim 1, wherein said composition further comprises a nanostructure.

3. The composition of claim 2, wherein said nanostructure is selected from a liposome, a micelle, PEG, and a dendrimer.

4. The composition of claim 3, wherein said composition is encapsulated in said liposome or micelle.

5. The composition of claim 2, wherein said nanostructure comprises a prostate selective targeting moiety (PSTM) on its surface.

6. The corn position of claim 2, wherein said peptide is attached to said nanostructure via a linker, wherein said linker is a selectively cleavable moiety.

7. The composition of claim 6, wherein said linker is HSSKLQL (SEQ ID NO:62) or a hypoxia-sensitive p-nitrobenzyloxy linker.

8. A method of binding to an ETS family member gene in a cell, wherein the ETS member gene is selected from ERG, ETV1, ETV6 and ETS1, comprising contacting said cell with a peptide of claim 1.

\* \* \* \* \*